(12) United States Patent
Bassarab et al.

(10) Patent No.: US 7,723,306 B2
(45) Date of Patent: *May 25, 2010

(54) SPRAY-DRIED POWDER COMPRISING AT LEAST ONE 1,4 O-LINKED SACCHAROSE-DERIVATIVE AND METHODS FOR THEIR PREPARATION

(75) Inventors: Stefan Bassarab, Biberach (DE); Karoline Bechtold-Peters, Biberach (DE); Richard Fuhrherr, Nuremberg (DE); Wolfgang Friess, Iffeldorf (DE); Patrick Garidel, Norderstedt (DE); Torsten Schultz-Fademrecht, Biberach (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 776 days.

This patent is subject to a terminal disclaimer.

(21) Appl. No.: 11/120,104

(22) Filed: May 2, 2005

(65) Prior Publication Data

US 2005/0250705 A1   Nov. 10, 2005

Related U.S. Application Data

(60) Provisional application No. 60/572,210, filed on May 18, 2004.

(30) Foreign Application Priority Data

May 10, 2004   (DE) ....................... 10 2004 022 926

(51) Int. Cl.
*A61K 31/715* (2006.01)
*A61K 38/05* (2006.01)
*A61K 38/04* (2006.01)

(52) U.S. Cl. ............................. 514/18; 514/19; 514/61

(58) Field of Classification Search .................. 514/18, 514/19, 61
See application file for complete search history.

(56) References Cited

U.S. PATENT DOCUMENTS

| | | | |
|---|---|---|---|
| 3,634,582 A | 1/1972 | Hartley | |
| 3,894,146 A | 7/1975 | Tsuyama | |
| 3,906,950 A | 9/1975 | Cocozza | |
| 4,013,075 A | 3/1977 | Cocozza | |
| 4,570,630 A | 2/1986 | Elliott et al. | |
| 4,811,731 A | 3/1989 | Newell et al. | |
| 5,035,237 A | 7/1991 | Newell et al. | |
| 5,296,472 A | 3/1994 | Sanchez et al. | |
| 5,320,094 A | 6/1994 | Laube et al. | |
| 5,458,135 A | 10/1995 | Patton et al. | |
| 5,489,577 A | 2/1996 | Ikeda et al. | |
| 5,505,945 A | 4/1996 | Gristina et al. | |
| 5,522,385 A | 6/1996 | Lloyd et al. | |
| 5,626,874 A | 5/1997 | Conte et al. | |
| 5,672,581 A | 9/1997 | Rubsamen et al. | |
| 5,753,469 A * | 5/1998 | Nakada et al. ................ 435/99 |
| 5,785,049 A | 7/1998 | Smith et al. | |
| 5,922,324 A | 7/1999 | Aga et al. | |
| 5,947,118 A | 9/1999 | Hochrainer et al. | |
| 5,972,388 A | 10/1999 | Sakon et al. | |
| 6,453,795 B1 | 9/2002 | Eicher et al. | |
| 2003/0059511 A1 | 3/2003 | Ishii | |
| 2005/0250704 A1 | 11/2005 | Bassarab et al. | |
| 2005/0250705 A1 | 11/2005 | Bassarab et al. | |
| 2005/0255119 A1 | 11/2005 | Bassarab et al. | |
| 2006/0008574 A1 | 1/2006 | Begli et al. | |

FOREIGN PATENT DOCUMENTS

| | | |
|---|---|---|
| CA | 2273241 | 7/1998 |
| CA | 2273277 | 7/1998 |
| CA | 2297174 | 2/1999 |
| CA | 2565019 | 12/2005 |
| DE | 1792207 | 11/1971 |
| DE | 3625685 | 3/1987 |
| DE | 19732351 | 2/1999 |
| DE | 19953727 | 5/2001 |
| EP | 129985 | 1/1985 |
| EP | 237507 | 9/1987 |
| EP | 467172 | 1/1992 |
| EP | 630651 | 12/1994 |
| EP | 0630651 A2 | 12/1994 |

(Continued)

OTHER PUBLICATIONS

Adler, M. Dissertation. Jul. 23, 1999, Chapter 2.3, pp. 11-19.

(Continued)

*Primary Examiner*—Shaojia Anna Jiang
*Assistant Examiner*—Ganapathy Krishnan
(74) *Attorney, Agent, or Firm*—Michael P. Morris; Mary-Ellen M. Devlin; Anthony P. Bottino

(57) ABSTRACT

The present invention relates to a spray-dried powder and method for its manufacture. A spray dried powder containing a pharmaceutical active substance and one or more 1,4 O-linked saccharose derivatives chosen from the compounds: 1,4 O-linked D-gal-saccharose (lactosucrose), 1,4 O-linked D-glu-saccharose (glucosyl sucrose) or 1,4 O-linked glu-glu-saccharose (maltosyl sucrose). Preferred combinations are such that they contain glucosyl and maltosyl sucrose.

45 Claims, 13 Drawing Sheets

FOREIGN PATENT DOCUMENTS

| | | |
|---|---|---|
| EP | 0630651 A3 | 6/1996 |
| EP | 0739986 | 10/1996 |
| EP | 745382 | 12/1996 |
| EP | 0745382 A1 | 12/1996 |
| EP | 911037 | 4/1999 |
| EP | 974358 | 1/2000 |
| EP | 1174148 | 1/2002 |
| EP | 1223175 | 7/2002 |
| WO | 8911297 | 11/1989 |
| WO | 9013328 | 11/1990 |
| WO | 9114468 | 10/1991 |
| WO | 9407607 | 4/1994 |
| WO | 9428958 | 12/1994 |
| WO | 9531479 | 11/1995 |
| WO | 9609814 | 4/1996 |
| WO | 9632096 | 10/1996 |
| WO | WO 96/32149 | 10/1996 |
| WO | 9704801 | 2/1997 |
| WO | 9712683 | 4/1997 |
| WO | 9712687 | 4/1997 |
| WO | 9720590 | 6/1997 |
| WO | 9741031 | 11/1997 |
| WO | 9741833 | 11/1997 |
| WO | 9744013 | 11/1997 |
| WO | WO 98/16205 * | 4/1998 |
| WO | 9831346 | 7/1998 |
| WO | 9907340 | 2/1999 |
| WO | 99/27071 | 6/1999 |
| WO | WO 99/27071 | 6/1999 |
| WO | 9966903 | 12/1999 |
| WO | 00/09164 | 2/2000 |
| WO | 0100263 | 1/2001 |
| WO | 0010541 | 3/2001 |
| WO | 0113893 | 3/2001 |
| WO | 0132144 | 5/2001 |
| WO | 0243750 | 6/2002 |
| WO | 03/041512 | 5/2003 |
| WO | WO 03/041512 A1 | 5/2003 |
| WO | 03/064473 | 8/2003 |
| WO | 03/080027 | 10/2003 |
| WO | WO 03/080027 A1 | 10/2003 |
| WO | 03104473 | 12/2003 |
| WO | 2005112996 | 12/2005 |

OTHER PUBLICATIONS

Adler, M. Dissertation. Jul. 23, 1999, Chapter 4, pp. 41-56.
Adler, M. Dissertation. Jul. 23, 1999, Chapter 5.1, pp. 58-70.
Adler, M. Dissertation. Jul. 23, 1999, Chapter 5.2, pp. 71-83.
Adler, M. Dissertation. Jul. 23, 1999, Chapter 5.4, pp. 84-102.
Adler, M. Dissertation. Jul. 23, 1999, Chapter 6.3, pp. 111-123.
Adler, M. et al., Foreword, "Stability and surface activity of lactate dehydrogenase in spray-dried trehalone". Journal of Pharmaceutical Sciences, vol. 88, No. 2, 1999, pp. 199-208.
Bauer, et al. Basic Physical-Chemicals Principles for Dosage Forms, Edition 7, 2002, Chapter 6, pp. 167-191.
Bauer, et al. Basic Physical-Chemicals Principles for Dosage Forms, Edition 6, 1999, Chapter 2, pp. 103-107.
Bauer, et al. Basic Physical-Chemicals Principles for Dosage Forms, Edition 6, 1999, Chapter 4, pp. 70-73.
Boctor, A.M., et al., "Enhancement of the stability of thrombin by polyols: microcalorimetric studies". Journal of Pharmacy and Pharmacology, vol. 44, No. 7, 1992, pp. 600-603.
Bosquillon, C. et al., "Influence of formation excipients and physical characteristics of inhalation dry powders on their aerosolization performance". Journal of Controlled Release, vol. 70, No. 3, 2001, pp. 329-339.
Broadhead, J. et al., "The effect of process and formulation variables on the properties of spray-dried b-galactosidase". Journal Pharm. Pharmacol, 1994, vol. 46, No. 6, pp. 458-467.

Chamow, S.M.,et al., Editors. "Antibody Fusion Proteins". Wiley-Liss Publication. Copyright 1999. pp. 1-316.
Chan, H.K. et al., "Effects of additives on heat denaturation of rhDNase in solutions". Pharmaceutical Research, vol. 13, No. 5, 1996, pp. 756-761.
Chang, B.S., et al., "Stablization of lyophilized porcine pancreatic elastase". Pharmaceutical Research, vol. 10, No. 10, 1993, pp. 1478-1483.
Costantino, H.R., et al., "Effect of mannitol crystallization on the stability and aerosol performance of a spray-dried pharmaceutical protein, recombinant humanized anti-IgE monoclonal antibody". Journal of Pharmaceutical Sciences, Vo.87, No. 11, 1998, pp. 1406-1411.
Dix, D.B., et al. "Increasing the Physical Stability of a Hydrophobic Protein: RHCNTF". Pharmaceutical Research (Supplement), 1995, BIOTEC 2074, 12, S-97.
Herman, A.C. et al., "Characterization, formulation, and stability of neupogen (Filgrastim), a recombinant human granulocyte-colony stimulating factors". Pharmaceutical Biotechnology, vol. 9, 1996, pp. 303-328.
Hu, S.Z. et al., "Minibody: a novel engineered anti-carcinoembryonic antigen antibody fragment (single-chain Fv-CH3) which exhibits rapid, high-level targeting of xenografts". Cancer Research, vol. 56, 1996, pp. 3055 ff.
Huston, J.S. et al., "Protein engineering of antibody binding sites: recovery of specific activity in an anti-digoxin single-chain Fv analogue produced in *Escherichia coli*". Proc. Natl. Acad. Sci., USA, vol. 85, 1988, pp. 5879 ff.
International Search Report for PCT/EP2005/004806 mailed Aug. 1, 2005.
International Search Report for PCT/EP2005/004807 mailed Oct. 13, 2005.
International Search Report for PCT/EP2005/004808 mailed Jul. 17, 2006.
Kibbe (eds). "Handbook of Pharmaceutical Excipients". American Pharmaceutical Association & The Pharmaceutical Society of Great Britain. 1986, pp. 153-162, 304-308, 231.
Kortt, A.A. et al., "Single-chain Fv fragments of anti-neuraminidase antibody NC10 containing five-and ten-residue linkers form dimmers and with zero-residue linker a trimer". Protein Engineering, vol. 10, No. 4, 1997, pp. 423 ff.
Lovejoy, B. et al. "Crystal structure of a synthetic triple-standard a-Helical bundle". Science, vol. 259, 1993, pp. 1288 ff.
Maa, Y.F. et al., "Effect of spray drying and subsequent processing conditions on residual moisture content and physical/biochemical stability of protein inhalation powders". Pharmaceutical Research, vol. 15, No. 5, 1998, pp. 768-775.
Maa, Y.F., et al., "The effect of operating and formulation variables on the morphology of spray-dried protein particles". Pharmaceutical Development and Technology, vol. 2, No. 3, 1997, pp. 213-223.
Masters. K. Spray Drying Handbook. 4th Edition, Longman Scientific & Technical. Copublished in the US with John Wiley & Sons, Inc., NY. Boehringer Ingelheim Vetmedica GmbH. 1985, pp. 1-696, Parts 1 of 5.
Masters. K. Spray Drying Handbook. 4th Edition, Longman Scientific & Technical. Copublished in the US with John Wiley & Sons, Inc., NY. Boehringer Ingelheim Vetmedica GmbH. 1985, pp. 1-696, Parts 2 of 5.
Masters. K. Spray Drying Handbook. 4th Edition, Longman Scientific & Technical. Copublished in the US with John Wiley & Sons, Inc., NY. Boehringer Ingelheim Vetmedica GmbH. 1985, pp. 1-696, Parts 3 of 5.
Masters. K. Spray Drying Handbook. 4th Edition, Longman Scientific & Technical. Copublished in the US with John Wiley & Sons, Inc., NY. Boehringer Ingelheim Vetmedica GmbH. 1985, pp. 1-696, Parts 4 of 5.
Masters. K. Spray Drying Handbook. 4th Edition, Longman Scientific & Technical. Copublished in the US with John Wiley & Sons, Inc., NY. Boehringer Ingelheim Vetmedica GmbH. 1985, pp. 1-696, Parts 5 of 5.

Niven, R.W., et al., "Pulmonary delivery of powders and solutions containing recombinant human granulocyte colony-stimulating factor (rhG-CSF) to the rabbit". Pharmaceutical Research, vol. 11, No. 8, 1994, pp. 1101-1109.

Pack, P. et al., "Improved bivalent miniantibodies, with identical avidy as whole antibodies, produced by high cell density fermentation of *Escherichia coli*". Bio/technology, vol. 11, 1993, pp. 1271 ff.

Pack, P. et al., "Tetravalent miniantibodies with high avidity assembling in *Escherichia coli*". Journal Mo. Biol., 1995, 246, p. 28-34.

Perisic, O. et al., "Crystal structure of a diabody, a bivalent antibody fragment". Structure, vol. 2, 1994, pp. 1217 ff.

Remmele, Jr. R.L., et al., "Interleukin-1 receptor (IL-1R) liquid formulation development using differential scanning calorimetry". Pharmaceutical Research, vol. 15, No. 2, 1998, pp. 200-208.

Timasheff, S.N. et al., "Control of protein stability and reactions by weakly interacting cosolvents: the simplicity of the complicated". Advances in Protein Chemistry, vol. 51, 1998, p. 355.

Timasheff, S.N.,. "The Control of protein stability and association by weak interactions with water: How do solvents affect these processes?". Annual Rev. Biophysics and Biomolecular Structure, vol. 22, 1993, pp. 67-97.

Vidgren, M.T., et al., "Comparison of physical and inhalation properties of spray-dried and mechanically micronized disodium cromoglycate". Int. J. Pharmaceutics, vol. 35, 1987, pp. 139-144.

Willmann, M. Dissertation Stabilization of Pharmaceutical Protein Solutions by Vacuum Drying, 2003, pp. 14-23.

Windisch, V, et al. "Degradation Pathways of Salmon Calcitonin in Aqueous Solutions". Journal of Pharmaceutical Sciences, vol. 86, No. 3, Mar. 1997, pp. 359-364.

Xie, G., et al., "The thermodynamic mechanism of protein stabilization by trehalose". Biophysical Chemistry, vol. 64, No. 1, 1997, pp. 25-43.

Xie, G., et al., "Mechanism of the stabilization of ribonuclease A by sorbitol: Preferential hydration is greater for the denatured than for the native protein". Protein Science, vol. 6, 1997, pp. 211-221.

Zhang, J. et al., "NMR study of the cold, heat, and pressure unfolding of ribonuclease A". Biochemistry, 1995, vol. 34, No. 27, pp. 8631-8641.

* cited by examiner

Figure: 1
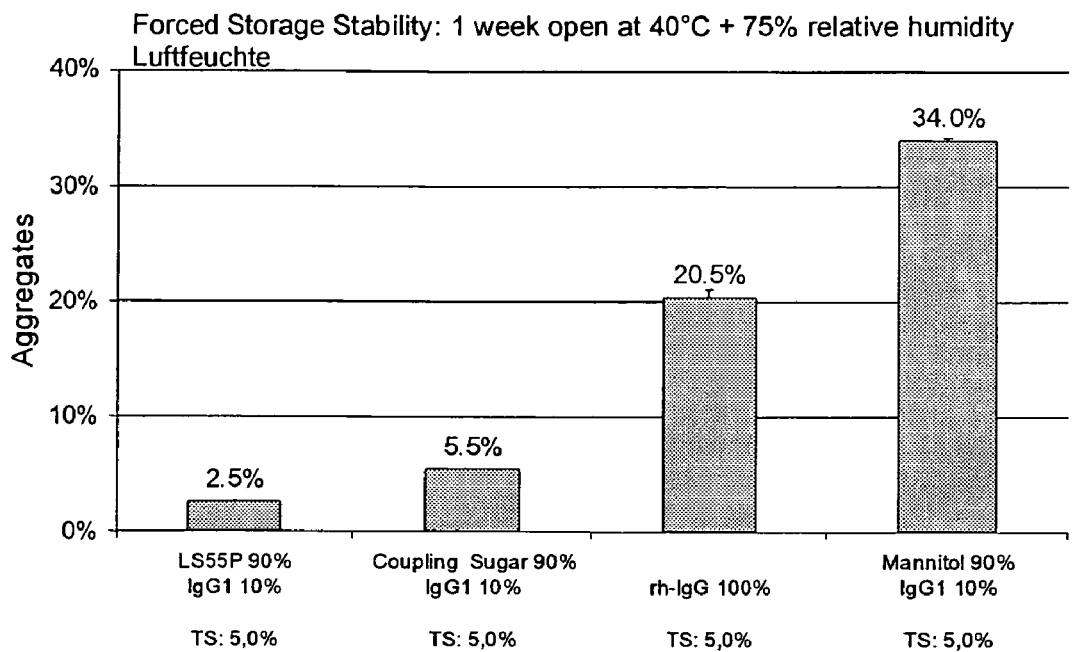
Figure: 2
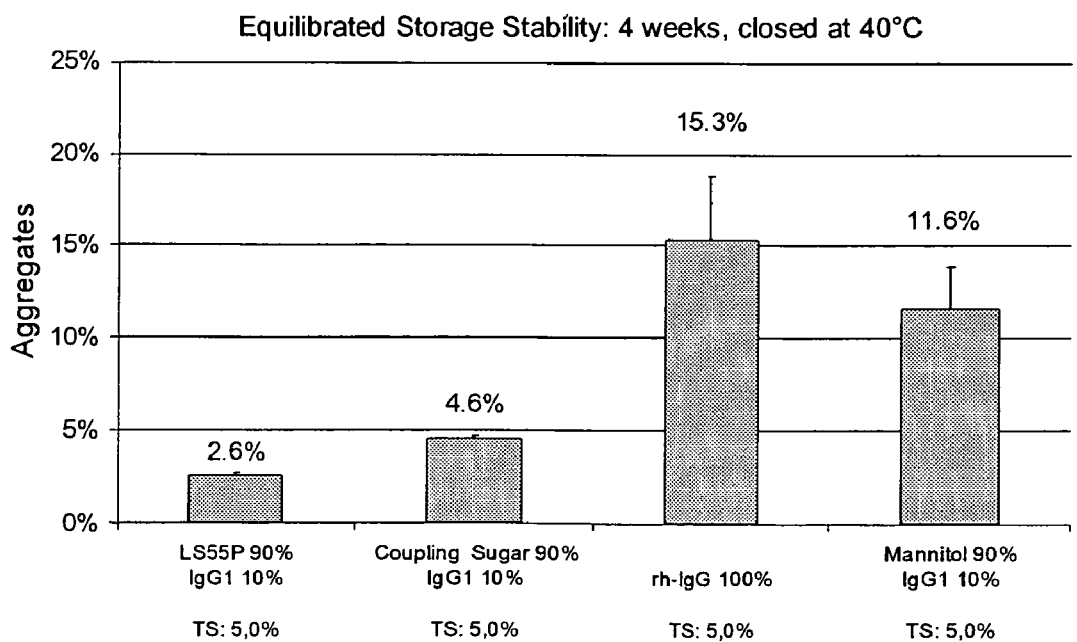

Figure: 3
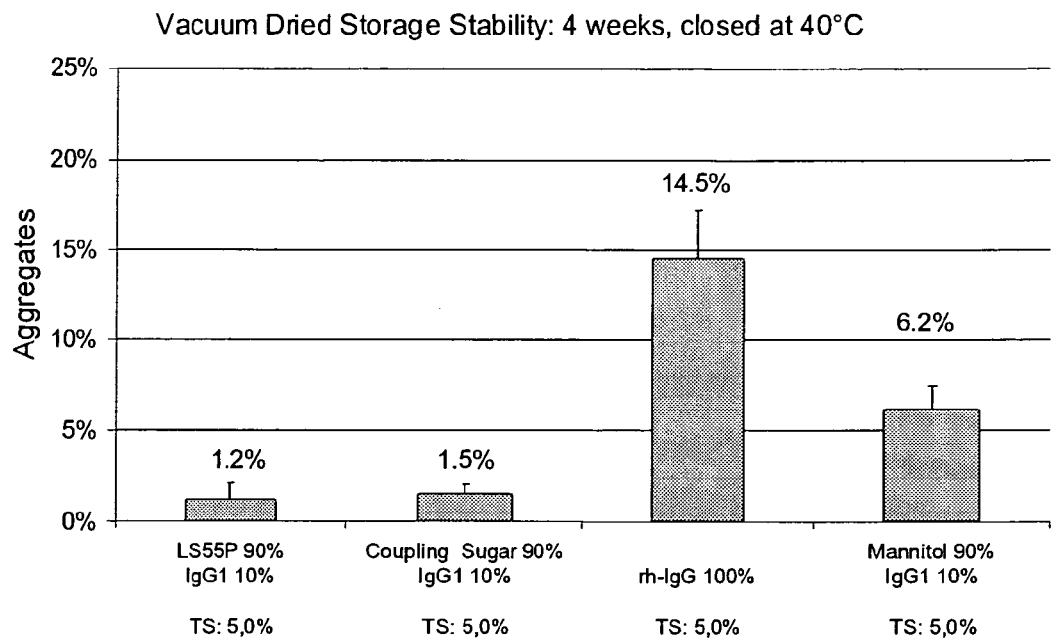
Figure: 4
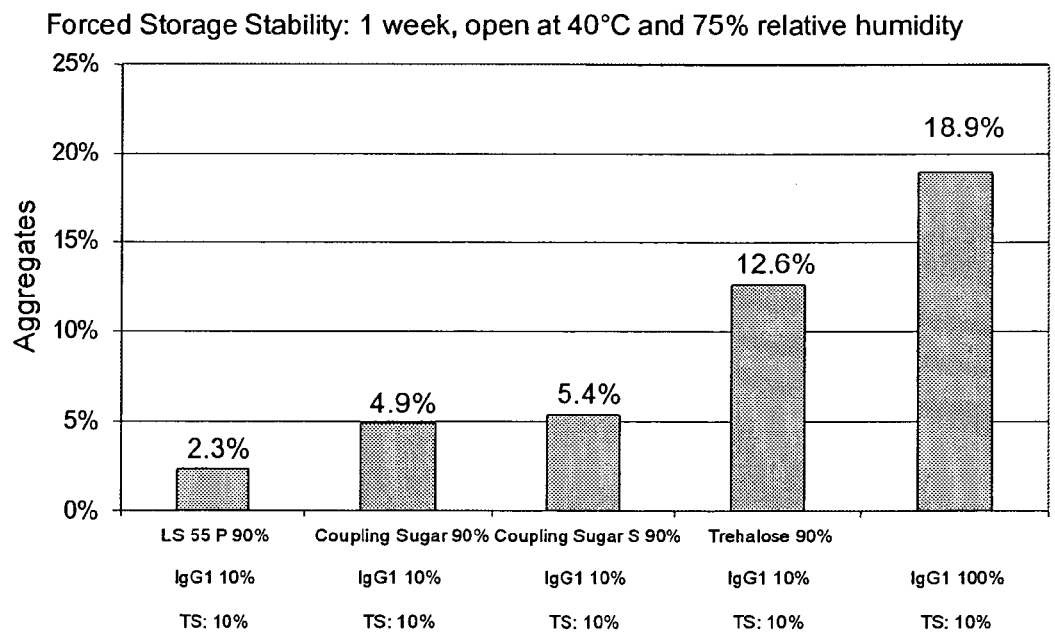

Figure: 5
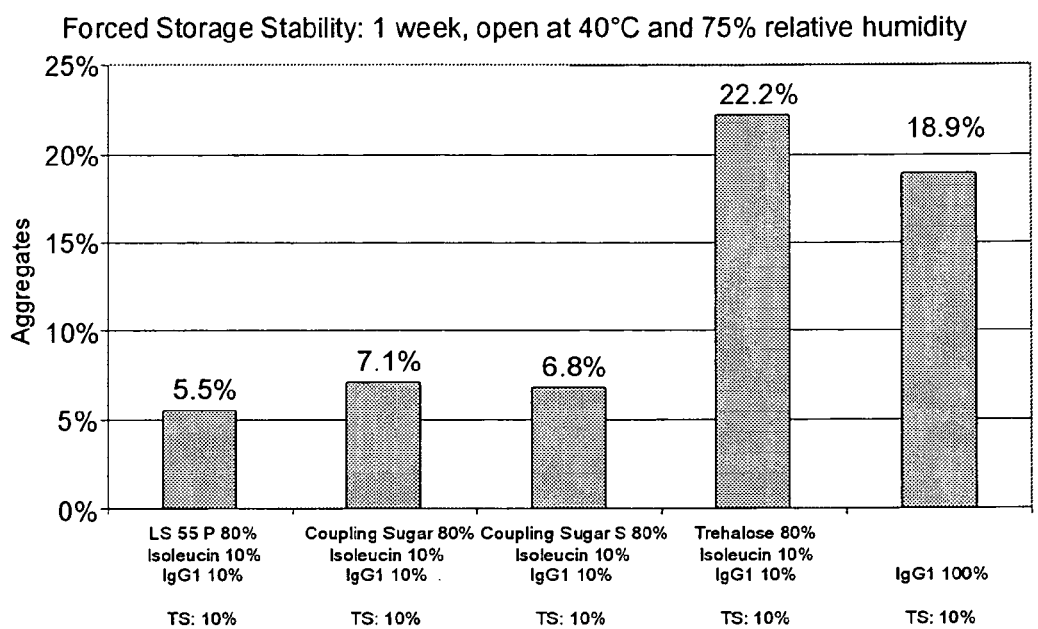
Figure: 6
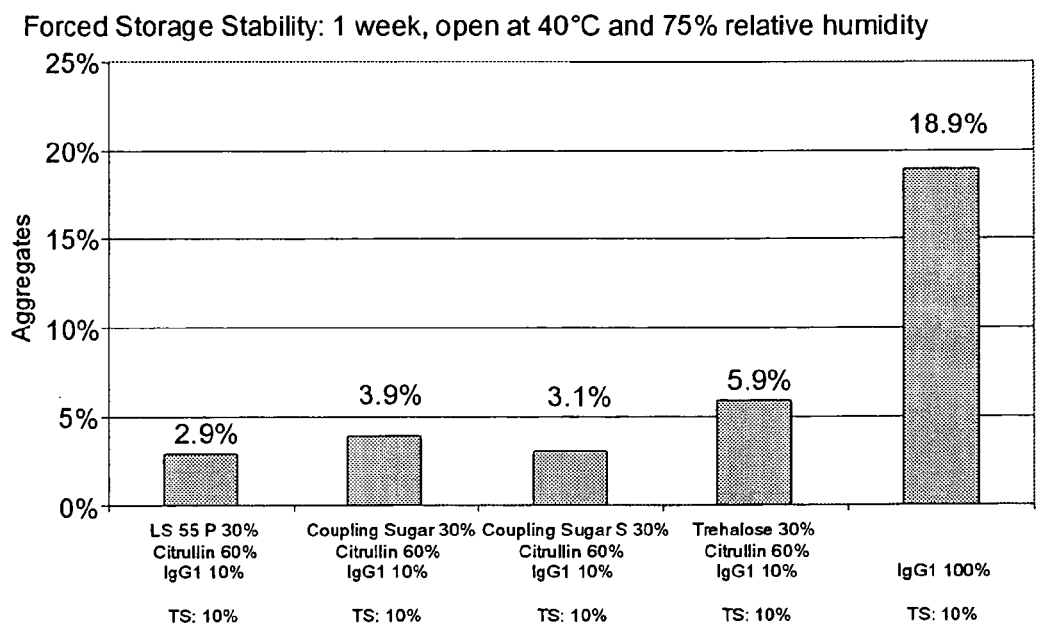

Figure: 7
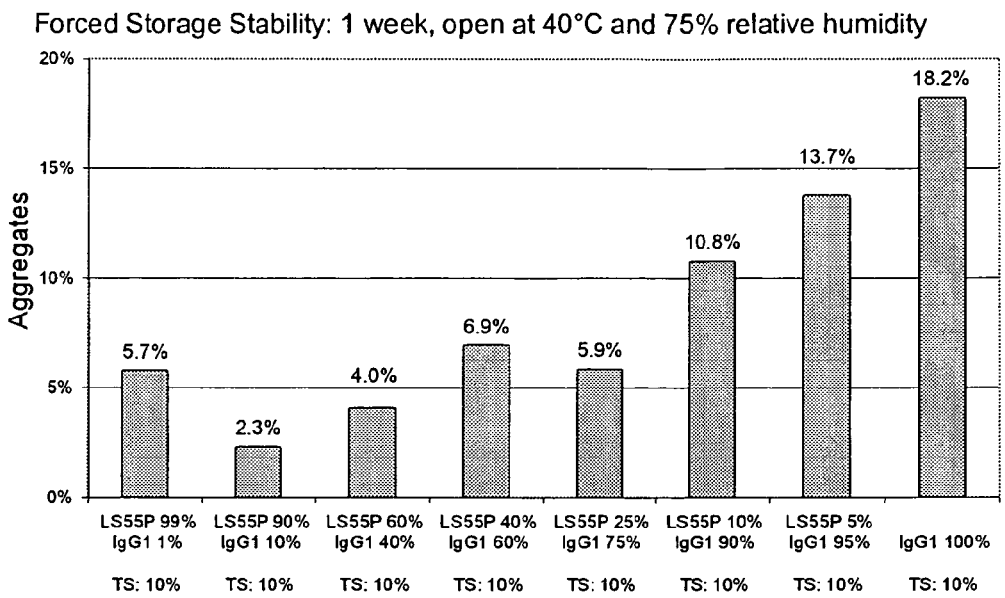
Figure: 8
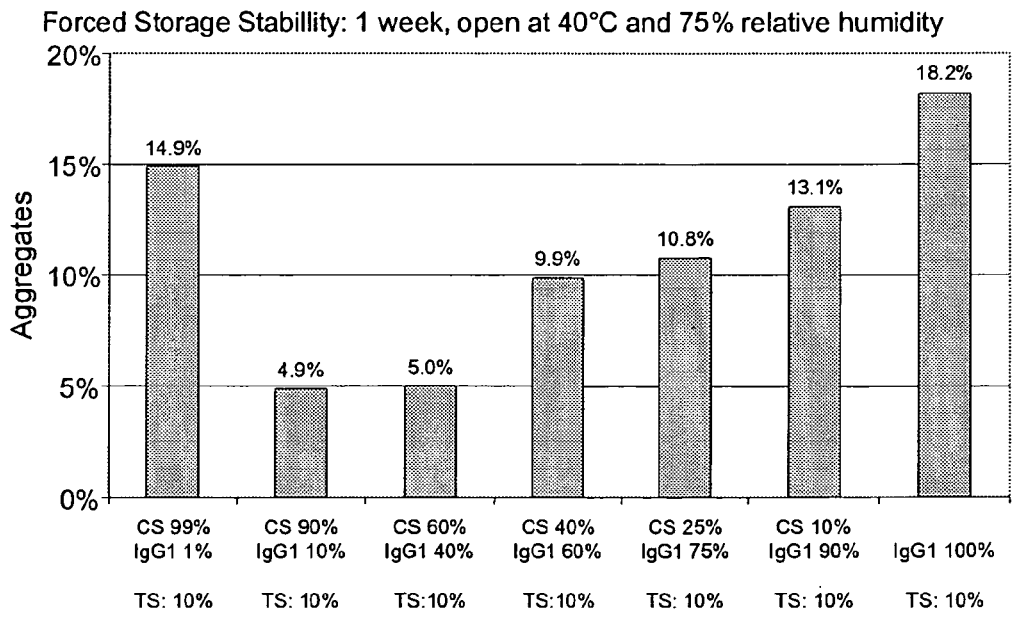

Figure: 9
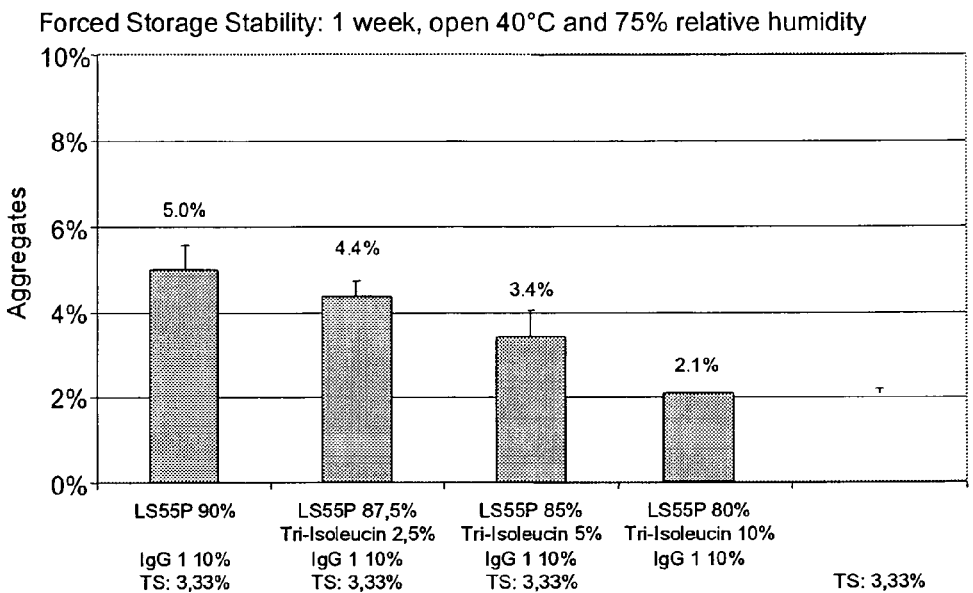
Figure: 10
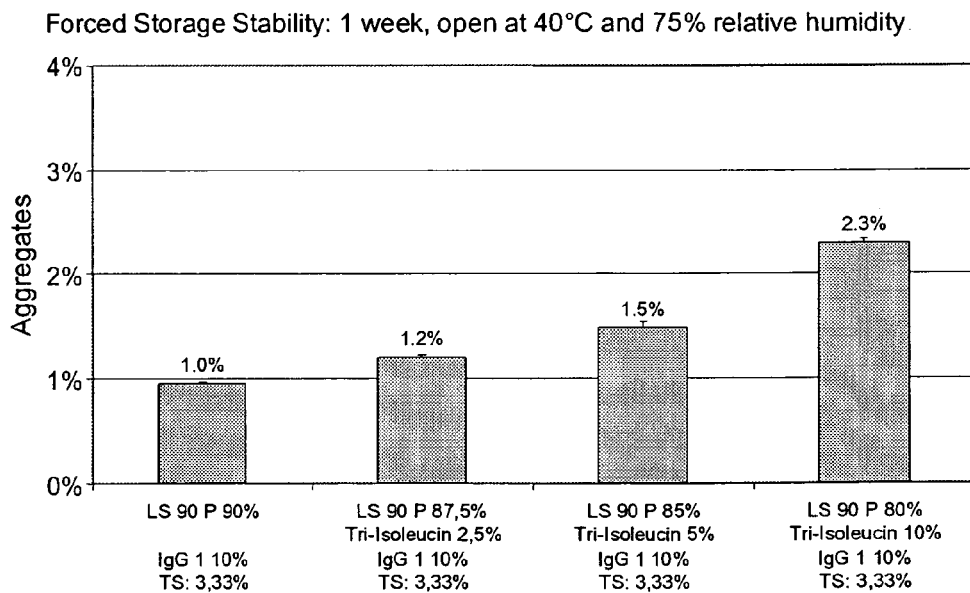

Figure: 11
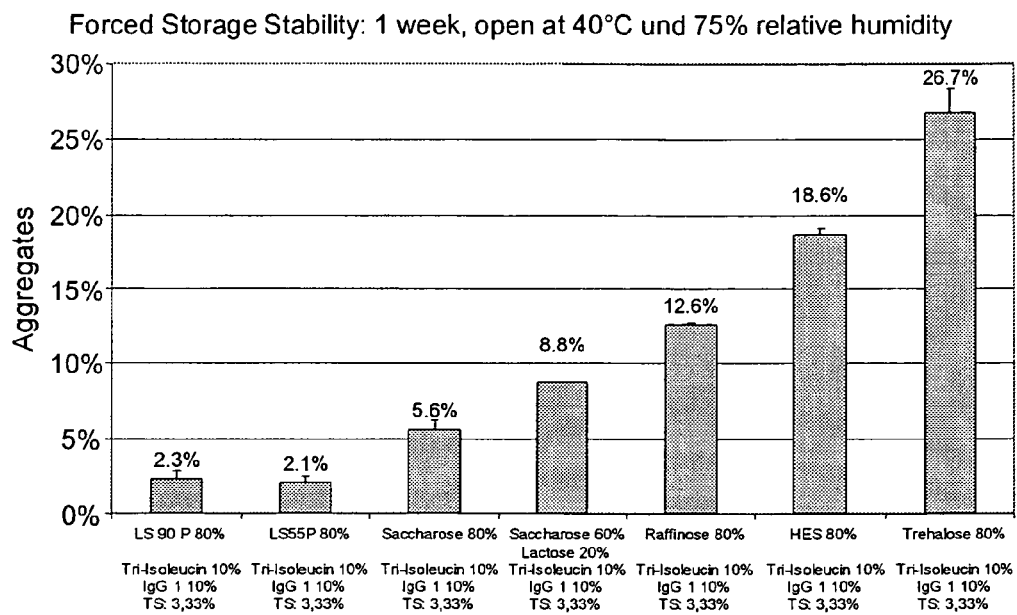
Figure: 12
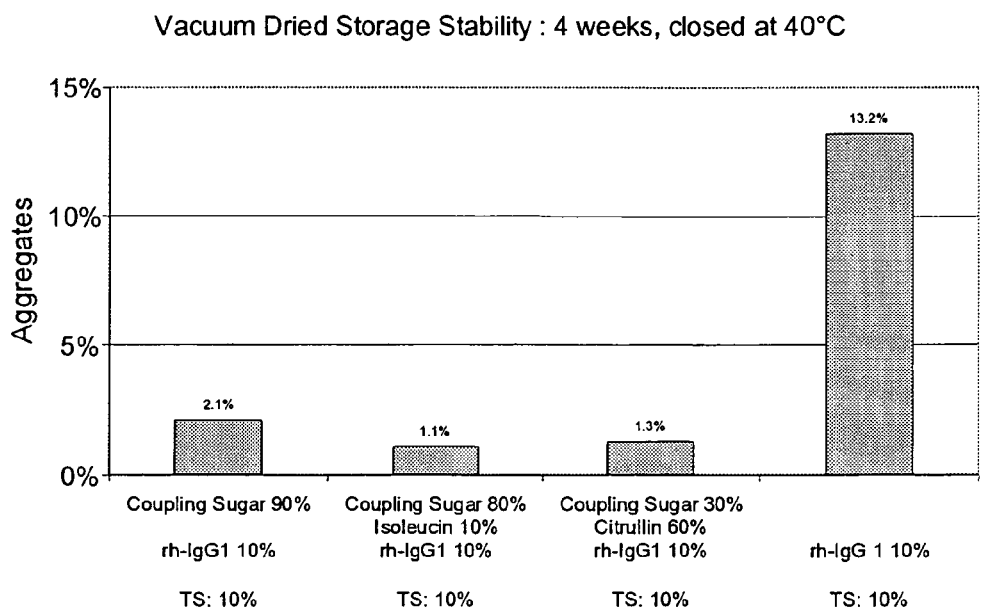

Figure: 13
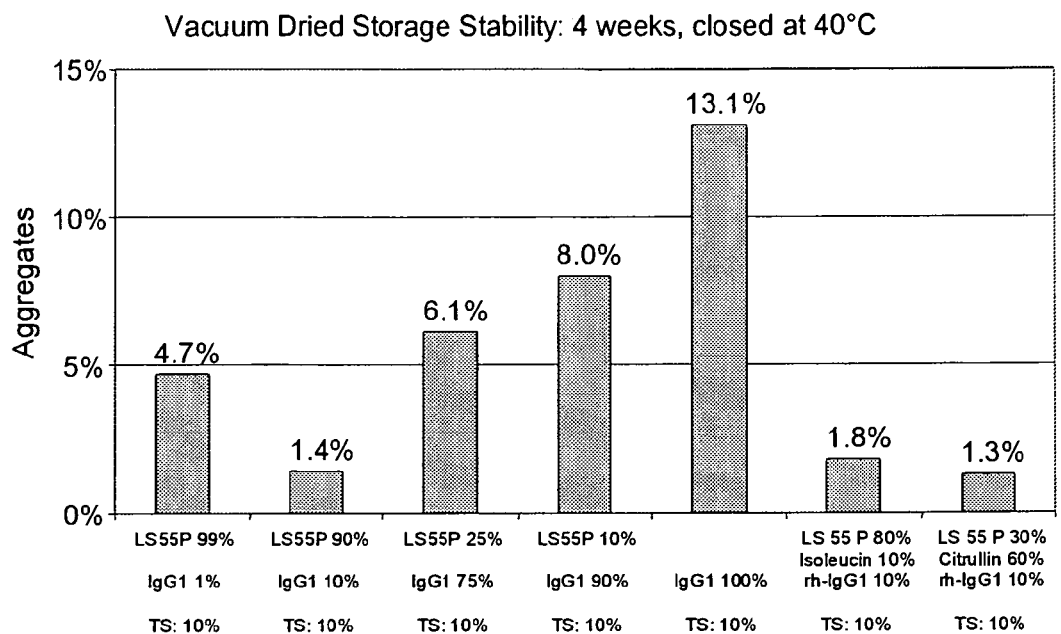
Figure: 14
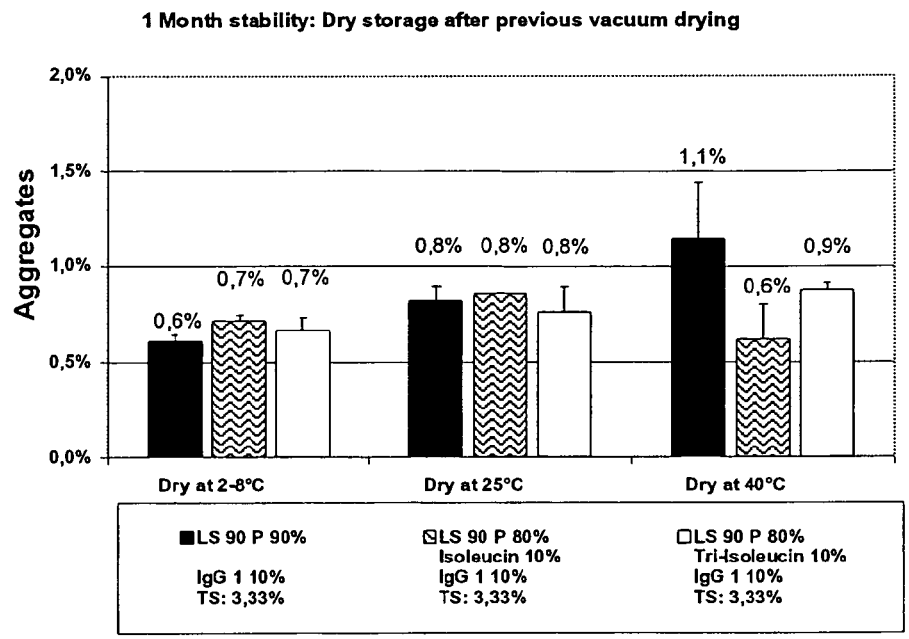

Figure: 15
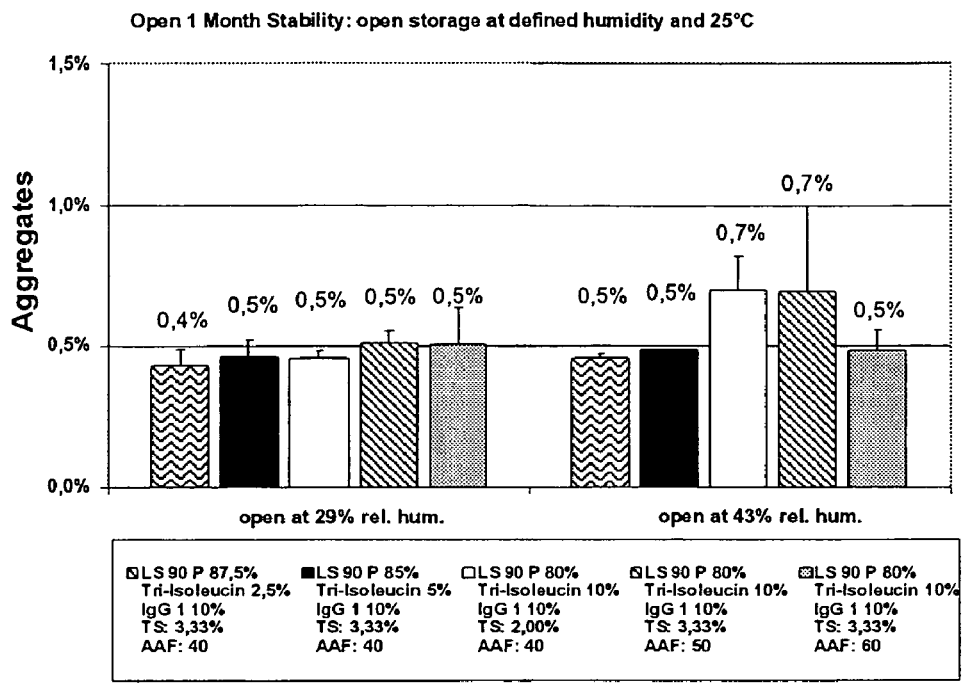
Figure 16
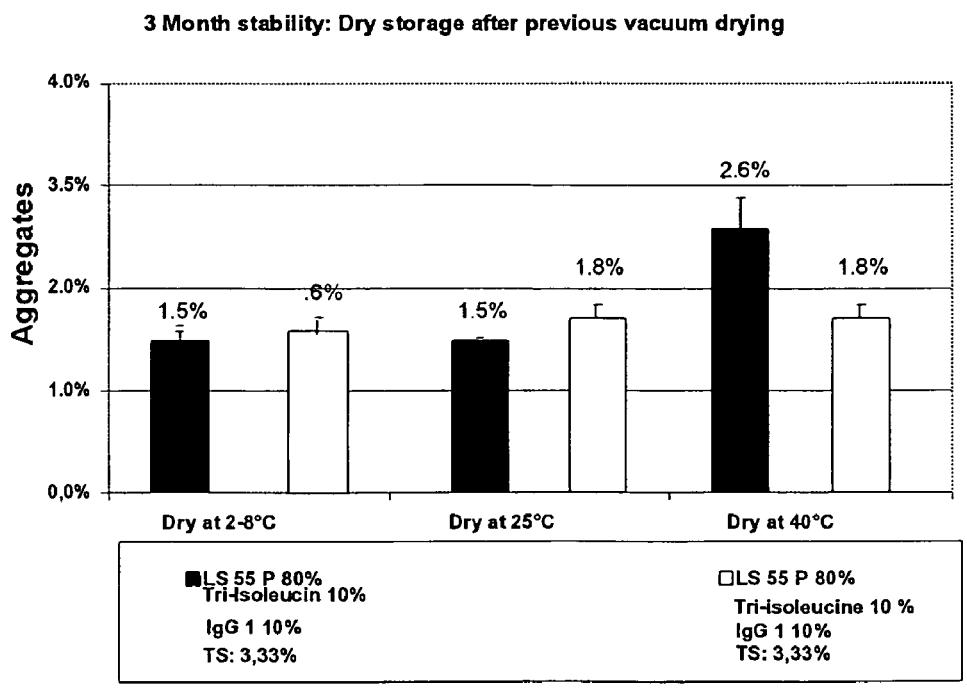

Figure: 17
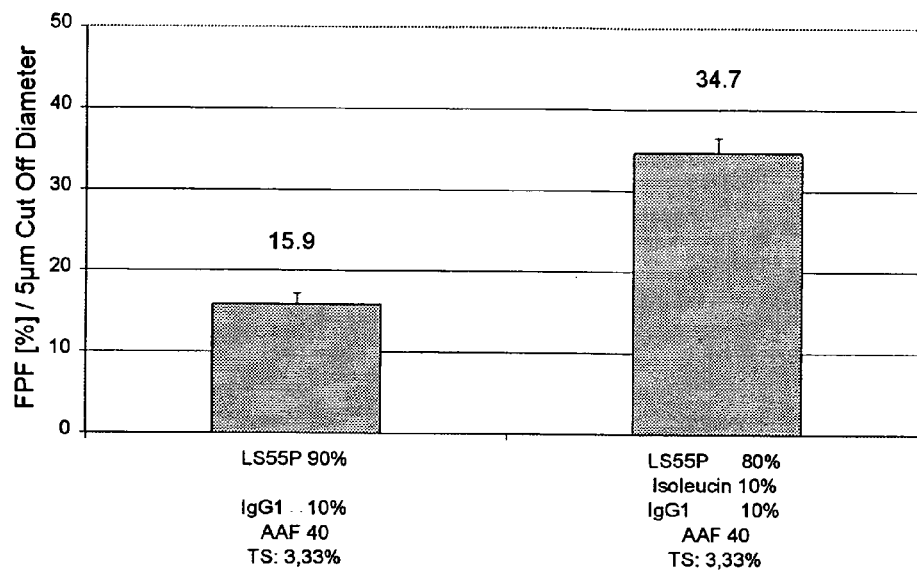
Figure: 18
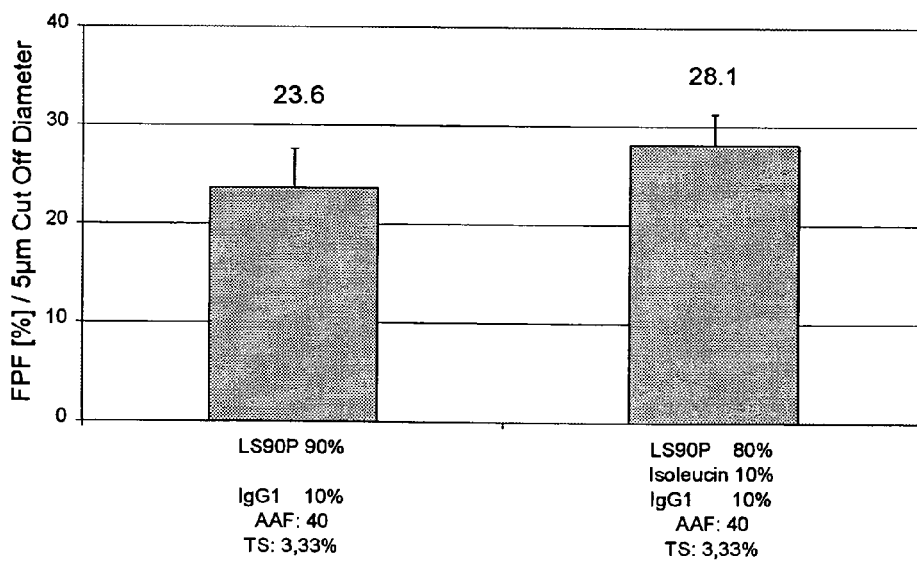

Figure: 19
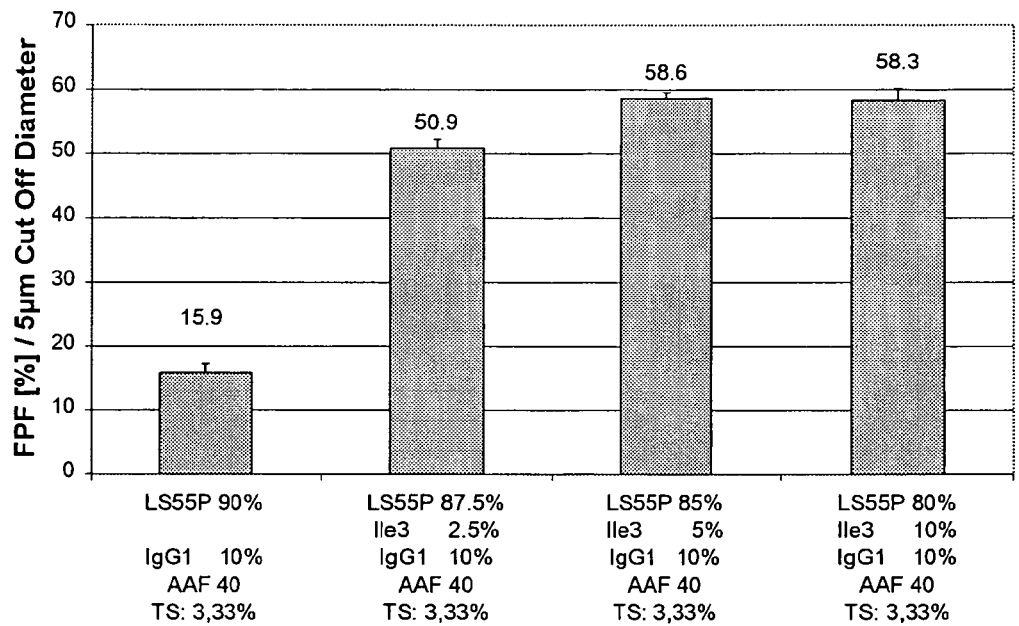
Figure: 20
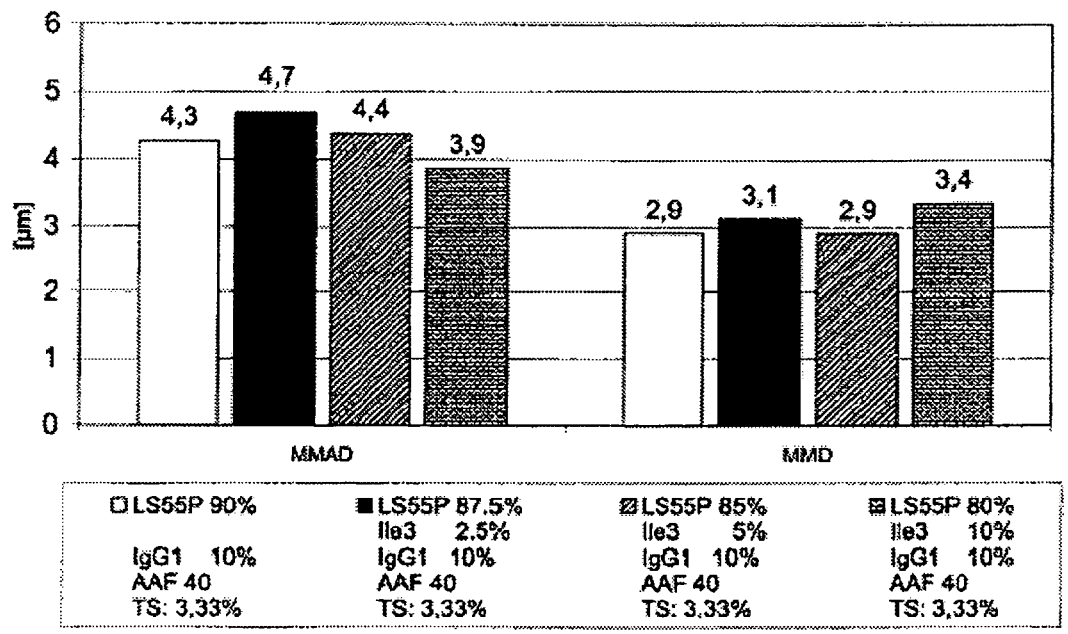

Figure: 21
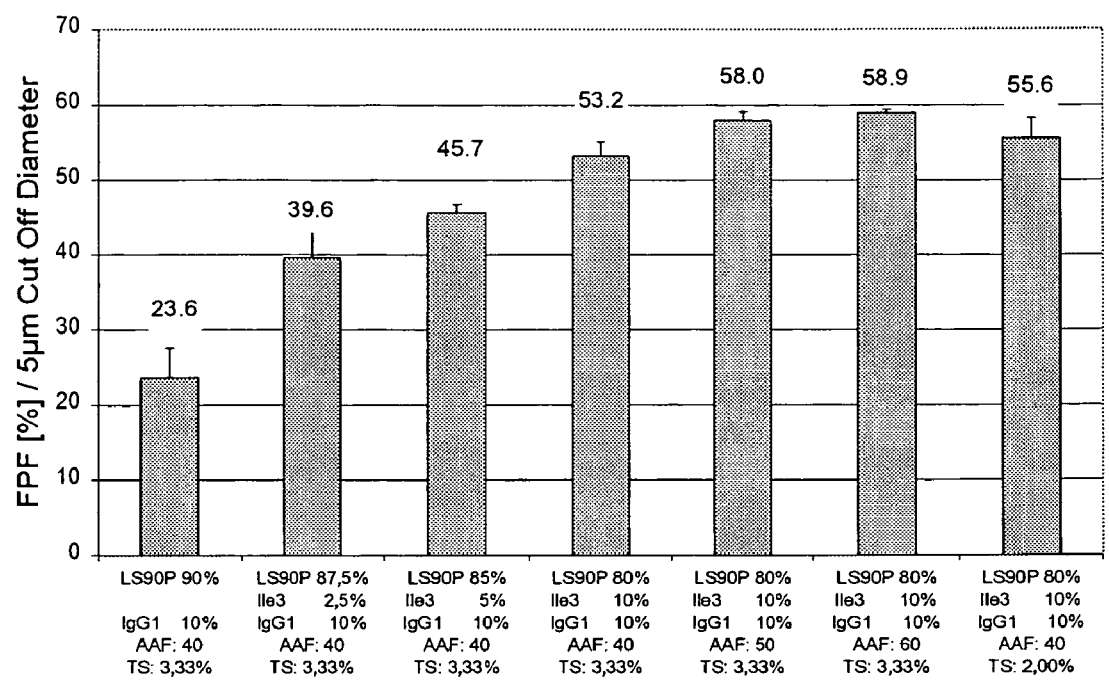

Figure: 22
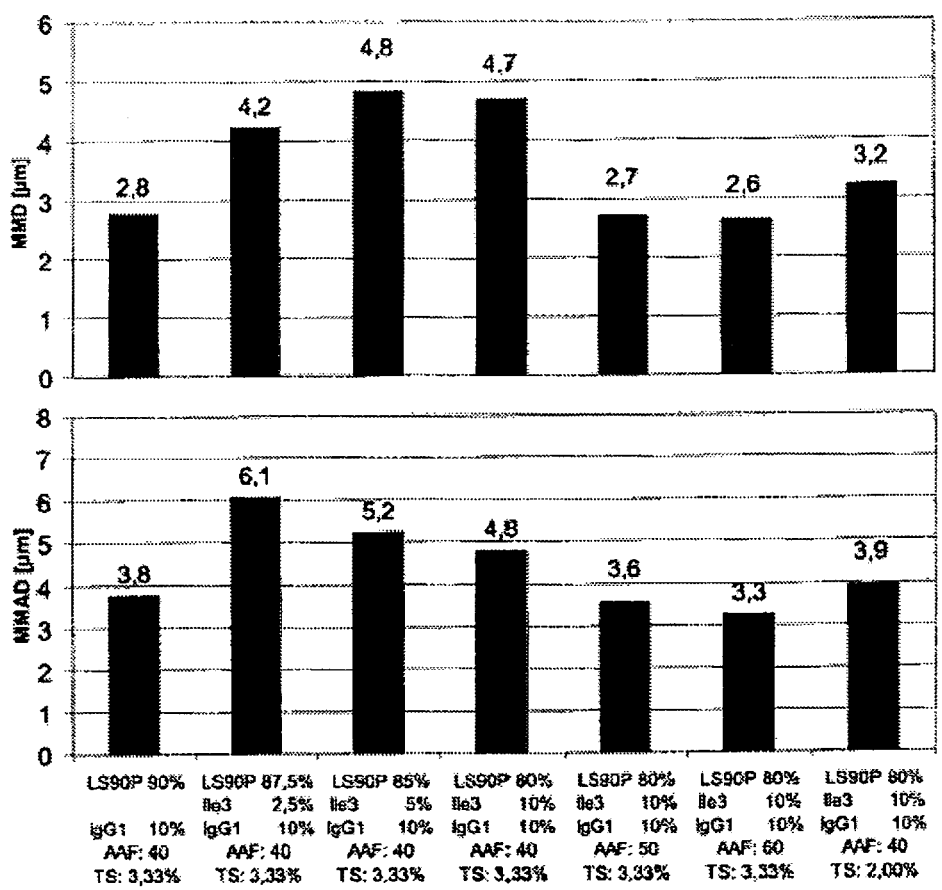

Figure: 23
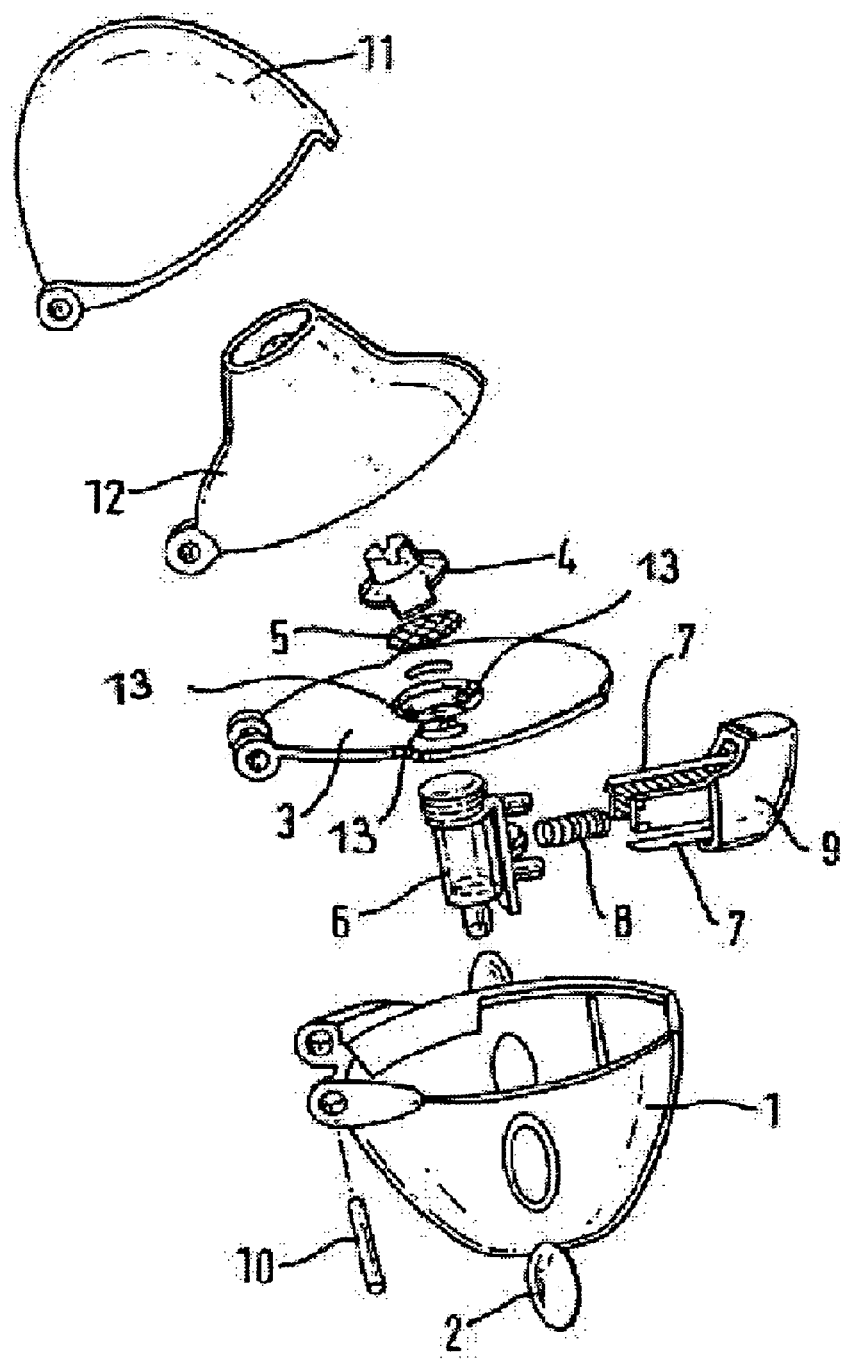

SPRAY-DRIED POWDER COMPRISING AT LEAST ONE 1,4 O-LINKED SACCHAROSE-DERIVATIVE AND METHODS FOR THEIR PREPARATION

FIELD OF THE INVENTION

The invention relates to the use of novel oligosaccharides/mixtures of oligosaccharides for manufacturing and stabilizing of pharmaceutical compositions, primarily powders containing a pharmaceutical active substance. The manufacture of the powder is done preferably by spray drying or freeze drying. The present invention relates in particular to corresponding powders containing antibodies and a method for their manufacture.

BACKGROUND OF THE INVENTION

Active substance/active substance preparations in aqueous solutions are subject in part to instabilities, which can result in reduced efficacy or bioactivity and increased toxicity or intolerance reactions. This applies both to classical pharmaceuticals as well as to peptide active substances or active substances containing proteins. The stability of pharmaceutical active substances can be positively affected by modification of their structure (internal) or by the addition of suitable excipients (external).

A common method for external stabilization of pharmaceutical active substances is the utilization of suitable excipients. Excipients for stabilizing active substances can be generally grouped into the following categories: Sugar and polyols, amino acids, amines, salts, polymers and tensides.

Sugars and polyols are frequently used as nonspecific stabilizers. In the biological active substances, their stabilizing effect is attributed predominantly to "preferential exclusion" (Xie and Timasheff, 1997, Biophysical Chemistry, 64(1-3), 25-43; Xie and Timasheff, 1997, Protein Science, 6(1), 211-221; Timasheff, 1998, Advances in protein chemistry, 51, 355-432). When selecting sugars for use with biological active substances, reducing sugars are generally avoided. Saccharose and trehalose are used of choice as non-reducing sugars. Other examples of suitable excipients are glucose, sorbitol, glycerol (Boctor and Mehta, 1992, Journal of Pharmacy and Pharmacology, 44 (7), 600-3; Timasheff, 1993, Annual review of biophysics and biomolecular structure, 22, 67-97; Chang et al., 1993, Pharmaceutical Research, 10(10), 1478-83) and mannitol (Hermann et al., 1996, Pharmaceutical Biotechnology, 9 (Formulation, Characterization, and Stability of Protein Drugs), 303-328; Chan et al., 1996, Pharmaceutical Research, 13(5), 756-761). In addition, it is well known that a wide range of polymers have a stabilizing effect on pharmaceutical active substances, predominantly on proteins such as antibodies, for example. Human serum albumin (HAS), frequently used in the past, has very satisfactory stabilizing and aggregation inhibiting properties; however, because of its potential contamination with "blood borne" pathogens, is unsuitable. Of the polymers known to date, hydroxypropyl-β-cyclodextrin (HP-β-CD) has been shown to be particularly suitable, because it also can be safely administered parenterally. Other examples are the higher molecular weight dextrans (18 to 82 kD), PVP, heparin, type A and B gelatin and hydroxyethyl starches (HES), heparin, dextran sulfate, polyphosphoric acid, poly-L-glutamic acid, poly-L-lysine.

Along with sugars and polyols, amino acids can be used alone or in combination with other excipients for stabilizing. Amino acids are used preferably for stabilizing proteins. For example, the addition of histidine, glycine, sodium aspartate (Na-Asp), glutamate and lysine hydrochloride (Lys-HCl) inhibits the aggregation of rhKGF (recombinant human Keratinocyte Growth Factor) in 10 mM of sodium phosphate buffer (pH 7.0) together with 5% mannitol (Zhang et al., 1995, Biochemistry, 34 (27), 8631-41). The combination of amino acids and propylene glycol improves the structural stability of rhCNTF (recombinant human cilliary neurotrophic factor) (Dix et al., 1995, Pharmaceutical Research (Supplement), 12, p. 97). Lysine and arginine increase thermostability of IL-1R (Tm—increase), whereas glycine and alanine have a destabilizing effect (Remmele et al., 1998, Pharmaceutical Research, 15(2), 200-208).

Furthermore, the stability of pharmaceutical active substances is enhanced by different drying processes. Drying is carried out, however, generally also in the presence of excipients, which maintain the stability of the active substances and are intended to improve the properties of the dry powder. A critical factor in stabilization by drying is the immobilization of the active substance in an amorphous matrix. The amorphous state has a high viscosity with low molecular mobility and low reactivity. Thus, advantageous excipients must be capable of forming an amorphous matrix having as high a temperature of vitrification as possible, in which the active substance is imbedded. Accordingly, the choice of excipients depends especially on their stabilization capabilities. Furthermore, factors like the pharmaceutical acceptability of the excipient and its influence on particle formation, dispersibility and flow characteristics, however, play a critical role, especially if it is a spray drying process.

Spray drying represents a particularly suitable process for increasing the chemical and physical stability of peptide/protein analogous pharmaceutical active substances (Maa et al., 1998, Pharmaceutical Research, 15(5), 768-775). Spray drying is being used increasingly especially in the field of pulmonary therapy (U.S. Pat. No. 5,626,874; U.S. Pat. No. 5,972,388; Broadhead et al., 1994, J. Pharm. Pharmacol., 46(6), 458-467), because in the meanwhile administration by inhalation also represents an alternative in the treatment of systemic diseases (WO 99/07340). The pre-requisite is that the mean particle size of the powder is in the range of from 1-10 μm, preferably between 1-7.5 μm, so that the particles can reach the deeper lung sections and consequently reach the blood circulation. DE-A-179 22 07 describes, for example, the manufacture of corresponding spray dried particles. In the meanwhile, a number of processes for manufacturing corresponding powders are described (WO 95/31479; WO 96/09814; WO 96/32096; WO 96/32149; WO 97/41833; WO 97/44013; WO 98/16205; WO 98/31346; WO 99/66903; WO 00/10541; WO 01/13893; Maa et al., 1998, supra; Vidgrén et al., 1987, Int. J. Pharmaceutics, 35, 139144; Niven et al., 1994, Pharmaceutical Research, 11(8), 1101-1109).

Likewise, sugars and their alcohols are suitable as excipients (e.g. trehalose, lactose, saccharose or mannitol) as well as various polymers (Maa et al., 1997, Pharm. Development and Technology, 2(3), 213-223; Maa et al., 1998, supra; Dissertation Adler, 1998, University of Erlangen; Costantino, et al., 1998, J. Pharm. Sci., 87(11), 1406-1411). The predominantly used excipients, however, have different drawbacks. The addition of trehalose and mannitol, for example, adversely affects flow properties of spray dried formulations (C. Bosquillon et al., 2001 Journal of Controlled Release, 70(3), 329-339). Mannitol tends also to recrystallize at a concentration of more than 20% wt (Costantino et al., 1998, supra), whereby stabilizing effects diminish dramatically. Although lactose, a frequently used excipient, improves flow properties of spray dried formulations (C. Bosquillon et al., 2001, supra), it is, however, problematic in the formulation of peptide active substances/active substances containing proteins, because lactose can involve destabilizing Maillard reactions with peptides/proteins because of its reducing characteristic.

In spray drying of antibodies without the addition of stabilizers there is a development of the secondary structure and consequently loss of bioactivity in virtue of regular dehydration, heat and shearing. When this is done, the previously introverted hydrophobic parts of the antibody become extraverted. This occurs to a greater extent at the hydrophobic interfaces between the water droplets arising in the course of spray drying and the air. In addition, antibodies aggregate within the aqueous phase to dimers or higher order aggregates. These aggregations are frequently irreversible. In addition, the high temperature at which the proteins are sprayed represents a critical parameter. In virtue of the high energy application can result in a destabilization of the peptide bonds and in denaturisation of the antibody. Furthermore, there is aggregate formation of spray-dried antibodies during the storage period of the powder. In particular, the residual water content in the powder has negative effects in this case. Protein aggregates are characterized by reduced or absent biological activity and enhanced antigenicity.

Lactosucrose as well multiple sugars (oligosaccharides) designated as coupling sugars with the main components maltosylsucrose and glucosylsucrose are used in the foodstuffs sector. They are used as bulking agents and dispersing agents along with sweeteners like aspartam, as mildly sweet components in chewing gum, for stabilizing against crystallization of trehalose syrups or as so-called NDOs (non-digestible oligosaccharides). An improvement and stabilization of the sweetening quality of asparagyl peptides or of the sweet-sour ratio in drinks containing ballast and sweetener agents is also well-known (US 2003/0059511, EP 1 223 175, DE 199 53 727). U.S. Pat. No. 5,489,577 and EP 0 630 651 further disclose the use of oligosaccharides for stabilizing suspensions comprised of therapeutic proteins and fatty or oil bases. It is stated that the proteins, without pre-mixing with the oligosaccharides would lose their activity at the time of mixing and working with the hydrophobic, semi-solid masses. The stabilization potential over the period of storage in hydrophobic mixtures or in powders is not mentioned at all.

An object of the invention is to provide novel excipients for use in manufacturing pharmaceutical preparations. The corresponding preparations should be characterized inter alia by good long-term stability.

A further object of the present invention is to provide novel excipients for use in manufacturing dried pharmaceutical preparations. The corresponding pharmaceutical preparation in powder form should be characterized by good long-term stability and, if possible, by inhalability.

A further object of the present invention is to provide novel excipients for use in manufacturing peptide pharmaceutical formulations or pharmaceutical formulations containing proteins, in particular for those produced by spray drying. The corresponding peptide pharmaceutical preparation/pharmaceutical preparation containing proteins should be characterized by good long-term stability and, if possible, by inhalability.

A further object of the present invention is to provide novel excipients for use in formulating therapeutic antibodies or antibody derivatives, in particular for those produced by spray drying. The corresponding antibody-containing pharmaceutical preparation should be characterized by good long-term stability and, if possible, by inhalability.

A further object of the present invention is to provide corresponding pharmaceutical preparations for administration by inhalation, whether in the form of a dry powder, a dosing aerosol containing a propellant gas or an inhalation solution not containing a propellant gas.

The objects upon which the invention is based are achieved by means of the following embodiments and by the subject matter/processes represented in the patent claims.

SUMMARY OF THE INVENTION

The present invention relates to spray-dried powder containing a pharmaceutically active substance and one or more 1,4 O-linked saccharose derivatives chosen from the group comprising the compounds: 1,4 O-linked D-gal-saccharose (lactosucrose), 1,4 O-linked D-glu-saccharose (glucosyl sucrose) or 1,4 O-linked glu-glu-saccharose (maltosyl sucrose). Preferred powders contain lactosucrose as the saccharose derivative or a combination of glycosyl and maltosyl sucrose, wherein lactosucrose is particularly preferred.

Furthermore, the term lactosucrose means molecules having the following structural formula:

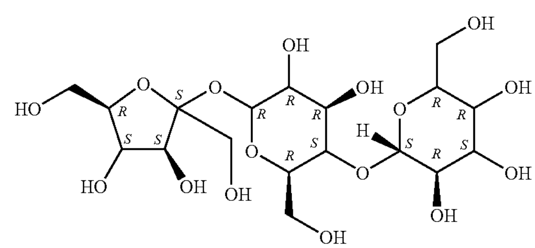

In terms of the present invention, moreover, glucosyl sucrose means molecules having the following structural formula:

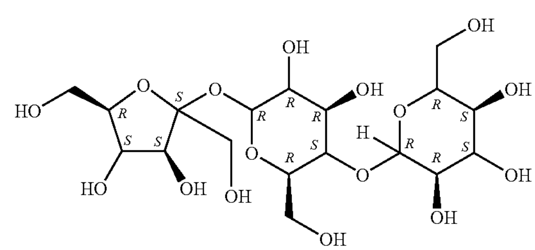

Further, the term maltosyl sucrose means molecules having the following structural formula:

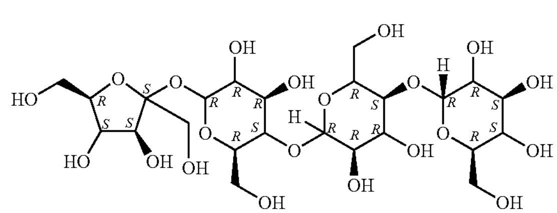

According to a further embodiment of the invention, the corresponding powders contain, along with the 1,4 O-linked saccharose derivative one or more mono-, di- and/or polysaccharides, wherein the additional utilization of mono- and/or disaccharides in manufacturing the powders is preferred. Furthermore, powders comprising a combination of glucosyl and maltosyl sucrose have been shown to be in accord with the invention, preferably in combination with other mono-, di- and/or polysaccharides.

In the case of the pharmaceutical active substance, it is preferably a biological macromolecule that can be a polypeptide or a protein such as growth hormone, an enzyme or an antibody, for example. Particularly in accord with the invention are spray-dried powders with (a) a 25% to 99.99% (w/w) part, preferably 60 to 90% (w/w) of at least one 1,4 O-linked saccharose derivative or of a sugar mixture that contains at least one 1,4 O-linked saccharose-derivative and (b) with a biological macromolecule as the pharmaceutical active substance, preferably in a concentration between 0.01 and 75% (w/w), with reference to the dry mass of the powder, wherein the sum of the weight percents of sugar/sugar mixture and biological macromolecule is not more than 100% (w/w).

It was unexpectedly found that the corresponding powders following their spray drying (i) form an amorphous structure, (ii) occur in a relatively high yield (at least 75% with reference to the solid material used), (iii) have a temperature of vitrification of greater than 40° C. and (iv) have a low tendency towards recrystallization.

The spray-dried powder according to the invention can, in addition to a 1,4 O-linked saccharose derivative or a sugar mixture, that contains at least 1,4 O-linked saccharose derivative, other excipients such as amino acids, peptides, proteins or even other sugars, for example. Particularly advantageous are powders, which in addition to the 1,4 O-linked saccharose derivative or a sugar mixture, which contains at least one 1,4 O-linked saccharose derivative and in addition the pharmaceutical active substance contain at least one amino acid, a peptide, a di-peptide, a tri-peptide and/or a salt. According to a preferred embodiment, the present invention relates to spray-dried powders, which, relative to their dry mass, contain (a) between 25 and 90% (w/w) at least one 1,4 O-linked saccharose derivative or a sugar mixture containing at least one 1,4 O-linked saccharose derivative, (b) between 1 and 39.99% (w/w) at least one amino acid and/or at least one peptide as an additional excipient and (c) at least 0.01% (w/w) of a pharmaceutical active substance. The other excipient is preferably the amino acid isoleucine or a di- or tri-peptide having at least one isoleucine residue. According to a special embodiment, the present invention relates to a spray-dried powder, which, with reference to its dry mass, contains a part of (a) approximately 60 to 80% (w/w) of at least one 1,4 O-linked saccharose derivative or a sugar mixture containing at least 1,4 O-linked saccharose derivative, (b) approximately 10 to 19.99% (w/w) of an amino acid, preferably isoleucine, and (c) approximately 0.01 to 30% (w/w) of a pharmaceutical active substance, preferably a peptide/protein such as an antibody, for example. According to another alternative embodiment, the present invention relates to a spray-dried powder, which, with reference to its dry mass, contains (a) approximately 60 to 90% (w/w) at least of a 1,4 O-linked saccharose derivative or a sugar mixture containing at least one 1,4 O-linked saccharose derivative, (b) approximately 1 to 19.99% (w/w) of an tri-peptide containing isoleucine, preferably tri-isoleucine and (c) approximately 0.01 to 39% (w/w) of a pharmaceutical active substance, preferably a peptide/protein such as an antibody, for example. The corresponding powder, particularly after co-mixing of isoleucine, or tri-peptides containing isoleucine, exhibit very good flow properties and are characterized by a very high proportion of inhalable particles. Furthermore, the corresponding powders have very good process and storage stability.

According to another embodiment, the present invention relates to spray-dried powders, which (a) have one or more 1,4 O-linked saccharose derivative(s) or a sugar mixture containing at least one 1,4 O-linked saccharose derivative and (b) at least one pharmaceutical active substance, wherein the spray-dried powder has a temperature of vitrification of greater than 40° C., preferably greater than 45° C., further preferably greater than 50° C. and more particularly preferred greater than 55° C. and especially preferred greater than 60° C. Conventionally, the corresponding powders according to the invention have a maximum temperature of vitrification of approximately 96 to 110° C. In isolated cases the value can also be higher. In particular, the portion of 1,4 O-linked saccharose derivative or the proportion of the derivative mix in the powder is primarily responsible for the corresponding temperature of vitrification.

According to another embodiment, the present invention relates to pharmaceutical compositions for inhalation applications, which contain one of the powders according to the invention and described hereinbefore or consists of these or is manufactured from these. In this connection, pharmaceutical compositions are preferred, which contain the powder according to the invention as a powder for inhalation, dosing aerosols containing propellant gases or as inhalation solutions not containing propellant gas after reconstitution. The spray-dried powders according to the invention used for manufacturing the pharmaceutical composition are characterized according to a further embodiment by a high proportion of inhalable particles having a mass median aerodynamic diameter (MMAD) of less than 10 µm, preferably 0.5-7.5 µm, further preferred 0.5-5.5 µm, particularly preferred 0.5-5.0 µm.

Furthermore, the invention provides methods for manufacturing the corresponding spray-dried powders according to the invention that are characterized in that a solution or suspension, which (a) contains one or more 1,4 O-linked saccharose derivative(s) or a sugar mixture containing these and (b) at least one pharmaceutical active substance, is manufactured and these are sprayed under suitable conditions. The temperature for the spraying process is preferably between 50 and 200° C. (inlet temperature) and 30 and 150° C. (outlet temperature).

DESCRIPTION OF THE FIGURES

All percentage data specified in the descriptions relate to concentrations of solids in solutions (w/w). All legends in the drawings described below relate to the percentage (w/w) composition of powders achieved by spray drying and freeze drying with ensuing pulverization. The legends further specify the total solids concentrations of solutions (total solids=TS) in percent (w/w). In the legends of FIGS. 19, 20 and 21, tri-isoleucine is abbreviated to Ile3. FIGS. 15, 17, 18, 19, 20 and 21 further specify the atomization rate (AAF=atomizing air flow) set during the spray drying process on the Büchi B-290. The FIG. 40 then corresponds to a real volume flow of ~0.67 m$^3$/h, 50 to a real volume flow of ~1.05 m$^3$/h, and 60 to a real volume flow of ~1.74 m$^3$/h. In all other drawings, the atomization rate of 40 corresponded to a real volume flow of ~0.67 m$^3$/h respectively.

FIG. 1 shows the aggregate formation after freeze drying, pulverization, and one week's open storage at 75% relative humidity and 40° C. (forced storage stability). Aqueous solutions with a) 4.5% LS55P fraction and 0.5% IgG fraction, b) 4.5% Coupling Sugar fraction and 0.5% IgG fraction, c) 5.0% IgG fraction, and d) 4.5% mannitol fraction and 0.5% IgG fraction were freeze dried. Both the LS55P- and Coupling Sugar-containing powders are distinguished by a low aggregate fraction.

FIG. 2 shows the aggregate formation after freeze drying, pulverization, equilibration, and four weeks' dry storage at 40° C. (equilibrated storage stability). Aqueous solutions with a) 4.5% LS55P fraction and 0.5% IgG fraction, b) 4.5% Coupling Sugar fraction and 0.5% IgG fraction, c) 5.0% IgG fraction, and d) 4.5% mannitol fraction and 0.5% IgG fraction were freeze-dried. Both the LS55P- and Coupling Sugar-containing powders are distinguished by a low aggregate fraction.

FIG. 3 shows the aggregate formation after freeze drying, pulverization, vacuum drying, and four weeks' dry storage at 40° C. (vacuum-dried storage stability). Aqueous solutions with a) 4.5% LS55P fraction and 0.5% IgG fraction, b) 4.5% Coupling Sugar fraction and 0.5% IgG fraction, c) 5.0% IgG fraction, and d) 4.5% mannitol fraction and 0.5% IgG fraction were freeze dried. Both the LS55P- and Coupling Sugar-containing powders are distinguished by a low aggregate fraction.

FIG. 4 shows the aggregate formation after spray drying and one week's open storage at 75% relative humidity and 40° C. (forced storage stability). Aqueous solutions with a) 9% LS55P fraction and 1% IgG fraction, b) 9% Coupling Sugar fraction and 1% IgG fraction, c) 9% Coupling Sugar S fraction and 1% IgG fraction, d) 9% trehalose fraction and 1% IgG fraction, and e) 10% IgG fraction were spray-dried. Both the LS55P- as well as the Coupling Sugar- and Coupling Sugar S-containing powders are distinguished by a low aggregate fraction.

FIG. 5 shows the aggregate formation after spray drying and one week's open storage at 75% relative humidity and 40° C. (forced storage stability). Aqueous solutions with a) 8% LS55P fraction, 1% isoleucine fraction, and 1% IgG fraction, b) 8% Coupling Sugar fraction, 1% isoleucine fraction, and 1% IgG fraction, c) 8% Coupling Sugar S fraction, 1% isoleucine fraction, and 1% IgG fraction, d) 8% trehalose fraction, 1% isoleucine fraction, and 1% IgG fraction, and e) 10% IgG fraction were spray-dried. Both the LS55P- as well as the Coupling Sugar- and Coupling Sugar S-containing powders are distinguished by a low aggregate fraction.

FIG. 6 shows the aggregate formation after spray drying and one week's open storage at 75% relative humidity and 40° C. (forced storage stability). Aqueous solutions with a) 3% LS55P fraction, 6% citrulline fraction, and 1% IgG fraction, b) 3% Coupling Sugar fraction, 6% citrulline fraction, and 1% IgG fraction, c) 3% Coupling Sugar S fraction, 16% citrulline fraction, and 1% IgG fraction, d) 3% trehalose fraction, 6% citrulline fraction, and 1% IgG fraction, and e) 10% IgG fraction were spray-dried. Both the LS55P- as well as the Coupling Sugar- and Coupling Sugar S-containing powders are distinguished by a low aggregate fraction.

FIG. 7 shows the aggregate formation after spray drying and one week's open storage at 75% relative humidity and 40° C. (forced storage stability). Aqueous solutions with a) 9.9% LS55P fraction and 0.1% IgG fraction, b) 9% LS55P fraction and 1% IgG fraction, c) 6% LS55P fraction and 4% IgG fraction, d) 4% LS55P fraction and 6% IgG fraction, e) 2.5% LS55P fraction and 7.5% IgG fraction, f) 9% LS55P fraction and 1% IgG fraction, g) 0.5% LS55P fraction and 9.5% IgG fraction, and h) 10% IgG fraction were spray-dried. The LS55P-containing powders are distinguished by a low aggregate fraction.

FIG. 8 shows the aggregate formation after spray drying and one week's open storage at 75% relative humidity and 40° C. (forced storage stability). Aqueous solutions with a) 9.9% Coupling Sugar fraction and 0.1% IgG fraction, b) 9% Coupling Sugar fraction and 1% IgG fraction, c) 6% Coupling Sugar fraction and 4% IgG fraction, d) 4% Coupling Sugar fraction and 6% IgG fraction, e) 2.5% Coupling Sugar fraction and 7.5% IgG fraction, f) 1% Coupling Sugar fraction and 9% IgG fraction, and g) 10% IgG fraction were spray-dried. The LS55P-containing powders are distinguished by a low aggregate fraction.

FIG. 9 shows the aggregate formation after spray drying and one week's open storage at 75% relative humidity and 40° C. (forced storage stability). Aqueous solutions with a) 3.00% LS55P fraction and 0.33% IgG fraction, b) 2.9166% LS55P fraction, 0.0833% tri-isoleucine fraction, and 0.33% IgG fraction, c) 2.833% LS55P fraction, 0.166% tri-isoleucine fraction, and 0.33% IgG fraction, and d) 2.66% LS55P fraction, 0.33% tri-isoleucine fraction, and 0.33% IgG fraction were spray-dried. The LS55P-containing powders are distinguished by a low aggregate fraction. Protein aggregation is further significantly reduced by an increase in the tri-isoleucine fraction from 0% to 10% in relation to the total solids content of the LS55P-containing powders.

FIG. 10 shows the aggregate formation after spray drying and one week's open storage at 75% relative humidity and 40° C. (forced storage stability). Aqueous solutions with a) 3.00% LS90P fraction and 0.33% IgG fraction, b) 2.9166% LS90P fraction, 0.0833% tri-isoleucine fraction, and 0.33% IgG fraction, c) 2.833% LS90P fraction, 0.166% tri-isoleucine fraction, and 0.33% IgG fraction, and d) 2.66% LS90P fraction, 0.33% tri-isoleucine fraction, and 0.33% IgG fraction were spray-dried. The LS90P-containing powders are distinguished by a low aggregate fraction.

FIG. 11 shows the aggregate formation after spray drying and one week's open storage at 75% relative humidity and 40° C. (forced storage stability). Aqueous solutions with a) 2.66% LS90P fraction, 0.33% tri-isoleucine fraction, and 0.33% IgG fraction, b) 2.66% LS55P fraction, 0.33% tri-isoleucine fraction, and 0.33% IgG fraction, c) 2.66% saccharose fraction, 0.33% tri-isoleucine fraction, and 0.33% IgG fraction, d) 2.00% saccharose fraction, 0.66% lactose fraction, 0.33% tri-isoleucine fraction, and 0.33% IgG fraction, e) 2.66% raffinose fraction, 0.33% tri-isoleucine fraction, and 0.33% IgG fraction, f) 2.66% hydroxyethyl starch (HES) fraction, 0.33% tri-isoleucine fraction, and 0.33% IgG fraction, and g) 2.66% trehalose fraction, 0.33% tri-isoleucine fraction, and 0.33% IgG fraction were spray-dried. The LS90P- and LS55P-containing powders are distinguished by a low aggregate fraction, particularly in comparison with raffinose and hydroxyethyl starch (HES) specified as state-of-the-art.

FIG. 12 shows the aggregate formation after spray drying and vacuum drying, four weeks' dry storage at 40° C. (vacuum-dried storage stability). Aqueous solutions with a) 9% Coupling Sugar fraction and 1% IgG fraction, b) 8% Coupling Sugar fraction, 1% (w/w) isoleucine fraction, and 1% IgG fraction, c) 3% Coupling Sugar fraction, 6% citrulline fraction, and 1% IgG fraction, and d) 10% IgG fraction were spray-dried. The Coupling Sugar-containing powders are distinguished by a low aggregate fraction.

FIG. 13 shows the aggregate formation after spray drying and vacuum drying, four weeks' dry storage at 40° C. (vacuum-dried storage stability). Aqueous solutions with a) 9.9% LS55P fraction and 0.1% IgG fraction, b) 9% LS55P fraction and 1% IgG fraction, c) 2.5% LS55P fraction and 7.5% IgG fraction, d) 1% LS55P fraction and 9% IgG fraction, e) 10% IgG fraction, f) 8% LS55P fraction, 1% isoleucine fraction, and 1% IgG fraction, and g) 3% LS55P fraction, 6% citrulline fraction, and 1% IgG fraction were spray-dried. The LS55P-containing powders are distinguished by a low aggregate fraction.

FIG. 14 shows the aggregate formation after spray drying and vacuum drying, one month's dry storage at 2-8° C., 25° C., and 40° C. (1 month's stability). Aqueous solutions with a) 3.00% LS90P fraction and 0.33% IgG fraction and b) 2.66% LS90P fraction, 0.33% isoleucine fraction, and 0.33% IgG fraction and c) 2.66% LS90P fraction, 0.33% tri-isoleucine fraction, and 0.33% IgG fraction were spray-dried. The powders containing LS90P powders are distinguished by a particularly low aggregate fraction after one month's storage.

FIG. 15 shows the aggregate formation after spray drying and open dry storage for one month at 29% relative humidity and 43% relative humidity at 25° C. respectively (open 1 month stability). Aqueous solutions with a) 2.9166% LS90P fraction, 0.0833% tri-isoleucine fraction and 0.33% IgG fraction at an AAF of 40, b) 2.833% LS90P fraction, 0.166% tri-isoleucine fraction, and 0.33% IgG fraction at an AAF of 40, c) 1.60% LS90P fraction, 0.20% tri-isoleucine fraction, and 0.33% IgG fraction at an AAF of 40, d) 2.66% LS90P fraction, 0.33% tri-isoleucine fraction, and 0.33% IgG fraction at an AAF of 50, and e) 2.66% LS90P fraction, 0.33% tri-isoleucine fraction, and 0.33% IgG fraction at an AAF of 60 were spray-dried. The LS90P-containing powders are distinguished by a particularly low aggregate fraction after one month's storage.

FIG. 16 shows the aggregate formation after spray drying, vacuum drying and open dry storage for three months at 2-8° C., 25° C. and 40° C. (3 month stability). Aqueous solutions with a) 2.66% LS55P fraction, 0.33% tri-isoleucine fraction and 0.33% IgG fraction and b) 2.66% LS55P fraction, 0.33% isoleucine fraction and 0.33% IgG fraction were spray-dried. The LS55P-containing powders are distinguished by a particularly low aggregate fraction after three months' storage.

FIG. 17 shows the fine particle fraction (FPF) with a cut-off diameter smaller than 5 μm for various powders. The powders were produced by spray drying of aqueous solutions which have contained LS55P and IgG1 or LS55P, isoleucine and IgG1. The solutions were produced and sprayed as described under EXAMPLES. Isoleucine-containing powder has a FPF of ~35%, whereas isoleucine-free powder only has a FPF of ~16%.

FIG. 18 shows the fine particle fraction (FPF) with a cut-off diameter smaller than 5 μm for various powders. The powders were produced by spray drying of aqueous solutions which have contained LS90P and IgG1 or LS90P, is leucine and IgG1. The solutions were produced and sprayed as described under EXAMPLES. Isoleucine-containing powder has a FPF of ~28%, whereas isoleucine-free powder has a FPF of ~23%.

FIG. 19 shows the fine particle fraction (FPF) with a cut-off diameter smaller than 5 μm for various powders. The powders were produced by spray drying of aqueous solutions which have contained LS55P and IgG1 or LS55P, tri-isoleucine and IgG1. The solutions were produced and sprayed as described under EXAMPLES. Tri-isoleucine-containing powders have a FPF of more than 50 or 58%, whereas tri-isoleucine-free powder only has a FPF of ~16%.

FIG. 20 shows the mass mean aerodynamic diameter (MMAD) and mass mean diameter (MMD) of various powders. The powders were produced by spray drying of aqueous solutions which have contained LS55P and IgG1 or LS55P, tri-isoleucine and IgG1. The solutions were produced and sprayed as described under EXAMPLES. All powders have a MMAD smaller than 5 μm and a MMD smaller than 3.5 μm. The diagram shows the effect of the tri-isoleucine fraction at constant total solids concentrations and spraying parameters on the MMAD and MMD. A 10% tri-isoleucine fraction related to the total solids content of the formulation significantly reduces the MMAD.

FIG. 21 shows the fine particle fraction (FPF) with a cut-off diameter smaller than 5 μm for various powders. The powders were produced by spray drying of aqueous solutions which have contained LS90P and IgG1 or LS90P, tri-isoleucine and IgG1. The solutions were produced and sprayed as described under EXAMPLES. Tri-isoleucine-containing powders have a FPF of ~40% to ~59%, whereas tri-isoleucine-free powder only has a FPF of ~24%.

FIG. 22 shows the mass mean diameter (MMD) and mass mean aerodynamic diameter (MMAD) of various powders. The powders were produced by spray drying of aqueous solutions which have contained LS90P and IgG1 or LS90P, tri-isoleucine and IgG1. The solutions were produced and sprayed as described under EXAMPLES. All powders have a MMAD smaller than 6.5 μm and a MMD smaller than 5 μm. The diagram shows the effect of the tri-isoleucine fraction at constant total solids concentrations and spraying parameters on the MMAD and MMD. A 10% tri-isoleucine fraction related to the total solids content of the formulation significantly reduces the MMAD. Both a lower solids content (e.g. TS: 2%) and a higher spraying pressure (AAF of 50 or 60), however, significantly educe the MMD.

FIG. 23 shows an inhaler for application of dry powder preparations by inhalation.

DETAILED DESCRIPTION OF THE INVENTION

Definitions

In the context of the description of the invention, terms and designations used shall have the meanings hereinafter defined. The weight and weight percent statements refer, unless otherwise mentioned, to the dry mass of the powder or to the solids content of the dried solutions/suspensions. The general embodiments "containing" or "contains" includes the particular embodiment "comprised of". Furthermore, "singular" and "plural" are not used by way of limitation.

The expression "1,4 O-linked saccharose derivative or a sugar mixture containing at least one 1,4 O-linked saccharose derivative" is defined as (i) a 1,4 O linked saccharose derivative, preferably having a formula stated in this patent, (ii) a mixture thereof, preferably a mixture comprised of maltosyl and glycosyl sucrose, (iii) a mixture of at least one 1,4 O-linked saccharose derivative having one of the formulas stated hereinbefore and other sugars, preferably a mixture of lactosucrose, lactose and saccharose or comprised of glucosyl and/or maltosyl sucrose, saccharose, fructose and glucose, (iv) a mixture comprised of at least 55% (w/w) lactosucrose, a maximum of 25% (w/w) lactose and a maximum of 10% (w/w) saccharose, (v) a mixture comprised of at least 88% (w/w) lactosucrose, a maximum of 10% (w/w) lactose and saccharose (vi) a mixture comprised of at least 25% (w/w) glucosyl and/or maltosyl sucrose, between 48% and 56% (w/w) saccharose and/or more than 10% (w/w) glucose and fructose, (vii) a mixture comprised of 18% (w/w) each of glucosyl and maltosyl sucrose, between 11% and 15% (w/w) saccharose and between 5% an 9% (w/w) glucose, (viii) a sugar mixture designated as Nyuka-Oligo® LS40L (abbreviated LS40L), Nyuka-Oligo® LS55L (abbreviated LS55L), Nyuka-Oligo® LS55P (abbreviated LS55P), Nyuka-Oligo® LS-90P (abbreviated LS90P), Coupling Sugar® or Coupling Sugar S® (Hayashibara Shoji, Inc., Japan).

The expression "spray dried powder formulation" or "dry powder fomulation" are defined as powder formulations that conventionally have less than approximately 10% (w/w) residual moisture, preferably less than 7% (w/w) residual moisture, in particular preferably less than 5% (w/w) residual moisture and even more preferably less than 3% (w/w) residual moisture. The residual moisture, at constant spray, vacuum or freeze drying conditions and identical excipients, essentially dependent on the type and proportion of the pharmaceutical active substance in the powder formulation.

The term "amorphous" is defined as a powder formulation containing less than 10% crystalline moieties, preferably less than 7%, further preferably less than 5%, and in particular less than 4, 3, 2 or 1%.

The term or "inhalable" is defined as a powder that is suitable for pulmonary applications. Inhalable powders can be dispersed using an inhaler and inhaled so that the particles reach the lungs and, if necessary, via the alveoli develop a systemic effect. Inhalable particles have, for example, a mean particle size of between 0.4-10 µm (MMD=mass median diameter), generally between 0.5-5 µm, preferably between 1-3 µm and/or a mass median aerodynamic diameter (MMAD=mass median aerodynamic diameter) of between 0.5-10 µm, preferably between 0.5-7.5 µm, further preferably between 0.5-5.5 µm, more preferably 1-5 µm and in particular preferably between 1-4.5 µm.

"Mass median diameter" or "MMD" is a measurement for the average particle size distribution, because the powder of the invention are generally polydispersed. The results are expressed as the diameter of the total volume distribution at 50% total throughput The MMD values can be determined, for example, by means of laser diffractometry (in this connection see: EXAMPLES section, Methods), whereby, of course, any other conventional method can be used (e.g. electron microscopy, centrifuge sedimentation).

The term "mass median aerodynamic diameter (MMAD)" states the aerodynamic particle size, at with 50% of the particles of the powder normally have a small aerodynamic diameter. In the event of uncertainty, the methods given in this patent (in this connection see EXAMPLES section, Methods) serve as the reference method for determining the MMAD.

The term "fine particle fraction" (FPF) describes the inhalable part of a powder consisting of particles having a particle size of $\leqq 5$ µm MMAD. In powders that can be satisfactorily inhaled, the FPF is greater than 20%, preferably more than 30%, in particular preferably more than 40%, even more preferred more than 50% and still further preferred more than 55%. The term "cut-off diameter" used in this context states which particles are taken into account when determining the FPF. An FPF of 30% at a cutoff diameter of 5 µm ($FPF_5$) means that at least 30% of all particles in the powder have a mass median aerodynamic diameter of less than 5 µm.

The term "spray solution" is defined as an aqueous solution or suspension, in which the pharmaceutical active substances is dissolved/suspended together with at least one excipient.

The term "time of flight" is the designation for a standard measurement method as is more completely described in the EXAMPLES section. In a time of flight measurement, the MMAD and FPF are measured simultaneously (in this connection see the EXAMPLES section, Methods).

The term "pharmaceutically acceptable excipient", "vehicle" or "matrix" refers to excipients, that can be included optionally in the formulation in the context of the invention. The excipients can, for example, be pulmonary administered without having significant adverse toxicological effects on the test subject or the test subject's lung.

The term "pharmaceutically acceptable salts" includes by way of example the following salts but is not limited thereto: Salts of inorganic acids such as chloride, sulfate, phosphate, diphosphate, bromide and nitrate salts. In addition, salts of organic acids such as malate, maleate, fumarate, tartrate, succinate, ethylsuccinate, citrate, acetate, lactate, methanesulfonate, benzoate, ascorbate, para-toluolsulfonate, palmoate, saliscylate and stearate, as well as estolate, gluceptate and lactobionate salts.

The term "pharmaceutically acceptable cations" includes, but not by way of limitation, for example, lithium, sodium, potassium, calcium, aluminum and ammonium (including substituted ammonium).

The term "polysaccharide" or "oligosaccharide" is defined as a multiple sugar comprised of at least three sugar residues.

A "pharmaceutically active substance" is defined as a substance, a medicinal product, a composition or a combination hereof, which has a generally positive pharmacological effect on the organism, an organ and/or a cell, when the active substance is brought into contact with the organism, organ or cell. When administered to a patient, it can have a local or a systemic effect.

The term "biological macromolecule" is defined as a peptide, protein, fat, fatty acid or also a nucleic acid.

The term "peptide" or "polypeptide" is defined as a polymer of amino acids comprised of from two to one hundred amino acid residues. The term peptide or polypeptide is used as an alias and includes both homopeptides and heteropeptides; that is, polymers of amino acids comprised of identical or different amino acid residues. Accordingly, a "dipeptide" is built from two peptide-linked amino acids, a "tri-peptide" form three peptide-linked amino acids. The term "protein" as used herein is a polymer of amino acids having more than 100 amino acid residues.

The term "analogue" is used to characterize a peptide/protein, in which single or multiple amino acids were substituted, eliminated (e.g. fragments), added (e.g. derivatives with a C- or N-terminal extension) or otherwise modified with respect to the native (wild type) sequence. Likewise, preparation of derivatives of the native protein such as, for example, by means of sugars, polyethylene glycol or the like is also possible. Analogues have a bioactivity of at least 10, 20, 30 or 40%, preferably of at least 50, 60 or 70% and particularly preferably of at least 80, 90, 95, 100% or more than 100% bioactivity of the native, non-synthetic protein.

The term "amino acid" is defined as a compound, which contains at least one amino and at least one carboxyl group. Although the amino group is conventionally in the $\alpha$ position relative to the carboxyl group, any other arrangement in the molecule is also conceivable. The amino acid can also contain other functional groups such as amino-, carboxamide-, carboxyl-, imidazol-, thio-groups and other groups, for example. Naturally occurring or synthetic amino acids, racemate or enantiomer (D- or L-), including different stereoisomeric proportions, can be used. For example, the term isoleucine comprises both D-isoleucine, L-isoleucine, racemic isoleucine and different proportions of the two enantiomers.

The term "pure protein formulation" is defined as spray-dried powder consisting of one or more of proteins and optionally one suitable buffer (typically from 0 to 15% (w/w) relative to the weight of the dried powder).

The powder basically contains no other excipients; that is, the content in any other excipients is less than 1% (w/w) relative to the weight of the dried powder.

A "surface active" substance is capable of reducing the surface tension of the solution, in which it is dissolved. The surface activity is measured using the tensiometer method after Lecomte du Noüy (Bauer, Fromming, Führer, $6^{th}$ ed.), for example.

The Powder According to the Invention

The present invention relates to a spray-dried powder containing a pharmaceutical active substance and one or more 1,4 O-linked saccharose derivative(s) selected from the group comprising: 1,4 O-linked D-gal-saccharose (lactosucrose), 1,4 O-linked D-glu-saccharose (glucosyl sucrose) or a 1,4 O-linked glu-glu-saccharose (maltosyl sucrose).

According to a further embodiment of the invention, the corresponding powders contain, along with the 1,4 O-linked saccharose derivative one or more mono-, di- and/or polysaccharides, wherein the additional utilization of mono- and/or disaccharides in manufacturing the powders is preferred. Accordingly, the invention comprises also corresponding powders containing lactosucrose, lactose and saccharose, wherein the portion of lactosucrose relative to the total sugar proportion in the powder is ≧40% (w/w), preferably ≧55% (w/w) and even ≧88% (w/w). According to a preferred embodiment, the powders according to the invention contain, along with the pharmaceutical active substance, a sugar mixture designated Nyuka-Oligo®LS55P (Hayashibara Shoji, Inc., Japan), abbreviated LS55P, which contains at least 55% lactosucrose, a maximum of 25% (w/w) of lactose and a maximum of 10% (w/w) saccharose. According to a preferred embodiment, the powders according to the invention contain, along with the pharmaceutical active substance, a sugar mixture designated Nyuka-Oligo® LS90P (Hayashibara Shoji, Inc., Japan), abbreviated LS90P, which contains at least 88% lactosucrose, a maximum of 10% (w/w) of lactose and saccharose.

Furthermore, powders comprising a combination of glucosyl and maltosyl sucrose have been shown to be in accord with the invention, preferably in combination with other mono, di- and/or polysaccharides. Accordingly, the present invention includes also corresponding powders, that contain a mixture of glucosyl- and maltosyl-sucrose, saccharose, glucose and/or fructose, wherein the proportion of glucosyl- and maltosyl-sucrose relative to the total sugar proportion in the powder is preferably 25% (w/w) or more. According to a further preferred embodiment, the respective proportion of glucosyl- and maltosyl-sucrose is at least 18% (w/w) of the total sugar proportion of the powder. According to a preferred embodiment the spray-dried powders according to the invention containing, in addition to the pharmaceutical active substance, a sugar mixture designated as Coupling Sugar® (Hayashibara Shoji, Inc., Japan), which contains at least 18% (w/w) of glucosyl- and maltosyl sucrose, between 11 and 15% (w/w) of saccharose and between 5 and 9% (w/w) of each of glucose and fructose. Furthermore, the present invention relates also to spray-dried powders, which contain in addition to the pharmaceutical active substance a sugar mixture designated as Coupling Sugar S® (Hayashibara Shoji, Inc., Japan), which contains at least 25% (w/w) glucosyl- and/or maltosyl-sucrose, between 48 and 56% (w/w) of saccharose and not more than 10% (w/w) of glucose and fructose.

Spray-dried powders have been shown to be particularly advantageous, whose proportion of 1,4 O-linked saccharose derivative or of a sugar mixture containing at least 1,4 O-linked saccharose derivative relative to the dry mass of the powder between 25 and 99.99% (w/w), preferably between 60 and 99% (w/w), even more preferred between 70 and 90% (w/w) and ever further preferred is between 80 and 90% (w/w), for example 25, 25.1, 25.2, 25.3, . . . 25.7, 25.8, 25.9 etc.; 26, 27, 28, 29, 30 etc.; 31, 32, 33, . . . 38, 39, 40 etc.; 41, 42, 43, . . . 48, 49, 50 etc.; 51, 52, 53, . . . 58, 59, 60 etc.; 61, 62, 63, . . . 68, 69, 70 etc.; 71, 72, 73, . . . 78 ,79, 80, etc.; 81, 82, 83, . . . 88, 89, 90 etc.; 91, 92, 93, . . . 98, 99, etc.; 99.1, 99.2, 99.3, . . . 99.8, 99.9, etc.; 99.91, 99.92, 99.93, . . . 99.98, 99.99% (w/w). In connection with the use of LS55P or also of LS90P a proportion of 80-90% (w/w) has been shown to be particularly advantageous. Overall, the proportion of 1,4 O-linked saccharose derivative or of a sugar mixture containing at least one 1,4 O-linked saccharose derivative should be chosen, so that the spray-dried powder is at least partially amorphous, preferably completely amorphous. The proportion of 1,4 O-linked saccharose derivative or of a sugar mixture containing at least one 1,4 O-linked saccharose derivative can be reduced also to under 60% (w/w). In this case further stabilizing excipients are added in appropriate quantity to the powders. Examples of other stabilizing excipients can be found elsewhere in this patent specification.

The proportion of pharmaceutical active substance in the dry mass of the powder according to the invention is as a rule between 0.01 and 75% (w/w), preferably between 0.33 and 50% (w/w), further preferred between 0.33 and 45% (w/w), and even further preferred between 0.33 and 40% (w/w). According to a further preferred embodiment, the proportion of the pharmaceutical active substance in the solid content of the powder according to the invention is between 0.33 and 35% (w/w), preferably between 0.33 and 30% (w/w), further preferred between 0.33 and 25% (w/w) and even further preferred between 0.33 and 10% (w/w). Consequently, the proportion is, for example, 0.01, 0.02, 0.03 . . . 0.08, 0.09, etc.; 0.1, 0.2, 0.3, . . . 0.8 0.9 etc.; 1, 2, 3, . . . 8, 9, 10 etc.; 11, 12, 13, . . . 18, 19, 20 etc.; 21, 22, 23, . . . 28, 29,30 etc.; 31, 32, 33, . . . 38, 39, 40 etc.; 41, 42, 43, . . . 48, 49, 50 etc.; 51, 52, 53, . . . 58, 59, 60 etc.; 61, 62, 63, . . . 68, 69, 70 etc.; 71, 72, 73, 74, 74.1, 74.2, 74.3, . . . 74.8, 74.9, etc.; 74.91, 74.92, 74.93, . . . 74.98, 74.99, 75% (w/w).

Consequently, powders are according to the invention that have a proportion of 1,4 O-linked saccharose derivative or a sugar mixture containing at least one 1,4 O-linked saccharose derivative relative to active substance of, for example, 25/75, 26/74, 27/73, 28/72, 29/71, 30/70, 31/69, 32/68, 33/67, 34/66, 35/65, 36/64, 37/63, 38/62, 39/61, 40/60, 41/59, 42/58, 43/57, 44/56, 45/55, 46/54, 47/53, 48/52, 49/51, 50/50, 51/49, 52/48, 53/47, 54/46, 55/45, 56/44, 57/43, 58/42, 59/41, 60/40, 61/39, 62/38, 63/37, 64/36, 65/35, 66/34, 67/33, 68/32, 69/31, 70/30, 71/29, 72/28, 73/27, 74/26, 75/25, 76/24, 77/23, 78/22, 79/21, 80/20, 81/19, 82/18, 83/17, 84/16, 85/15, 86/14, 87/13, 88/12, 89/11, 90/10, 91/9, 92/8, 93/7, 94/6, 95/5, 96/4, 97/3, 98/2, 99/1, 99.1/0.9, 99.2/0.8, 99.3/0.7, 99.4/0.6, 99.5/0.5, 99.6/0.4, 99.66/0.33, 99.7/0.3, 99.8/0.2, 99.9/0.1, 99.99/0.01 (w/w). If the corresponding powder contains one or more additional excipients, then either the proportion of the 1,4 O-linked saccharose derivative or the sugar mixture containing at least one 1,4 O-linked saccharose derivative, the proportion of pharmaceutical active substance or both moieties can be appropriately reduced, whereby the proportion of 1,4 O-linked saccharose derivative or the sugar mixture containing at least one 1,4 O-linked saccharose derivative relative to the dry mass of the powder, preferably has one of the values between 80 and 90% (w/w).

Pharmaceutical active substances for the purposes of the invention are, in addition to those included in the general definition inter alia antibiotics, anti-viral active substances, anti-epileptics, analgesics, anti-inflammatory active substances or bronchodilators. In addition, active substances are included here, which by way of example act on the peripheral nervous system, on the adrenergic receptors, cholinergic receptors, the skeletal musculature, the cardiovascular system, the smooth musculature, the blood circulating system, on synaptic sites, neuroeffector connection sites, the endocrine system, the immune system, the reproductive system, the skeletal system, the autacoid systems, the alimentary and excretory systems, the histamine system and the central nervous system. Suitable active substances further include, for example, hypnotics and sedatives, psychical energizers, tranquilizers, anti-convulsants, muscle relaxants, anti-Parkinsonism active substances, analgesics, anti-inflammatory active substances, muscle contractants, anti-microbial active substances, hormonal active substances such as for example, contraceptives, sympathomimetics, diuretics, active substances regulating lipid metabolism, anti-androgenic active substances, antiparasitic agents, neoplastic agents, anti-neoplastic agents and hypoglycemic agents.

Furthermore, the term pharmaceutical active substance includes also those active substances that have an effect on the respiratory system such as, for example, against one of the following disorders: asthma, chronic obstructive pulmonary diseases (COPD), emphysematic chronic bronchitis, bronchopulmonary dysplasia (BPD), neonatal respiratory distress syndrome (RDS), bronchiolitis, croup, post-extubation stridor, pulmonary fibrosis, pneumonia or cystic fibrosis (CF).

Representative examples of bronchodilators include inter alia beta agonists, anticholinergics or methylxanthine Examples of anti-inflammatory active substances are steroids, cromolyn, nedokromil and leukotriene inhibitors. Examples of steroids include beclomethasone, betamethasone, beclomethasone, dexamethasone, triamcinolone, budesonide, butixocort, ciclesonide, flutikasone, flunisolide, icomethasone, mometasone, tixocortol and loteprenol. Other examples are budesonide, fluticasone propionate, beclomethasone dipropionate, fometerol and trimcinolone acetonide.

Examples of anti-microbially active substances are erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, and azithromycin and swinolide A; fluoroquinolones, for example: ciprofloxacin, ofloxacin, levofloxacin, trovafloxacin, alatrofloxacin, moxifloxicin, norfloxacin, eoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin and sitafloxacin; aminoglykosides such as, for example, gentamicin, netilmicin, paramecin, tobramycin, amikacin, kanamycin, neomycin; streptomycin, vancomycin, teicoplanin, rampolanin, mideplanin, colistin, daptomycin, gramicidin, colistimethate; polymixines such as, for example, polymixin B, capreomycin, bacitracin, peneme, penicillin including penicillinase-sensitive active substances such as penicillin G, penicillin V, penicillinase-resistant active substances such as methicillin, oxacillin, cloxacillin, dicloxacillin, floxacillin, nafcillin; active substances against gram-negative bakteria such as ampicillin, amoxicillin, hetacillin, cillin, and galampicillin; anti-pseudomonal penicillin such as carbenicillin, ticarcillin, azlocillin, mezlocillin, andpiperacillin; cephalosporine such as cefpodoxim, cefprozil, ceftbuten, ceftizoxime, ceftriaxon, cephalothin, cephapirin, cephalexin, cephradrin, cefoxitin, cefamandol, cefazolin, cephaloridin, cefaclor cefadroxil, cephaloglycine, cefuroxim, ceforanide, cefotaxim, cefatrizine, cephacetril, cefepim, cefixim, cefonizide, cefoperazone, cefotetane, cefinetazol, ceftazidim, loracarbef and moxalactam; monobaktams such as aztreonam; and carbapenemes such as, for example, imipeneme, meropeneme pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors and pharmaceutically utilizable salt forms and the like thereof.

In the case of the pharmaceutical active substance, it is a biological macromolecule according to another embodiment. According to the definition stated hereinbefore, for example, peptides, proteins, fats, fatty acids or also nucleic acids are included herein.

Biopharmaceutically important proteins/polypeptides include but not by way of limitation, for example, antibodies, enzymes, growth factors such as, for example, steroids, cytokines, lymphokines, adhesion molecules, receptors and their derivatives or fragments. In general, all polypeptides are important, which act as agonists or antagonists and/or are used therapeutically or diagnostically.

Suitable peptides or proteins in terms of the invention are, for example, insulin, insulin-like growth factor, human growth hormone (hGH) and other growth factors, tissue plasminogen activator (tPA), erythropoietin (EPO), cytokine, for example, interleukins (IL) like IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN)-alpha, beta, gamma, omega or tau, tumor necrose factor (TNF) such as, for example, TNF-alpha, beta or gamma, TRAIL, G-CSF, GM-CSF, M-CSF, MCP-1 and VEGF. Further examples are monoclonal, polyclonal, multi-specific and single-chain antibodies and fragments thereof such as, for example, Fab, Fab', F(ab')$_2$, Fc and Fc'-fragments, light (L) and heavy (H) immunoglobin chains and their constant, variable or hypervariable regions and Fv and Fd fragments (Chamov et al., 1999, Antibody Fusion Proteins, Wiley-Liss Inc.). The antibodies can be of human or non-human origin. For example, the classes known in man are included here: IgA, IgD, IgE, IgG and IgM, with their different subclasses, for example: IgA1, IgA2 and IgG1, IgG2, IgG3 and IgG4. Included also are humanized and chimeric antibodies. Of particular therapeutic significance and accordingly subject matter of the present invention are the powder formulations, that are antibodies against different surface antigens such as CD4, CD20 or CD44, different cytokines such as IL2, IL4 or IL5, for example. Other examples are antibodies against specific immunoglobulin classes (e.g. anti-IgE antibodies) or against viral proteins (e.g. anti-RSV, anti-CMV antibodies, etc.).

Fab fragments (fragment antigen-binding=Fab) consist of the variable regions of both chains, which are held together by the adjacent constant regions. Other antibody fragments are F(ab')$_2$ fragments, which can be produced by proteolytic digestion with pepsin. Shortened antibody fragments can be produced by gene cloning; these fragments consist of only the variable regions of the heavy (VH) and the light (VL) chains. These are designated Fv fragments (fragment variable=fragment of the variable part). Such antibody fragments are also designated as single-chain Fv fragments (scFv). Examples of scFv antibodies are well-known and have been described; see, e.g., Huston et al, 1988, Proc. Natl. Acad. Sci. USA, 16, 5879ff.

In the past, different strategies have been developed, in order to produce multimeric scFv derivatives such as dia-, tri- and pentabodies, for example. A bivalent homodimeric scFv derivative is designated by the specialist in the art as a "diabody". Shortening of the peptide linker in the scFv molecule to 5-10 amino acids results in the formation of homodimers by overlapping of VH/VL chains. In addition, the diabodies can be stabilized by the incorporation of disulfide bridges. Examples of diabodies can be found in the literature; e.g. in Perisic et al., 1994 (Structure, 2, 1217ff). A bivalent homodimeric scFv derivative is designated by the specialist in the art as a "minibody".

It consists of a fusion protein that contains the CH3 region of an immunoglobin, preferably IgG, in particular preferably IgG1, as the dimerization region. This connects the scFv fragments via a hinge region, also from IgG, and a linker legion. Examples of such minibodies are described in Hu et al., 1996, Cancer Res., 56, 3055ff. The specialist in the art designates a trivalent homotrimer scFv derivative as a "tribody" (Korff et al., 1997, Protein Engineering, 10, 423ff). A direct fusion of VH-VL without the use of a linker sequence results in the formation of trimers.

In the fragments called mini-antibodies by the specialist in the art, which have a bi-, tri- or tetravalent structure, are also derivatives of scFv fragments. In this case, the multimerization is obtained using di-, tri- or tetramers "coiled coil" structures (Pack, P. et al., 1993, Biotechnology, 11, 1271ff; Lovejoy, B. et al., 1993, Science, 259, 1288ff; Pack, P. et al., 1995, J. Mol. Biol., 246, 28ff).

A particularly preferred embodiment of the invention includes a protein from the class of the antibody; more precisely immunoglobulin G type I. In this case, it is a humanized monoclonal antibody having 95% human and 5% murine antibody sequences. The antibody has a molecular weight of approximately 148 kilodaltons (kDa), consisting of two light and two heavy chains and a total of four disulfide bridges.

Particularly advantageous are spray-dried powders, which contain a peptide or protein or a peptide/peptide, peptide/protein or protein/protein combination as the active substance. The corresponding biological macromolecules can make up between 0.01 to 75% (w/w), preferably between 0.01 to 50% (w/w) of the dry mass of the powder. Consequently, the proportion is, for example, 0.01, 0.02, 0.03 ... 0.08, 0.09, 0.1, 0.2, 0.3 ... 0.8, 0.9 etc.; 1, 2, 3, ... 8, 9, 10 etc.; 11, 12, 13, ... 18, 19, 20 etc.; 21, 22, 23, ... 28, 29, 30 etc.; 31, 32, 33, ... 38, 39, 40 etc.; 41, 42, 43, ... 48, 49, 49.1, 49.2, 49.3, ... 49.8, 49.9, et; 49.91, 49.92, 49.93, ... 49.98, 49.99, 50% (w/w).

Particularly advantageous and according to the invention are powders, preferably spray-dried powders, having a proportion of 1,4 O-linked saccharose derivative or a sugar mixture containing at least one 1,4 O-linked saccharose derivative relative to peptide/protein, for example, 25/75, 26/74, 27/73, 28/72, 29/71, 30/70, 31/69, 32/68, 33/67, 34/66, 35/65, 36/64, 37/63, 38/62, 39/61, 40/60, 41/59, 42/58, 43/57, 44/56, 45/55, 46/54, 47/53, 48/52, 49/51, 50/50, 51/49, 52/48, 53/47, 54/46, 55/45, 56/44, 57/43, 58/42, 59/41, 60/40, 61/39, 62/38, 63/37, 64/36, 65/35, 66/34, 67/33, 68/32, 69/31, 70/30, 71/29, 72/28, 73/27, 74/26, 75/25, 76/24, 77/23, 78/22, 79/21, 80/20, 81/19, 82/18, 83/17, 84/16, 85/15, 86/11, 87/13, 88/12, 89/11, 90/10, 91/9, 92/8, 93/7, 94/6, 95/5, 96/4, 97/3, 98/2, 99/1, 99.1/0.9, 99.2/0.8, 99.3/0.7, 99.4/0.6, 99.5/0.5, 99.6/0.4, 99.66/0.33, 99.7/0.3, 99.8/0.2, 99.9/0.1, 99.99/0.01 (w/w). If the corresponding powder contains one or more additional excipients, then either the proportion of the 1,4 O-linked saccharose derivative or the sugar mixture containing at least one 1,4 O-linked saccharose derivative, the proportion of pharmaceutical active substance or both moieties can be appropriately reduced, whereby the proportion of 1,4 O-linked saccharose derivative or the sugar mixture containing at least one 1,4 O-linked saccharose derivative preferably has a value of between 80 and 90% (w/w).

If the powders according to the invention contain very small proteins/peptides having a molecular weight of for example <10 kDa, preferably of <5 kDa, such as, for instance, growth factors, for example cytokine, then the proportion is preferably between 0.1 to 10% (w/w), further preferably between 0.2 to 5% (w/w) of the total weight of the powder. Accordingly, powders are preferred, whose proportion of cytokines are 0.2, 0.3, 0.4 ... 0.8, 0.9, etc.; ... 1, 2, 3, ... etc.; 4.1, 4.2, 4.3, ... 4.8, 4.9, etc.; 4.91, 4.92, 4.93, ... 4.98, 4.99% (w/w).

If, on the other hand, it is a pharmaceutical active substance with one or more antibodies or a derivative thereof (preferably embodiment), then the active substance moiety in the solids content of the powder is between 0.01 and 75% (w/w), preferably between 0.1 and 50% (w/w), further preferred between 0.33 and 50% (w/w), for example 0.1, 0.2, 0.3, 0.33, ... 0.66, 0.7, 0.8, 0.9 etc.; 1, 2, 3, ... 8, 9, 10 etc.; 11, 12, 13, ... 18, 19, 20 etc.; 21, 22, 23, ... 28, 29, 30 etc.; 31, 32, 33, ... 38, 39, 40 etc.; 41, 42, 43, ... 48, 49, etc; 49.1, 49.2, 49.3, ... 49.8, 49.9 etc.; 49.91, 49.92, 49.93, ... 49.98, 49.99, 50% (w/w).

According to a particular embodiment, the antibody moiety of the solids content of the powder is between 10 and 50% (w/w), further preferred between 10 and 30% (w/w), further preferred between 10 and 20% (w/w). Particularly advantageous and in accordance with the invention are powders, preferably spray-dried powders, having a proportion of 1,4 O-linked saccharose derivative or a sugar mixture containing at least one 1,4 O-linked saccharose derivative to antibody of 50/50, 51/49, 52/48, 53/47, 54/46, 55/45, 56/44, 57/43, 58/42, 59/41, 60/40, 61/39, 62/38, 63/37, 64/36, 65/35, 66/34, 67/33, 68/32, 69/31, 70/30, 71/29, 72/28, 73/27, 74/26, 75/25, 76/24, 77/23, 78/22, 79/21, 80/20, 81/19, 82/18, 83/17, 84/16, 85/15, 86/14, 87/13, 88/12, 89/11, or 90/10 (w/w).

According to a further embodiment, the present invention relates to a spray-dried powder, characterized in that the dry mass of the spray dried powder contains at least 25% (w/w), preferably between 50 and 99.99% (w/w), particularly preferably between 60 and 90% (w/w) of sugar, containing at least one 1,4 O-linked saccharose derivative and up to 75% (w/w) of a pharmaceutical active substance, whereby the proportion of lactosucrose, maltosyl sucrose and/or glucosyl sucrose is at least 20% (w/w) with reference to the dry mass of the powder and the sum of the weight percents is a maximum of 100% (w/w). The specialist in the art is able to manufacture corresponding powders. Accordingly, a specialist in the art knows that he can mix a maximum of 10% (w/w) of a pharmaceutical active substance relative to the total solids content of a solution to be sprayed, if the proportion of 1,4 O-linked saccharose derivative or a sugar mixture containing at least one 1,4 O-linked saccharose derivative is to be 90%.

Furthermore, the powders according to the invention can contain other excipients, such as amino acids, peptides, non-biological or biological polymers and/or one or more of sugars, for example. Other prior art excipients are, for example, lipids, fatty acids, esters of fatty acids, steroids (e.g. cholesterol) or chelate binders (e.g. EDTA) as well as various cations (vide supra). Particularly preferred are excipients having a high temperature of vitrification, for example higher than 40° C., preferably higher than 45° C. or higher than 55° C. A listing of suitable excipients can be found in Kippe (Eds.), "*Handbook of Pharmaceutical Excipients*" 3rd Ed., 2000, for example.

Suitable protein-containing excipients are, for example, albumin (of human or recombinant origin), gelatin, casein, hemoglobin and the like. The sugars are preferably mono-, di-, oligo- or polysaccharides or a combination thereof. Fructose, maltose, galactose, glucose, D-mannose, sorbose and the like are examples of simple sugars. Suitable double sugars in terms of the invention are lactose, saccharose, trehalose, cellobiose and the like. Raffinose, melezitose, dextrin, starches and the like are particularly suited as multiple sugars or polysaccharides. Mannitol, xylitol, maltitol, galactitol, arabinitol, adonitol, lactitol, sorbitol (glucitol), pyranosylsorbitol, inositol, myoinositol and the like come under consideration as alcohols of sugars. Suitable amino acids include, for instance, alanine, glycine, arginine, histidine, glutamate, asparagine, cysteine, leucine, lysine, isoleucine, valine, tryptophan, methionine, phenylalanine, tyrosine, citrulline, L-aspartyl-L-phenylalanine methylester (=aspartam), trimethylammonioacetate (=betaine) and the like. Preferably, such amino acids are used, which act as buffers (e.g. glycine or histidine) and/or as dispersing agents. Included in the last-mentioned group especially, predominantly hydrophobic amino acids such as leucine, valine, isoleucine, tryptophan, alanine, methionine, phenylalanine, tyrosine, histidine or proline, for example. In the context of the present invention, the use of isoleucine together with the 1,4 O-linked saccharose derivative or a sugar mixture containing at least one 1,4 O-linked saccharose derivative has been shown to be advantageous, preferably at a concentration of 1 to 19.99% (w/w), particularly preferred at from 5 to 19.99% (w/w), further still preferably of from 10 to 19.99% (w/w). The proportion can be increased to a level of 40% (w/w), inasmuch as the proportion of 1,4 O-linked saccharose derivative or a sugar mixture containing at least one 1,4 O-linked saccharose derivative or the proportion of pharmaceutical active substance is correspondingly reduced, so that the solids content of the powder results in a maximum of 100% (w/w).

Especially advantageous is also the use of di-, tri-, oligo- or polypeptides as further excipients, which contain one or more of these predominantly hydrophobic amino acid residues. Suitable examples of tripeptides include, for example, one or more of the following tripeptides: Leu-Leu-Gly, Leu-Leu-Ala, Leu-Leu-Val, Leu-Leu-Leu, Leu-Leu-Met, Leu-Leu-Pro, Leu-Leu-Phe, Leu-Leu-Trp, Leu-Leu-Ser, Leu-Leu-Thr, Leu-Leu-Cys, Leu-Leu-Tyr, Leu-Leu-Asp, Leu-Leu-Glu, Leu-Leu-Lys, Leu-Leu-Arg, Leu-Leu-His, Leu-Gly-Leu, Leu-Ala-Leu, Leu-Val-Leu, Leu-Met-Leu, Leu-Pro-Leu, Leu-Phe-Leu, Leu-Trp-Leu, Leu-Ser-Leu, Leu-Thr-Leu, Leu-Cys-Leu, Leu-Try-Leu, Leu-Asp-Leu, Leu-Glu-Leu, Leu-Lys-Leu, Leu-Arg-Leu and Leu-His-Leu. The use of tri-peptides of the general formulas Ile-X-X; X-Ile-X; X-X-Ile have been shown to be particularly advantageous, wherein X can be one of the following amino acids: alanine, glycine, arginine, histidine, glutaminic acid, glutamine, asparagine, asparaginic acid, cysteine, leucine, lysine, isoleucine (Ile), valine, tryptophan, methionine, phenylalanine, proline, serine, threonine, tyrosine, L-aspartyl-L-phenylalanine-methylester (=aspartam), trimethylammonio-acetate. Corresponding tri-peptides having the formulat $(Ile)_2$-X, for example Ile-I0le-X, Ile-X-Ile, or X-Ile-Ile, are particularly preferred, wherein X can again be one of the amino acids listed hereinbefore. For example, the following tri-peptides are included here: Ile-Ile-Gly, Ile-Ile-Ala, Ile-Ile-Val, Ile-Ile-Ile, Ile-Ile-Met, Ile-Ile-Pro, Ile-Ile-Phe, Ile-Ile-Trp, Ile-Ile-Ser, Ile-Ile-Thr, Ile-Ile-Cys, Ile-Ile-Tyr, Ile-Ile-Asp, Ile-Ile-Glu, Ile-Ile-Lys, Ile-Ile-Arg, Ile-Ile-His, Ile-Gly-Ile, Ile-Ala-Ile, Ile-Val-Ile, Ile-Met-Ile, Ile-Pro-Ile, Ile-Phe-Ile, Ile-Trp-Ile, Ile-Ser-Ile, Ile-Thr-Ile, Ile-Cys-Ile, Ile-Try-lie, Ile-Asp-lie, Ile-Glu-Ile, Ile-Lys-Ile, Ile-Arg-Ile, Ile-His-Ile. Particularly advantageous is the use of Ile-Ile-Ile.

Suitable polymers include, for example, those already mentioned hereinbefore as excipients, polyvinylpyrrolidone, derivatized celluloses such as, for example, hydroxymethyl., hydroxyethyl-, or hydroxypropyl ethylcellulose, polymer sugars such as, for example, fiscoll, starches such as, for example, hydroxyethyl- or hydroxypropyl starches, dextrins such as, for example, cyclodextrin (2-hydroxypropyl-β-cyclodextrin, sufobutylether-β-cyclodextrin), polyethylene, glycols and/or pectins.

In the case of the salts these are, for example, inorganic salts such as chloride, sulfate, phosphate, diphosphate, hydrobromide and for nitrate salts. Furthermore, the powders according to the invention may also contain organic salts such as malate, maleate, fumarate, tartrate, succinate, ethylsuccinate, citrate, acetate, lactate, methanesulfonate, benzoate, ascorbate, paratoluensulfonate, palmoate, salicylate, stearate, estolate, gluceptate or lactobionate salts, for example. At the same time, corresponding salts may contain pharmaceutically acceptable cations such as sodium, potassium, calcium, aluminum, lithium or ammonium, for example. The use of corresponding cations in combination with the stabilization of proteins is particularly preferred. Therefore, according to a further embodiment the present invention relates to a spray-dried powder, which along with the 1,4 O-linked saccharose derivative or a sugar mixture containing at least one 1,4 O-linked saccharose derivative and the pharmaceutical active substance contains a pharmaceutically acceptable salt.

The present invention thus relates to a spray-dried powder, which together with the 1,4 O-linked saccharose derivative or a sugar mixture containing at least one 1,4 O-linked saccharose derivative and the pharmaceutical active substance, contains one or more of pharmaceutically acceptable excipients and/or one or more salts.

According to a further embodiment, the present invention relates to a spray-dried powder, which along with the 1,4 O-linked saccharose derivative or a sugar mixture containing at least one 1,4 O-linked saccharose derivative and the pharmaceutical active substance, contains one or more of amino acid(s), preferably an amino acid as a further excipient. In this connection, the present invention relates also to those powders, which in regard to their dry mass contain (a) at least 25% (w/w), preferably between 50 and 90% (w/w), particularly preferred between 60 and 90% (w/w) of a 1,4 O-linked saccharose derivative or a sugar mixture containing at least one 1,4 O-linked saccharose derivative, (b) between 1 and 19.99% (w/w) of amino acids and (c) between 0.01 and 74% (w/w) of a pharmaceutical active substance, preferably a biological macromolecule, wherein the total of weight portions is a maximum of 100% (w/w). According to a preferred embodiment, the portion of the 1,4 O-linked saccharose derivative or a sugar mixture containing at least one 1,4 O-linked saccharose derivative is at least 60% (w/w), preferably between 60 and 90% (w/w) with reference to the dry mass of the powder. In a corresponding formulation, the proportion of amino acids is preferably between 1 and 19.99% (w/w) and the proportion of the pharmaceutical active substance is between 0.01 to 39% (w/w).

Thus, the present invention according to a further embodiment relates also to powders, for example, which contain 80% 1,4 O-linked saccharose derivative or a sugar mixture containing at least one 1,4 O-linked saccharose derivative/19% (w/w) amino acids/1% (w/w) pharmaceutical active substance (80/19/1), or, for example, (80/18/2); (80/17/13); (80/16/4); (80/15/5); (80/14/6); (80/13/7); (80/12/8); (80/11/9); (80/10/10); (70/20/10); (70/19/11); (70/18/12); (70/17/13); (70/16/14); (70/15/15); (70/14/16); (70/13/17); (70/12/18); (70/11/19); (70/10/20); (60/20/20); (60/19/21); (60/18/22); (60/17/23); (60/16/24); (60/15/25); (60/14/26); (60/13/27); (60/12/28); (60/11/29) or (60/10/30) or contain or consist of these. Insofar as the active substance moiety is reduced from 20% (w/w) up to 0.01% (w/w), for example to 9.99, . . . 9.9, 9.8, 9.7 . . . 9.3, 9.2, 9.1 . . . 9, 8 7, 6, 5, 4, 3, 2, 1, . . . 0.9, 0.8, 0.7, . . . 0.66, 0.6, 0.5, 0.4, 0.3, 0.2, 0.1, 0.09, 0.08, 0.07, 0.06, 0.05, 0.04, 0.03 0.02, 0.01% (w/w), accordingly the proportion of 1,4 O-linked saccharose derivative or a sugar mixture containing at least one 1,4 O-linked saccharose derivative can be increased to, for example, 80.01, ... 80.1, 80.2, 80,3 ... 80.8, 80.9, 81, 82, 83, 84, 85, 86, 87, 88, 89, ..., 89.1, 89.2, 89.3, ... 89.33, ... 89.4, 89.5, 89.6, 89.7, 89.8, 89.9, ... 89.91, 89.92, 89.93, ... 89.97, 89.98, 89.99% (w/w), so that the sum of the weight proportions of the individual powder components relative to the dry mass of the powder is a maximum of 100% (w/w). By the addition of further excipients or salts, the proportion of the 1,4 O-linked saccharose derivative or a sugar mixture containing at least one 1,4 O-linked saccharose derivative, amino acids/peptides and/or pharmaceutically active substance can be correspondingly adapted/reduced, so that the weight proportions of the individual components in the total gives a maximum of 100% (w/w).

If the added amino acid is isoleucine, then according to a further embodiment powders with a proportion (a) of 1,4 O-linked saccharose derivative or a sugar mixture containing at least one 1,4 O-linked saccharose derivative of at least 25% (w/w), preferably from 50 to 90% (w/w), particularly preferred from 60 to 90% (w/w), (b) a proportion of from 1 to 19.99% (w/w) isoleucine and (c) of at least 0.01% (w/w), preferably 0.01 to a maximum of 74% (w/w) of a pharmaceutical active substance, preferably a peptide/protein, are compliant with the invention.

Preferably the proportion of isoleucine is 5 to 19.99% (w/w), further preferred 10 to 19.99% (w/w) in the total solids of the powder. Here, too, it applies that the total percent by weight of the individual components gives a maximum of 100% (w/w). Furthermore, according to the invention, powders with the following composition are in accord with the invention: 80% (w/w) of 1,4 O-linked saccharose derivative or a sugar mixture containing at least one 1,4 O-linked saccharose derivative/10% (w/w) of amino acid or peptide/10% (w/w) of pharmaceutical active substance (80/10/10); (79/11/10); (78/12/10); (77/13/10); (76/14/10); (75/15/10); (74/16/10); (73/17/10); (72/18/10); (71/19/10); (70/20/10), wherein the proportion of the pharmaceutical active substance can also be reduced from 10 to 0.01% (w/w), for example to 9.99, ... 9.9, 9.8, 9.7 ... 9.3, 9.2, 9.1 ... 9, 8, 7, 6, 5, 4, 3, 2, 1, ... 0.9, 0.8, 0.7, ... 0.66, ... 0.6, 0.5, 0.4, 0.3, 0.2, 0.1, 0.09, 0.08, 0.07, 0.06, 0.05, 0.04, 0.03 0.02, 0.01% (w/w) and accordingly the proportion of the 1,4 O-linked saccharose derivative or a sugar mixture containing at least one 1,4 O-linked saccharose derivative can be increased, for example, to 80.01, ... 80.1, 80.2, 80.3 ... 80.8, 80.9, 81, 82, 83, 84, 85, 86, 87, 88, 89, ..., 89.1, 89.2, 89.3, ... 89.33, ..., 89.4, 89.5, 89.6, 89.7, 89.8, 89.9, ... 89.91, 89.92, 89.93, ..., 89.97, 89.98, 89.99% (w/w), so that the total of the weight proportions with respect to the dry mass of the powder is 100% (w/w). Therefore, powders with the following composition are also according to the invention: 80% (w/w) of 1,4 O-linked saccharose derivative or a sugar mixture containing at least one 1,4 O-linked saccharose derivative/19% (w/w) isoleucine/1% (w/w) of pharmaceutical active substance (80/19/1); (80/18/2); (80/17/3); (80/1611); (80/15/5); (80/14/6); (80/13/7); (80/12/8); (80/11/9); (80/10/10); (70/19/11); (70/18/12); (70/17/13) (70/16/14); (70/15/15); (70/14/16); (70/13/17); (70/12/18); (70/11/19); (70/10/20); (60/19/21); (60/18/22); (60/17/23) (60/16/24); (60/15/25); (60/14/26); (60/13/27); (60/12/28); (60/11/29); (60/10/30). By the addition of further excipients or salts, the proportion of the 1,4 O-linked saccharose derivative or a sugar mixture containing at least one 1,4 O-linked saccharose derivative, isoleucine and/or pharmaceutically active substance can be correspondingly adapted, so that the weight proportions of the individual components in the total gives a maximum of 100% (w/w).

A further embodiment of the present invention relates to the use of at least one 1,4 O-linked saccharose derivative or a sugar mixture containing at least one 1,4 O-linked saccharose derivative and tri-peptides for stabilization of powders that contain a pharmaceutical active substance, preferably in the form of a peptide, protein or a mixture thereof. The present patent specification mentions by way of example several tri-peptides, which can be used together with the 1,4 O-linked saccharose derivative or a sugar mixture containing at least one 1,4 O-linked saccharose derivative for manufacturing the powders according to the invention. According to a particular embodiment, the tri-peptides are those, which contain at least one isoleucine, preferably two isoleucines, or according to a particularly advantageous embodiment, consist of three isoleucines.

In this connection, powders are considered to be in accordance with the invention, which have (a) a proportion of at least one 1,4 O-linked saccharose derivative or a sugar mixture containing at least one 1,4 O-linked saccharose derivative, at least 25% (w/w), preferably from 60 to 99% (w/w), particularly preferably from 80 to 90% (w/w), (b) a proportion of 1 to 19.99% (w/w) of a tri-peptide, preferably tri-isoleucine and (c) 0.01 to a maximum of 74% (w/w) of a pharmaceutical active substance, preferably a peptide/protein. The fact that the total of the individual solids gives a maximum of 100% (w/w) applies in this case, too. Furthermore, according to the invention, powders with the following composition are in accord with the invention: 89% (w/w) of at least one 1,4 O-linked saccharose derivative or a sugar mixture containing at least one 1,4 O-linked saccharose derivative, /1% (w/w) of tri-peptide, preferably an isoleucine-containing tri-peptide, particularly preferably tri-isoleucine/10% (w/w) of pharmaceutical active substance (89/1/10); (88/2/10); (87/3/10); (86/4/10); (85/5/10); (84/6/10); (83/7/10); (82/8/10); (81/9/10); (80/10/10); (79/11/10), (78/12/10); (77/13/10), (76/14/10); (75/15/10), (74/16/10); (73/17/10); (72/18/10) or (71/19/10), wherein the proportion of pharmaceutical active substance can be reduced from 10 to 0.01% (w/w), for example to 9.99, ... 9.9, 9.8, 9.7 ... 9.3, 9.2, 9.1 ... 9, 8, 7, 6, 5, 4, 3, 2, 1, ... 0.9, 0.8, 0.7, ... 0.66, ... 0.6, 0.5, 0.4, 0.3, 0.2, 0.1, 0.09, 0.08, 0.07, 0.06, 0.05, 0.04, 0.03 0.02, 0.01% (w/w), and accordingly the proportion of the 1,4 O-linked saccharose derivative or a sugar mixture containing at least one 1,4 O-linked saccharose derivative can be increased, for example, to 80.01, ... 80.1, 80.2, 80.3 ... 80.8, 80.9, 81, 82, 83, 84, 85, 86, 87, 88, 89, . . . 89.1, 89.2, 89.3, ... 89.33, ... 89.4, 89.5, 89.6, 89.7, 89.8, 89.9, ... 89.91, 89.92, 89.93, ... 89.97, 89.98, 89.99% (w/w), so that the total of the weight proportions with regard to the dry mass of the powder gives a maximum of 100% (why). Accordingly, powders with the following composition are also according to the invention: 80% (w/w) of at least one 1,4 O-linked saccharose derivative or a sugar mixture containing at least one 1,4 O-linked saccharose derivative/19% (w/w) of tri-peptide, preferably tri-isoleucine/1% (w/w) of pharmaceutical active substance (80/19/1); (80/18/2); (80/17/3); (80/16/4); (80/15/5); (80/14/6); (80/13/7); (80/12/8); (80/11/9); (80/10/10); (70/19/11); (70/18/12); (70/17/13); (70/16/14); (70/15/15); (70/14/16); (70/13/7); (70/12/18); (70/11/19); (70/10/20); (60/20/20); (60/19/21); (60/18/22); (60/17/23); (60/16/24); (60/15/25); (60/14/26); (60/13/27); (60/12/28); (60/11/29); (60/10/30), wherein the proportion of tri-peptide, preferably of tri-isoleucine can be reduced also from 10 to 1% (w/w), for example to 9.99, ... 9.9, 9.8, 9.7 ... 9.3, 9.2, 9.1 ... 9, 8, 7, 6, 5, 4, 3, 2, 1.9, 1.8, 1.7, ... 1.66, ... 1.6, 1.5, 1.4, 1.3, 1.2, 1.1, 1% (w/w) and, accordingly the proportion of pharmaceutical active substance, preferably of peptide/protein can be increased, for example, to 30.1, 30.2, 30.3 ... 30.8, 30.9, 31, 32, 33, 34, 35, 36, 37, 38, 38.1, 38.2, 38.3, ... 38.33, ..., 38.4, 38.5, 38.6, 38.738.8, 38.9, . . . 39% (w/w), so that the total of the weight proportions with respect to the dry mass of the powder is a maximum of 100% (w/w). Upon reduction of the proportion of tri-peptides from 10 to 1 (w/w) as represented herein, the proportion of the 1,4 O-linked saccharose derivative or a sugar mixture containing at least one 1,4 O-linked saccharose derivative can also be increased in the powder. At, for example, constant active substance proportion of 10% (w/w) powders can be manufactured having a proportion of 1,4 O-linked saccharose derivative or a sugar mixture containing at least one 1,4 O-linked saccharose derivative of 80.1, 80.2, 80.3 . . . 80.8, 80.9, 81, 82, 83, 84, 85, 86, 87, 88, 88.1, 88.2, 88.3, . . . 88.33, . . . , 88.4, 88.5, 88.6, 88.7, 88.8, 88.9 or 89% (w/w).

In addition, according to a further embodiment according to the invention, the powders can contain tensioactive substances such as Tween 20, 40, 60, 80, Brij 35, Pluronic F 88 and Pluronic F 127. These are used preferably in a concentration of from 0.01-0.1% (w/w). Particularly preferred is a spray-dried powder, which contains at least one 1,4 O-linked saccharose derivative or a sugar mixture containing at least one 1,4 O-linked saccharose derivative and in addition also Tween 20, preferably in a concentration of from 0.01-0.1% (w/w), as a tensioactive substance.

According to a further embodiment, the particles in the powders according to the invention have a MMD and/or a MMAD of between 1 and 10 µm, preferably between 1 and 5 µm.

According to a further embodiment, the present invention relates to spray-dried powders having one of the compositions described herein, which is characterized by a temperature of vitrification of greater than 40° C. Conventionally, the corresponding powders according to the invention have a maximum temperature of vitrification of approximately 96 to 110° C. In isolated cases the value can also be higher.

Furthermore, the present invention relates also to pharmaceutical compositions, which contain at least one of the spray-dried powders according to the invention and described herein.

Manufacture of the Spray-Dried Powders According to the Invention:

The present invention provides also a method for manufacturing one of the spray-dried powders more completely described hereinbefore. The method is characterized in that a solution/suspension for spraying, containing a pharmaceutical active substance and at least one 1,4 O-linked saccharose derivative or a sugar mixture containing at least one 1,4 O-linked saccharose derivative is sprayed at a temperature of below 200/120° C. (inflow/outflow temperature), preferably at a temperature of 186/96° C., preferably between 186/96° C. and 60/40° C., for example at a temperature of 180-150/95-80° C. The process according to the invention is more completely described in the EXAMPLES section with reference to several examples.

In principle, the powders according to the invention can be manufactured, in that the pharmaceutical active substance, preferably a biological macromolecule, is dissolved in the form of a peptide or protein in an aqueous solution, depending on the solubility conditions of the respective active substance. Generally, buffered solutions with a pH of 3-11, preferably from 3.5-9, are used. When manufacturing inhalable powders, an aqueous solution having a pH of 4-7.8 is particularly advantageous. In order to assure adequate solubility, the pH of the solution should be below the pI of the peptide/protein. The aqueous solution can contain optionally additional water-soluble organic solvents such as, acetone, alcohols or the like, for example. Lower alcohols such as methanol, ethanol, propanol (n- or iso-propanol) or the like are particularly suitable. Such mixed solvent systems normally contain between 10-20% (v/v) of a water-soluble organic solvent. The solids moiety in the sprayed solution usually is between 0.01-20% (w/w), preferably between 0.05-10% (w/w), particularly preferably between 0.1-5% (w/w). In the context of the present invention, spray-dried powders were manufactured starting with an aqueous solution having a solids proportion of 10% (w/w), 3.33% (w/w) or 2.00% (w/w), and freeze-dried powders were manufactured starting with an aqueous solution having a solids moiety of 10% (w/w).

Typically the excipient or a mixture of suitable excipients as described hereinbefore by way of example is dissolved in a second container with pharmaceutical grade water or a suitable buffer solution having a pH of from 3 to 11, preferably from 3.5 to 9 and particularly preferred from 4.0 to 7.8 and mixed in a second step with the active substance solution. Then the solution/suspension is adjusted to the desired solids content using pharmaceutical grade water or a suitable buffer solution having a pH of from 3 to 11, preferably from 3.5 to 9 and particularly preferred from 4.0 to 7.8.

Hence, the present invention relates to a method for manufacturing a spray-dried powder characterized in that:
a) a pharmaceutical active substance is dissolved/suspended in an aqueous solution/suspension;
b) one or more 1,4 O-linked saccharose derivative chosen from the group comprising the compounds lactosucrose, glucosyl sucrose or maltosyl sucrose or a sugar mixture containing at least one of these 1,4 O-linked saccharose derivatives are dissolved/suspended in an aqueous solution/suspension;
c) insofar as the active substance and 1,4 O-linked saccharose derivative or the sugar mixture containing at least one 1,4 O-linked saccharose derivative is dissolved/suspended in different solutions/suspension, these are mixed.
d) the solution/suspension containing one or more 1,4 O-linked saccharose derivative(s) and the pharmaceutical active substance are sprayed at a temperature of less than 200/120° C. (inflow/outflow temperature), preferably between 60/40 and 186/95° C.

The 1,4 O-linked saccharose derivative can also be a part of a sugar mixture, which contains at least one 1,4 O-linked saccharose derivative. Examples corresponding to suitable sugar mixtures are more completely described by way of example under the section "Definitions". In this case the sugar mixtures can contain, along with the 1,4 O-linked saccharose derivative, one or more mono-, di- and/or polysaccharides, wherein the additional utilization of mono- and/or disaccharides in manufacturing the powders is preferred. In the context of the invention, for example, sugar mixtures can be used having lactosucrose, lactose and saccharose, wherein the proportion of lactosucrose with respect to the total sugar proportion is ≧40% (w/w), preferably ≧55% (w/w), particularly preferably ≧88% (w/w) or more. Preferably, the sugar mixture is a sugar mixture designated as als Nyuka-Oligo® LS55P, or abbreviated LS55P (Hayashibara Shoji, Inc., Japan), which contains at least 55% of lactosucrose, a maximum of 25% (w/w) of lactose and a maximum of 10% (w/w) of saccharose. According to a further embodiment, the sugar mixture is a sugar mixture designated Nyuka-Oligo® LS90P, abbreviated LS90P, (Hayashibara Shoji, Inc., Japan), which contains at least 88% of lactosucrose and a maximum of 10% (w/w) of lactose and saccharose. Furthermore, sugar mixtures comprised of a combination of glucosyl and maltosyl sucrose can be used, preferably in combination with other mono-, di- and/or polysaccharides. Thus, in terms of the present invention, also corresponding sugar mixtures comprised of glucosyl and maltosyl sucrose, saccharose, glucose and/or fructose are suitable, wherein the proportion of glucosyl- and maltosyl-sucrose with respect to the total sugar proportion is preferably 25% (w/w) or more. According to a further preferred embodiment, the respective proportion of glucosyl- and maltosyl-sucrose is at least 18% (w/w) of the total sugar proportion. According to a further preferred embodiment the sugar mixture is a sugar mixture designated as Coupling Sugar® (Hayashibara Shoji, Inc., Japan), which contains at least 18% (w/w) of glucosyl- and maltosyl sucrose, between 11 and 15 (w/w) of saccharose and between 5 and 9% (w/w) of each of glucose and fructose. Furthermore, in terms of the present invention a sugar mixture designated also as Coupling Sugar S® (Hayashibara Shoji, Inc., Japan), which contains at least 25% (w/w) glucosyl- and/or maltosyl-sucrose, between 48 and 56% (w/w) of saccharose and not more than 10% (w/w) of glucose and fructose.

The excipient content in 1,4 O-linked saccharose derivative or a sugar mixture containing at least one 1,4 O-linked saccharose derivative in the solution/suspension to be sprayed is between 25% and 99.99% (w/w), preferably between 60% and 99% (w/w), further preferably between 60 and 90% (w/w), particularly preferably between 80 and 90% (w/w) with respect to the solids content of the spray solution. The active substance concentration is normally between 0.01 and 75% (w/w), preferably between 0.01 and 40% (w/w), particularly preferably between 0.01 and 30% (w/w) with respect to the solids content of the solution or suspension to be sprayed. The specialist in the art is capable of manufacturing the solutions/suspensions to be sprayed using the powder compositions described hereinbefore, which after spraying result in the corresponding powder compositions.

Thus, the present invention relates also to a method for manufacturing a spray-dried powder as described hereinbefore, characterized in that the solids content of the solution/suspension to be sprayed contains between 25 and 99.99% (w/w), preferably between 60 and 90% (w/w) of at least one 1,4 O-linked saccharose derivative or a sugar mixture containing at least one 1,4 O-linked saccharose derivative. According to another preferred embodiment, the present invention relates to a corresponding method, characterized in that the solids content of the solution/suspension to be sprayed contains a pharmaceutical active substance of between 0.01 and 75% (w/w), preferably between 0.01 and 30% (w/w), particularly preferably between 0.33 and 30% (w/w).

According to a further embodiment of the present method, a spray solution/suspension having a solids content of (a) at least 25% (w/w), for example between 25 to 99.99% (w/w) of at least one 1,4 O-linked saccharose derivative or a sugar mixture containing at least one 1,4 O-linked saccharose derivative and (b) at least 0.01% (w/w), preferably 0.01 to 75% (w/w) of a pharmaceutical active substance, preferably a biological macromolecule, is manufactured and sprayed, wherein the total percent by weight is a maximum of 100% (w/w) with respect to the solids content of the spray solution. According to a preferred embodiment, a spray solution/suspension having a solids content (a) of at least one 1,4 O-linked saccharose derivative or a sugar mixture containing at least one 1,4 O-linked saccharose derivative of at least 60% (w/w), preferably between 60 and 90% (w/w), and (b) 0.01 to 40% (w/w) of a pharmaceutical active substance, preferably a biological macromolecule, is manufactured and sprayed, wherein the total percent by weight of the solution or suspension is a maximum of 100% (w/w) with respect to the solids content of the spray solution.

In addition, according to the hereinbefore described powders according to the invention, the solution/suspension to be sprayed according to the invention according to another embodiment contains one or more of pharmaceutically acceptable excipients and/or one or more salts. The excipients are preferably amino acids, peptides or their salts, sugars, polyols, salts of organic acids and/or polymers.

Preferably the spray solution contains one or more of amino acids and/or peptides or proteins as additional excipients in addition to the pharmaceutical active substance and at least one 1,4 O-linked saccharose derivative or a sugar mixture containing at least one 1,4 O-linked saccharose derivative. Hence, the present invention relates also to a method for manufacturing spray-dried powders, characterized in that the solution/suspension to be sprayed, with respect to its solids content, contains (a) at least 25% (w/w), preferably at least 60% (w/w) of at least one 1,4 O-linked saccharose derivative or a sugar mixture containing at least one 1,4 O-linked saccharose derivative, (b) between 1 and 39.99% (w/w) of at least one amino acid and/or at least one peptide and (c) at least 0.01% (w/w) of a pharmaceutical active substance. Examples of suitable excipients, including pharmaceutically acceptable salts, peptides, and amino acids can be found under the section "powders according to the invention" in this patent specification.

According to a further preferred embodiment, the spray solution contains, in addition to at least one 1,4 O-linked saccharose derivative or a sugar mixture containing at least one 1,4 O-linked saccharose derivative, one or more of amino acids as further excipients. Spray solutions/suspensions are considered advantageous, whose solids content includes (a) at least 25% (w/w), preferably 60 to 90% (w/w) of at least 1,4° linked saccharose derivative or a sugar mixture containing at least one 1,4 O-linked saccharose derivative, (b) 1 to 19.99% (w/w) of amino acids, (c) and at least 0.01% (w/w) of a pharmaceutical active substance, preferably a peptide/protein such as an antibody, for example. The proportion of pharmaceutical active substance in this case is preferably 0.01 to a maximum of 74% (w/w), preferably 0.01 to 39% (w/w), wherein the total of the solids moieties is a maximum of 100%. In this case, the specialist is able to manufacture corresponding powders and fine tune the weight proportions, so that the total of the solids proportions is a maximum of 100% (w/w).

If the proportion (relative to the total solids content) of pharmaceutical active substance is, for example, 10% (w/w) and the proportion of at least one 1,4 O-linked saccharose derivative or a sugar mixture containing at least one 1,4 O-linked saccharose derivative is 80% (w/w), then the specialist in the art knows that he can add a maximum of 10% (w/w) of amino acids to the spray solution/suspension.

According to a further preferred embodiment, the spray solution contains, in addition to at least one 1,4 O-linked saccharose derivative or a sugar mixture containing at least one 1,4 O-linked saccharose derivative, one isoleucine as a further excipient. Spray solutions/suspensions are considered advantageous, whose solids content includes (a) at least 25% (w/w), preferably 60 to 90% (w/w) of at least one 1,4 O-linked saccharose derivative or a sugar mixture containing at least one 1,4 O-linked saccharose derivative, (b) 1 to 19.99% (w/w) of isoleucine, (c) and at least 0.01% (w/w) of a pharmaceutical active substance, preferably a peptide/protein such as an antibody, for example. The proportion of the pharmaceutical active substance in this case is preferably 0.01 to a maximum of 74% (w/w), preferably 0.01 to 39% (w/w) as a factor of the concentration of the 1,4 O-linked saccharose derivative or a sugar mixture containing at least one 1,4 O-linked saccharose derivative, wherein the total of the solid content proportions is a maximum of 100%. In this case, the specialist in the art is able to manufacture corresponding powders and fine tune the weight proportions, so that the total of the solids proportions is a maximum of 100% (w/w). If the proportion (relative to the total solids content) of pharmaceutical active substance is, for example, 10% (w/w) and the proportion of at least one 1,4 O-linked saccharose derivative or a sugar mixture containing at least one 1,4 O-linked saccharose derivative is 80% (w/w), then the specialist in the art knows that he can add a maximum of 10% (w/w) of isoleucine to the spray solution/suspension.

According to a further embodiment, the solution to be sprayed contains, along with at least one 1,4 O-linked saccharose derivative or a sugar mixture containing at least one 1,4 O-linked saccharose derivative, one or more of tri-peptides, preferably tri-peptides containing isoleucine, particularly preferably Tri-Isoleucin. Solutions or suspensions to be sprayed are considered advantageous, whose solids content is (a) at least 25% (w/w), preferably 60 to 90% (w/w) of at least one 1,4 O-linked saccharose derivative or a sugar mixture containing at least one 1,4 O-linked saccharose derivative, (b) 1 to 19.99% (w/w) of a tri-peptide, preferably tri-isoleucine, and (c) at least 0.01% (w/w) of a pharmaceutical active substance, preferably a peptide/protein such as, for example, an antibody, wherein the total of the solids proportions is a maximum of 100% (w/w). The proportion of the pharmaceutical active substance in this case is preferably 0.01 to a maximum of 74% (w/w), preferably 0.01 to 39% (w/w) as a factor of the concentration of the 1,4 O-linked saccharose derivative or a sugar mixture containing at least one 1,4 O-linked saccharose derivative, wherein the total of the solid content proportions is a maximum of 100%. In this case, the specialist in the art is able to manufacture corresponding powders and fine tune the weight proportions, so that the total of the solids proportions is a maximum of 100% (w/w). If the proportion (relative to the total solids content) of pharmaceutical active substance is, for example, 10% (w/w) and the proportion of at least one 1,4 O-linked saccharose derivative or a sugar mixture containing at least one 1,4 O-linked saccharose derivative is 80% (w/w), then the specialist in the art knows that he can add a maximum of 10% (w/w) of tri-peptide, preferably of tri-isoleucine, to the spray solution/suspension.

As already mentioned, it is advantageous if the solutions to be sprayed are manufactured and sprayed at a pH of between 3 and 11, preferably between 3.5 and 9, particularly preferably between 4.0 and 7.8. Suitable buffer systems are well-known to the specialist in the art. Typically, the utilization of inorganic or organic salts as buffer systems has been shown to be particularly advantageous.

Typically, the optimum excipient and protein content for each protein or peptide is determined experimentally. Preferred formulations of the invention can still contain at least one additional excipient, in order to improve the powder properties such as dispersibility and flow, while maintaining superior inhibition of aggregate formation.

Spraying is done in conventional spray dryers, for example in equipment manufactured by Niro A/S (Soeborg, DK), Büchi Labortechnik GmbH (Flawil, CH) or the like. The optimum conditions for spray drying depend on the respective formulation and must be determined experimentally. Air is typically used as the gas but inert gases such as nitrogen argon are also suitable. In addition, the spray-drying temperature is determined; in other words, the inlet temperature and the outlet temperature, according to the temperature sensitivity of the active substance used, each as a factor of the stabilizers used. Usually inlet temperature is 50-200° C., while the outlet temperature is generally 30-150° C. In the context of the present invention, an inlet temperature of approximately 170-185° C. and an outlet temperature of 80-100° C. was used. However, it is also possible to use an inlet temperature of up to 200° C., preferably 60-185° C., and an outlet temperature of up to 120° C., preferably 40-105° C., depending on the stabilizer moiety. Spraying is done generally at a pressure of approximately 20-150 psi, preferably at approximately 30 or 40-100 psi, for example at approximately 30, 40, 50, 60, 70, 80, 90 or 100 psi.

With respect to the Büchi B290 spray drier, the "liquid feed rate" is normally between 0.1 and 100 ml/min, preferably between 0.1 and 30 ml/min, for example approximately 3 ml/min. In this connection, an aspirator flow rate of 20-40 $m^3/h$, preferably of 30-40 $m^3/h$ such as, for example, 38.3 $m^3/h$ and atomization rates of 0.3-2.5 $m^3/h$, preferably of approximately 0.67 $m^3/h$, 1.05 $m^3/h$ an 1.74 $m^3/h$ have been shown to be particularly suitable.

The spray-dried active substance formulations, preferably the protein-powder formulations can optionally be subjected to a second gentle drying (post-drying). The objective is to obtain a more uniform residual water content in the formulations, preferably less than 2% (w/w) and thus to improve both the stability of the active substance and also improve the powder properties such as the temperature of vitrification, flow and dispersibility. The conditions of the post-drying process must be selected, so that the aggregate formation of the active substance is not significantly increased. This applies in particular to the use of biological macromolecules such as, for example, the use of peptides/proteins. The spray-drying active substance powder formulations are manufactured, further processed and stored preferably under dry conditions (at low relative humidity). The process of secondary drying makes it possible to further reduce the moisture content in the powders, despite relatively high residual water content after spray drying. Surprisingly, in the preferred formulations, the excipients that are the subject matter of the invention stabilize the proteins, even at non-optimum process and storage conditions.

Properties of the Spray-Dried Dry Powder Formulations

The dry protein powder formulations manufactured in the context of this invention have a residual water content of under 15% (w/w); normally under 10% (w/w) and preferably under 6% (w/w). Further preferably, the spray-dried protein powder formulations have a residual water content of under 5% (w/w), particularly preferably under 3% (w/w) and most preferably a residual water content of between 0.2 and 2.0% (w/w). Formulations having a lower residual moisture generally exhibit improved stability during packaging and storage. Furthermore, the dried protein powder formulations of the invention are especially hygroscopic; that is, they tend to absorb moisture from their surroundings. In order to prevent this, such powders are usually stored in containers that exclude atmospheric moisture, such as blister packaging. Surprisingly, in the selected formulations of the powder according to the invention, it was found that the powders remained stabile even in open storage for a month a 43% relative humidity both in terms of protein stability and inhalability.

The stabilizing effects of the excipients described herein are capable of protecting the protein from the extreme stresses during spray-drying and storage. In the absence of excipients, spray-dried pure protein formulations form extensive aggregates. Factors associated with processing such as heat, shearing stress and denaturing at the air-water interfaces cause aggregation (up to approximately 3.7 aggregates) during spray drying and subsequent secondary drying (up to approximately 4.0 aggregates). During storage, because of the absence of the stabilizing hydrate shell of the proteins, massive aggregate formation occurs (of approximately 11.8 to approximately 18.9% aggregates).

The preferred spray-dried formulations of the invention are, in contrast with the pure protein formulations, capable of reducing the formation of aggregates both following spray-drying and maintaining them at a low level even under different storage conditions. In virtue of the spray-drying and subsequent secondary drying, only approximately 0.5 to approximately 1.8% aggregates versus up to approximately 4.0% aggregates in the case of pure protein formulations. In the case of a particularly challenging storage condition (40° C., 75% relative humidity), "forced storage stability", the preferred formulations are characterized by clear superiority (aggregates of approximately 1.0 to approximately 13.1%) versus pure protein formulations (approximately 18.2 to 18.9% aggregates) and an analogous reference formulation with trehalose as the excipient. This advantage becomes particularly salient in comparison with the formulation presented in Example 4. The addition of tri-isoleucine in the spray solution results in a significant improvement in the aerodynamic properties of the powder. Surprisingly, only the combinations that contain at least a 1,4 O-linked saccharose derivative and tri-isoleucine, in particular LS55P and tri-isoleucine and LS90P and tri-isoleucine, are able to preserve the protein against the formation of aggregates (only 0.7 to 4.4% aggregates). Neither the combination described in WO 01/32144 using tri-leucine with raffinose (12.6% aggregates) or hydroxyethyl starch (approximately 18.6% aggregates) nor the trehalose described in the prior art as an outstanding stabilizer can protect the protein against aggregation under the particularly challenging conditions in combination with tri-isoleucine. Both the LS55P-tri-isoleucine-formulations and the LS90P-tri-isoleucine-formulation are clearly advantageous vis-á-vis a saccharose-tri-isoleucine formulation (5.6% aggregates) and saccharose-lactose-tri-isoleucine formulation (8.8% aggregates). This is even more surprising, because lactose is also present up to 25% in LS55P along with saccharose. It is obvious, that the negative effect that the reducing sugar lactose has on protein stability is overcompensated for by the 1,4 O-linked saccharose derivative in the case of the LS55P due to the lactosucrose contained. A higher proportion of lactosucrose in the sugar moiety of the powder formulations is even more advantageous for protein stability (see LS90P formulations).

Formulations, which have a significant stabilizing effect on the incorporated proteins already at relatively brief storage under particularly destabilizing conditions (1 week at 40° C., 75% relative humidity), stabilize proteins even over the long term under considerably milder standard storage conditions (e.g. 1 year dry, approx. 25° C.).

After equilibration with subsequent four-week storage under dry conditions at 40° C. ("equilibrated storage stability"), the powder formulations containing LS55P and coupling sugar are characterized by low aggregate content (approx. 1.4 to 3.2% aggregates), especially in comparison with pure protein powders (approx. 11.8% aggregates).

After equilibration with subsequent four-week storage under dry conditions at 40° C. ("vacuum dried storage stability"), the powder formulations containing LS55P and coupling sugar are characterized by low aggregate content (approx. 1.1 to 2.1% aggregates), especially in comparison with pure protein powders (approx. 13.2% aggregates).

LS55P (80%), isoleucine (10%) and IgG1 (10%) formulations with a fine particle fraction of approximately 35% show aggregates under 1.9% after vacuum drying with subsequent filling under nitrogen after three-months storage under dry conditions at 2 to 8° C., 25° C. and 40° C.

LS55P (80%), tri-isoleucine (10%) and IgG1 (105) formulations having a MMAD of approximately 3.9 µm and a fine particle fraction of 58.3% after spray drying, exhibit after vacuum drying with subsequent filling under nitrogen after three-months storage under dry conditions at 2 to 8° C. and 25° C. aggregate contents under 1.9% and under dry storage conditions at 40° C. (3 month stability) they exhibit aggregate contents under 2.6%.

Furthermore, the aforementioned LS55P (80%), tri-isoleucine (10%) and IgG1 (10%) formulations show, after one-month open storage at approx. 43% relative humidity and 25° C. (open 1-month stability), continued low aggregate content (approx. 1.3%) at almost identically low MMAD (approx. 3.8 µm) and identically high fine particle fraction (approx. 59.6%).

LS90P (90%) and IgG1 (10%) formulations having an MMAD of approx. 3.8 µm, a MMD of approx. 2.8 µm and a fine particle fraction of approx. 24% after spray drying exhibit after vacuum drying with subsequent filling under nitrogen after one-month storage under dry conditions at 2 to 8° C., 25° C. and 40° C. (1 month's stability) aggregate contents under 1.2%.

LS90P (80%), isoleucine (10%) and IgG1 (10%) formulations with a fine particle fraction of approximately 28% show aggregate contents under 0.9% following vacuum drying with subsequent filling under nitrogen after one month's storage under dry conditions at 2 to 8° C., 25° C. and 40° C. (1 month stability).

LS90P (80%), tri-isoleucine (10%) and IgG1 (10%) formulations with a MMAD of approximately 4.8 µm and a fine particle fraction of 53.2% after spray drying show aggregate contents under 1.0% following vacuum drying with subsequent filling under nitrogen after one-month's storage under dry conditions at 2 to 8° C., 25° C. and 40° C. (1 month stability).

Furthermore, variations of the aforementioned LS90P (80%), tri-isoleucine (10%) and IgG1 (10%) formulations after one-month open storage at approx. 43% relative humidity and 25° C. (open 1 month stability) continue to show low aggregate contents of between approx. 0.5% and 0.7%. After spray drying the MMADs are between approx. 3.9 and 3.3 µm and the FPFs are between approx. 55.6 and 58.9%. After one-month open storage at 43% relative humidity at 25° C. the aforementioned formulations continue to show low MMADs (approx. 4.1 to 3.5 µm) and a high fine particle fraction (approx. 62.3 to 67.3%).

By variation of the spay-drying conditions powders can be manufactured, which preferably have a median particle size (MMD) of less than 20 µm, preferably of less than 10 µm. According to a particularly preferred embodiment, these particles according to the invention have a mean particle size of less than 7.5 µm, preferably less than 5 µm. Especially preferred are particles having a mean particle size of less than 4 µm and further preferred of less than 3.5 µm. In general, particles having a mean particle diameter of 0.1-5 µm, preferably of 0.2-4 µm can be manufactured. In a further embodiment, non-inhalable particles such as lactose, having a particle size of at least 40 µm, preferably between 40 and 200 µm, are added to the corresponding powders. The proportion is preferably at least 15%, further preferred at least 20%, still further preferred at least 30%, further preferred still at least 40% and particularly preferred at least 50 or 60%.

Along with the median particle size (MMD=mass median diameter) the inhalability is dependent essentially on the mass median aerodynamic diameter (MMAD). The particles according to the invention preferably have a MMAD of less than 10 μm and further preferred one of less than 7.5 μm. Particularly advantageous are powders consisting of particles having an MMAD of less than 5.5 μm, preferably of less than 5 μm, still further preferred on of less than 4.5 μm. The powders described in the examples can be manufactured with corresponding particle sized by the combination of optimum spray-drying conditions and selection and concentrations of the excipients according to the invention. In particular, the mixing of amino acids and/or tri-peptides results in an improved particle performance with an increased proportion of inhalable particles with a MMAD of less than 7.5 μm, preferably less than 5.5 μm. By the addition of isoleucine or tri-isoleucine, inhalable powders can be manufactured that have a FPF of greater than 28%, preferably of greater than 40%, further preferred of greater than 50 and further preferred still of greater than 55% (see EXAMPLES).

The powders according to the invention are further characterized by a temperature of vitrification of at least 40° C., preferably of at least 50° C., further preferably of at least 55° C., further preferred still of at least 60° C. Particularly preferred powders have a temperature of vitrification of at least 65° C. In general, the temperature of vitrification of the powders according to the invention is 40 to 110° C. Accordingly, the present invention relates also to powders, preferably spray-dried powders, containing a pharmaceutical active substance and LS90P, LS55P, coupling sugar or coupling sugar S, wherein the temperature of vitrification is 40° C. and higher, preferably between 45 and 60° C. or higher. According to a further preferred embodiment, the temperature of vitrification is 55° C. and higher, preferably between 55 and 60° C. or higher.

Use of the Spray-Dried Powder:

The powders according to the invention are suitable for manufacturing a medicinal product, preferably for manufacturing an inhalative medicinal product.

Freeze-Dried Powders:

In the alternative, powders can be manufactured by freeze drying with subsequent pulverization (see examples). In the examples illustrated herein, the pulverization is done as simply as possible by means of a spatula in the lyophilization vial. The lyophilisate can, of course, be pulverized also by means of mills such as a cutting mill, a ball mill, a rod mill, a mortar mill, air jet mill or other suitable method (see Bauer, Fromming, Führer, 6$^{th}$ ed.).

Properties of the Freeze-Dried, Pulverized Dried Powder Formulations:

The dry protein powder formulations manufactured in the context of this invention have a residual water content of under 15% (w/w); normally under 10% (w/w) and preferably under 5% (w/w). Further preferably, the spray-dried protein powder formulations have a residual water content of under 3% (w/w), particularly preferably under 2% (w/w) and most preferably a residual water content of between 0.2 and 1.5% (w/w). Formulations having a lower residual moisture generally exhibit improved stability during packaging and storage. Furthermore, the dried protein powder formulations of the invention are especially hygroscopic; that is, they tend to absorb moisture from their surroundings. In order to prevent this, such powders are usually stored in containers that exclude atmospheric moisture, such as blister packaging.

The stabilizing effects of the excipients described herein are capable of protecting the protein from the extreme stresses during freeze-drying and storage. In the absence of excipients, freeze-dried pure protein formulations form extensive aggregates. Factors associated with processing such as stress at the time of freezing, concentration, pH shift, and denaturing at the air water interfaces cause aggregation (up to approx. 2.1% aggregates) during the freeze-drying. Because of the presence of the absence stabilizing hydrate shell of the proteins, there is massive formation of aggregates (20.5% aggregates) in the course of storage.

The preferred freeze-dried formulations of the invention are, in contrast with the pure protein formulations, capable of reducing the formation of aggregates both following spray-drying and maintaining them at a very low level even under different storage conditions. The freeze-dried and pulverized lyophilisates are characterized in the particularly challenging storage conditions (40° C., 75% relative humidity), the "forced stability", by a clear superiority of the preferred formulations (aggregates from approx. 1.2 to approx. 1.5%) versus pure protein formulations (approx. 14.5% aggregates) and an analogous reference formulation with mannitol (approx. 34.0% aggregates) as the excipient.

Formulations, which have a significant stabilizing effect on the incorporated proteins already at relatively brief storage under particularly destabilizing conditions (1 week at 40° C., 75% relative humidity), stabilize proteins even over the long term under considerably milder standard storage conditions (e.g. 1 year dry, approx. 25° C.).

After freeze-drying, pulverization and equilibration with subsequent four-week storage under dry conditions at 40° C. ("equilibrated storage stability"), the powder formulation containing LS55P and coupling sugar are characterized by low aggregate contents (approx. 2.6 and 4.6% aggregates), especially in relation to pure protein powders (approx. 15.3% aggregates) and an analogous reference formulation using mannitol (approx. 11.6% aggregates) as excipient.

After freeze-drying, pulverization and vacuum drying with subsequent four-week storage under dry conditions at 40° C. ("vacuum-dried storage stability"), the powder formulation containing LS55P and coupling sugar are characterized by low aggregate contents (approx. 1.2 and 1.5% aggregates), especially in relation to pure protein powders (approx. 14.5% aggregates) and an analogous reference formulation using mannitol (approx. 6.2% aggregates) as excipient.

In addition, the powders according to the invention are characterized by a temperature of vitrification of at least 40° C., preferably of at least 50° C., further preferably of at least 55° C. In general, the temperature of vitrification of the powders according to the invention is 40 to 110° C. but can in the isolated instance exceed this value. Accordingly, the present invention relates also to powders, preferably freeze-dried powders, containing a pharmaceutical active substance and LS90P, LS55P, coupling sugar or coupling sugar S, wherein the temperature of vitrification is 40° C. and more, preferably between 45 and 60° C. or higher. According to a further preferred embodiment, the temperature of vitrification is 55° C. and higher, preferably between 55 and 60° C. or higher or up to 110° C.

Administration of the Powders According to the Invention

In principle, the powder preparations according to the invention can be administered directly as dry powder using so-called dry-powder inhalers or after suspension or reconstitution in the form of aerosols using so-called misters. In this case, the inhalation powders according to the invention can be administered by means of inhalers well-known from the prior art.

Inhalation powders according to the invention can, for example, be administered by means of inhalers, which administer a single dose from a storage chamber by means of a measurement chamber as is described in U.S. Pat. No. 4,570,630 A or using other devices, as are described in DE 36

25 685A. Preferably, the inhalation powders according to the invention are filled into capsules (so-called inhalettes), which are place in the inhalers for use, as described in WO 94/28958, for example.

Other examples of suitable inhalers are found inter alia in U.S. Pat. No. 5,458,135; U.S. Pat. No. 5,785,049 or WO 01/00263. Other suitable inhalers are known from WO 97/41031; U.S. Pat. No. 3,906,950 and U.S. Pat. No. 4,013,075. Other dispersion inhalers for thy powder preparations are described in EP 129 985; EP 472 598; EP 467 172 and U.S. Pat. No. 5,522,385.

The inhalation powders according to the invention can, for example, be administered by means of the well-known Turbohaler® (AstraZeneca LP) or using inhalers such as are disclosed in EP 237 507 A. Other suitable inhalers include the Rotahaler® or the Discus® (both from GlaxoSmithKline Corp.), the Spiros™ Inhaler (Dura Pharmaceuticals) and the Spinhaler® (Fiscon).

A particularly preferred inhaler for the administration of the medicinal product combinations in inhalettes according to the invention can be seen in FIG. 23. The inhaler (Handihaler) for inhalation of powdered medicinal products from capsules is characterized by a housing 1, containing two windows 2, a deck 3, in which the air inlet openings are arranged and which is equipped with a screen 5 affixed using a screen housing 4, an inhalation chamber 6 connected to the deck 3, on which a presser 9 that can be moved against the spring 8 and having two ground needles 7, and a mouth piece 12 connected via an shaft 10 and foldable with the housing 1, the deck 3 and a cap 11, and an air passage opening 13 for adjusting the flow resistance.

If the inhalation powders according to the invention are filled in terms of the preferred application into capsules (inhalettes) as hereinbefore described, fill quantities of from 1 to 30 mg are possible.

In addition, the powders according to the invention can be administered as inhalation aerosols containing propellant gas or without propellant gas. In this case, the powders according to the invention are suspended in solutions or mixtures of solutions liquefied under pressure or reconstituted in an aqueous solution. Suitable suspensions or solutions are well-known in the prior art. Reconstitution is advantageous, for example, in physiological solutions at a pH of 3-11, preferably of 4-9. Particularly advantageous is reconstitution in an aqueous solution having a pH of 5.5-7.8. The suspensions or solutions containing propellant gases for reconstitution of the powders according to the invention can contain further excipients in the form of stabilizers, emulsifiers, surface-active substances, water-soluble organic solvents. Corresponding substances are well-known to the specialist in the art and are described, for example in (Bauer, Lehrbuch der Pharmazeutischen Technologie, Wissenschaftl. Verlagsgesellschaft mbH, Stuttgart, 178-184; Adler, 1998, Journal of Pharmaceutical Sciences, 88(2), 199-208). Corresponding inhalation aerosols that are manufactured by suspension or reconstitution of the powders according to the invention are also the subject matter of the present invention.

The propellant gases that can be used for manufacturing the inhalation aerosols according to the invention are well-known from the prior art. Suitable propellant gases are chosen from the group comprised of the hydrocarbons such as n-propane, n-butane or isobutane and the halogenated hydrocarbons such as preferably the chlorinated and fluorinated derivatives of methane, ethane, propane, butane, cyclopropane or cyclobutane. In this case, the aforementioned propellant gases can be used either alone or in mixtures thereof. Particularly preferred propellant gases are halogenated alkane derivatives chosen from TG11, TG12, TG134a (1,1,1,2-Tetrafluorethane), TG227 (1,1,1,2,3,3,3-Heptafluorpropane) and mixtures thereof, wherein the propellant gases TG 134a, TG227 and mixtures thereof are preferred.

The inhalation aerosols containing propellant gases according to the invention can contain up to 5% (w/w) of active substance. Aerosols according to the invention contain, for example, 0.002-5% (w/w), 0.01-3% (w/w), 0.015-2% (w/w), 0.1-2% (w/w), 0.5-2% (w/w) or 0.5-1% (w/w) of the pharmaceutical active substance. Inhalation aerosols having a corresponding concentration of active substance can be adjusted to the powders according to the invention in a corresponding quantity of solvent by specific reconstitution.

The aforementioned inhalation aerosols containing propellant gases according to the invention can be administered by means of inhalers (MDI=metered dose inhalers) well-known in the prior art. Reference is made by way of example to the Ventolin® (Ventolin Pharmacy) inhalers or those described in U.S. Pat. No. 5,32,094 or U.S. Pat. No. 5,672,581. Accordingly, a further aspect of the present invention relates to medicinal products in the form of the aforementioned aerosols containing propellant gases in conjunction with one or more of inhalers suitable for administering these aerosols. In addition, the present invention relates to inhalers characterized in that they contain the aforementioned aerosols containing propellant gases according to the invention.

The present invention further relates to cartridges, which are equipped with a suitable valve for use in a suitable inhaler for and which contain one of the aforementioned inhalation aerosols containing propellant gases according to the invention. Suitable cartridges and methods for filling such cartridges with the inhalation aerosols containing propellant gases according to the invention are well-known in the prior art.

Furthermore, the powders according to the invention can be reconstituted in inhalation solutions or suspensions not containing propellant gases. Corresponding inhalation solutions not containing propellant gases contain, for example, aqueous or alcoholic, preferably ethanolic, if necessary ethanolics in mixture with aqueous solvents.

In the case of aqueous/ethanolic solvent mixtures, the relative proportion of ethanol to water is not limited; however, preferably the maximum limit is up to 70% (v/v), in particular up to 60% (v/v) in the case of ethanol. The remaining volume percents are topped off using water. The inhalation solutions not containing propellant gases according to the invention can, as described above, receive co-solvents or other excipients. For example, if co-solvents can be used, which contain hydroxyl groups or other polar groups such as, for example, alcohols, in particular isopropyl alcohol, glycols, in particular propyleneglycol, polyethyleneglycol, polypropyleneglycol, glycolether, glycerol, polyoxyethylene alcohols and polyoxythethylene fatty acid esters. Excipients and additives in this connection are defined as any pharmacologically acceptable substance, which is not an active substance but can be formulated with the active substance(s) in the pharmacologically suitable solvent, in order to improve upon the qualitative properties of the active substance formulation. Preferably, these substances do not induce or in the context of the therapy provided does not induce a noteworthy or at least does not induce any adverse pharmacological effect. In addition to the aforementioned excipients and additives, for example, the following are included: surface-active substances such as, for example, soy lecithin, oleic acid, sorbitan esters such as polysorbate, polyvinylpyrrolidone, other stabilizers, complexing agents, antioxidants and/or preservatives, which assure or extend the usable period of the medicinal product formulation, flavorings, vitamins and/or other additives known in the prior art Pharmacologically safe salts such as, for example, sodium chloride are included in the additives as isotoners. Antioxidants are included among the preferred excipients such as, for example, ascorbic acid, insofar as it is not already used for adjusting the pH, vitamin A, vitamin E, tocopherol and similar vitamins or pro-vitamins occurring in the human organism. Preservatives can be used, in order to protect the formulation from contamination with microbes. The preservatives well-known in the prior are suitable, in particular cetylpyridinium chloride, benzalconium chloride or benzoic acid or benzoates like sodium benzoate in the concentrations well-known in the prior art. The aforementioned preservatives are preferably contained in concentrations of up to 50 mg/100 ml, particularly preferably between 5 and 20 mg/100 ml. Accordingly, the present invention includes also inhalation aerosols not containing propellant gases, which are manufactured by reconstitution of the powders according to the invention.

For the administration of the inhalation aerosols not containing propellant gases according to the invention, those inhalers are particularly suitable, which can aerosolize a small quantity of a fluid formulation at the therapeutically necessary dose with a few seconds into a therapeutically inhalatively suitable aerosol. In the context of the present invention, such aerosolizers are preferred, in which a quantity of less than 100 μl, preferably less than 50 μl, particularly preferably between 10 and 30 μl of active substance using preferably one stroke can be converted to an aerosol having an average particle size of less that 20 μm, preferably less than 10 μm, so that the inhalable portion of the aerosol corresponds already to the therapeutically effective quantity.

This type of device for propellant-free administration of a dosed quantity of a fluid medicinal product for inhalative administration is extensively described, for example, in the international patent application WO 91/14468 and in WO 97/12687 (there, in particular, in FIGS. 6a and 6b). Express reference is made in the context of the present invention to the corresponding FIGS. 6a and 6b of WO 97/12687, including the relevant parts of the description. The aerosolizers (devices) are also known by the designation Respimat® (Boehringer Ingelheim Pharma). Because of its cylindrical form and its manageable size of less than 9 to 15 cm in length and 2 to 4 cm in width, this device can be carried by the patient at all times. The aerosolizer sprays a defined volume of the medicinal product formulation by using high pressure through small nozzles, so that inhalable aerosols are generated.

Essentially, the preferred aerosolizer consists of a upper housing part, a pump housing, anozzle, a blocking mechanism, a spring housing, a spring and a supply container, characterized in that

- the pump housing, which is affixed in the upper housing part, and which at its one end carries a nozzle body with the nozzle or the nozzle arrangement,
- a hollow piston with a valve body,
- a flange, in which the hollow piston is affixed, and which is arranged in the upper part of the housing,
- a blocking mechanism, which is arranged in the upper part of the housing,
- a spring housing together with the spring disposed therein, which is rotationally mounted on the upper part of the housing by means of a rotational bearing,
- a lower housing part, which is axially put on the spring housing.

The hollow piston with valve body corresponds to the device disclosed in WO 97/12687. It projects partially into the cylinder of the pump housing and is arranged moveably in the cylinder. Express reference is made, in particular in the context of the present invention, to FIGS. 1-4—particularly to FIG. 3—and the associated parts of the description. When triggering the spring the hollow piston with valve body exerts a pressure of from 5 to 60 Mpa (approximately 50 to 600 bar) on its high-pressure side, preferably 10 to 60 Mpa (approximately 100 to 600 bar) on the fluid, for the dosed active substance solution. In this case, volumes of from 10 to 50 microliters are preferred, particularly preferably are volumes of 10 to 20 microliters, most particularly preferred is a volume of 15 microliters per stroke.

The valve body is mounted preferably at the end of the hollow piston, which faces towards the nozzle body.

The nozzle in the nozzle body is preferably microstructured; that is, it is manufactured using micro-technology. Micro-structured nozzle bodies are disclosed in WO 94/07607, for example; in this document reference is made to the content, in particular to FIG. 1 and its description disclosed therein. The nozzle body is comprised of, for example, two glass and for silicon plates securely connected to each other, of which at least one plate has one or more of microstructured channels, which connect the nozzle inlet side with the nozzle outlet side. On the nozzle outlet side there is at least one round and one un-round opening of 2-10 μm in depth and 5-15 μm in width, wherein the depth is preferably 4.5 to 6.5 μm and the length is 7-9 μm. In the case of several nozzle openings, there are preferable two, the jet directions of the nozzles in the nozzle body can run parallel to each other or they are inclined in the direction of the nozzle opening, opposing each other. In the nozzle body having at least two nozzle openings on the outlet side, the jet directions can be inclined in opposition to each other at an angle of 20-160 degrees, preferably at an angle of 60-150 degrees, particularly preferably 80-100 degrees. The nozzle openings are preferably arranged at a distance of from 10-200 μm, more preferably at a distance of 10-100 μm, particularly preferably 30-70 μm. Most preferred are 50 μm.

As a result, the jet directions converge with each other in the area of the nozzle openings.

The fluid medicinal product preparations reaches, with this initial pressure of up to 600 bar, preferably 200 to 300 bar on the nozzle body and is atomized to an inhalable aerosol via the nozzle openings. The preferred particle or droplet sizes of the aerosol are in the range of up to 20 μm, preferably in the range of 3-10 μm.

The blocking mechanism contains a spring, preferably a cylindrical helical compression spring as the storage for the mechanical energy. The spring acts on the driven flange as the step part, whose movement is defined by the position of a blocking member. The path of the driven flange is precisely limited by an upper and a lower stop. The spring is preferably biased using a force transmitting gearing such as, for example, a helical advance gearing by means of an external torque, which is generated upon rotating the housing upper part against the spring housing in the housing lower part. In this instance, the housing upper part and the driven flanges receive a single or multiple wedge gearing.

The blocking member with enmeshing flocking surfaces is annularly arranged about the driven flange. It consists, for example, of a radially elastically deformable plastic or metal ring. The ring is arrange in one plane vertical to the aerosolizer axis. After tensioning the spring, the blocking surfaces of the blocking member are urged into the path of the driven flanges and prevent release of the spring. The blocking member is triggered by means of a button. The trigger button is connected or coupled to the blocking member. In order to release the blocking mechanism, the trigger button is urged parallel to the plane of the ring, preferably into the aerosolizer, when this is done, the deformable ring is deformed in the plane of the ring. Constructive details of the blocking mechanism are described in WO 97/20590.

The bottom part of the housing is urged axially over the spring housing and covers the bearing, the spindle drive and the supply container for the fluid.

When operating the aerosolizer, the upper part of the housing is rotated against the bottom part of the housing, whereby the bottom part of the housing carries the spring housing along. When this is done, the spring is compressed via the screw advance gearing and biased and the blocking mechanism automatically locks in. The angle of rotation is preferred to be an integer fraction of 360 degrees such as 180 degrees, for example. Simultaneously with the tensioning of the spring, the drive part in the upper part of the housing is displaced by a predefined path, the hollow piston is retracted within the cylinder in the pump housing, whereby a partial quantity of the fluid is sucked in out of the supply container into the high pressure space in front of the nozzle.

If necessary, more of replaceable supply containers containing the fluid to be aerosolized can be loaded into the aerosolizer and used. The supply container contains the aqueous aerosol preparation according to the invention.

The aerosolization operation is initiated by a slight pressing in of the trigger button. In this case, the blocking mechanism releases the way for the output part. The tensioned spring urges the piston into the cylinder of the pump housing. The fluid exits the nozzle of the aerosolizer in aerosolized form.

Other constructive details are disclosed in the PCT applications WO 97/12683 and WO 97/20590, to whose contents express reference is hereby made.

The components of the aerosolizer (nebulizer) are made of a suitable material corresponding to its function. The housing of the aerosolizer and—insofar as it allows function—also other parts are preferably made of plastic and manufactured using an injection molding process, for example. Physiologically safe materials are used for medical device purposes.

In FIGS. 6 a/b of WO 97/12687 including the associated description, to whose contents reference is made once again here, a corresponding aerosolizer (Respimat®) is described. This is especially suitable for administering the inhalation aerosols not containing propellant gases according to the invention.

FIG. 6a of WO 97/12687 shows a longitudinal section through the aerosolizer in the case of the tensioned spring, FIG. 6b of WO 97/12687 shows a longitudinal section through the aerosolizer in the case of relaxed spring. The upper part of the housing (51) contains the pump housing (52), at whose end the mounting (53) for the aerosolizer nozzle is attached. The nozzle body (54) and a filter (55) are arranged in the mounting. The hollow piston (57) affixed in the driven flange (56) of the blocking mechanism projects in part into the cylinder of the pump housing. At its end the hollow piston carries the valve body (58). The hollow piston is sealed by means of a seal (59). The stop (60) at which the driven flange rests in the case of the relaxed spring is arranged inside the upper part of the housing. On driven flange is the stop (61) by which the driven flange is held when the spring is biased. After the biasing of the spring, the generally annular blocking member (62) moves between the stop (61) and a support (63) in the upper housing part. The actuating button (64) is connected to the blocking member. The upper housing part terminates in the mouth piece (65) and is closed off by the protective cap (66) which can be fitted thereon. The spring housing (67) with compression spring (68) is rotatably mounted on the upper housing part by means of the snapping lug (69) and rotary bearing. The lower housing part (70) is pushed over the spring housing. Inside the spring housing is the replaceable storage container (71) for the fluid (72) which is to be atomized. The storage container is fitted with a stopper or cap (73) through which the hollow piston projects into the storage container and dips its end into the fluid. Mounted in the outer surface of the spring housing is the spindle (74) for the mechanical counter. At the end of the spindle facing the upper housing part is the drive pinion (75). The slider (76) sits on the spindle.

If the formulation according to the invention is aerosolized by means of the method described hereinbefore (Respimat®), the output mass should correspond in at least 97%, preferably at least 98% of all actuations of the inhaler (strokes) to a defined quantity with a tolerance range of a maximum of 25%, preferably 20% of said quantity. Preferably, between 5 and 30 mg, particularly preferably between 5 and 20 mg, of formulation is output as defined mass with each stroke.

The formulation according to the invention can, however, be aerosolized by means of inhalers other than the aforementioned such as Jet-Stream inhalers or other stationary aerosolizers, for example.

In consequence, a further aspect of the present invention relates to medicinal products in the form of inhalation solutions or suspensions not using propellant gas as hereinbefore described in conjunction with a device suitable for administering these formulations, preferably in conjunction with the Respimat®. Preferably, the present invention aims at inhalation solutions or suspensions not using propellant gases and containing one of the powders according to the invention in conjunction with the prior art devices under the designation Respimat®. In addition, the present invention relates to the aforementioned devices for inhalation, preferably the Respimat®, characterized in that they contain the hereinbefore described inhalation solutions or suspensions not containing propellant gas according to the invention.

Inhalation solutions containing one of the herein described powders according to the invention in a single pharmaceutical form are preferred according to the invention.

The inhalation solutions or suspensions not containing propellant gas according to the invention can, in addition to the aforementioned, may also be in the form of concentrates or sterile ready-to-use inhalation as solutions or suspensions for administration in the Respimat®. Ready-to-use formulations can be produced from the concentrates, for example, by addition of isotonic saline solutions. Sterile ready-to-use formulations can be administered by means of power-driven stationary or portable aerosolizers, that generate inhalable aerosols by means of ultrasound or compressed air according to the Venturi principle or other principles.

Accordingly, a further aspect of the present invention relates to medicinal products in the form of inhalation solutions or suspensions as hereinbefore described, which are in the form of concentrates or sterile ready-to-use formulations, in conjunction with a suitable device for administering said solutions, characterized in that said device is a power-driven stationary or portable aerosolizer, which generates aerosols by means of ultrasound or compressed air according to the Venturi principle or other principles.

Other suitable aerosolizers for inhalative application of reconstituted aerosols are the AERx™ (Aradigm), the Ultravent® (Mallinkrodt) and the Aconll® (Maquest Medical Products).

Embodiment Examples

Materials and methods

Materials

A humanized monoclonal antibody with a molecular weight of around 148 kDa of Boehringer Ingelheim, Germany was used as IgG1. The antibody is derived from a murine antibody wherein the complementary-determining regions of the murine antibody were transferred to a human antibody framework. This produced a chimeral antibody with a 95% human and 5% murine fraction. The antibody was expressed from murine myeloma cell strains. The cells are removed with the aid of tangential flow microfiltration and the cell-free solution cleansed by various chromatographic methods. Further steps include nuclease treatment, treatment at low pH value, and nanofiltration. The antibody-containing bulk solution contained 25 mM histidine and 1.6 mM glycine as buffer and was concentrated to around 100 mg/ml by diafiltration for production of the spray drying solution. The bulk for production of the solution to be sprayed contained 0.4 to 0.8% aggregates. The finished drug can be kept for at least two years at 2-8° C. Nyuka-Oligo® LS55P, Nyuka-Oligo® LS90P, Coupling Sugar®, and Coupling Sugar S® were supplied by Hayashibara Shoji Inc, Japan. Saccharose, lactose, mannitol, raffinose, hydroxyethyl starch, and L-isoleucine were supplied by Sigma-Aldrich Chemie GmbH, Germany. Trehalose was procured from Georg Breuer GmbH, Germany. Tri-isoleucine was supplied by Iris Biotech GmbH, Germany. Lysozyme from chicken albumen was supplied by SERVA Electrophoresis GmbH, Germany. Calcitonin was supplied by Biotrend Chemikalien GmbH, Germany.

Spray Drying with Büchi B-290

Spray drying was performed with the aid of a type B-290 Büchi Mini Spray Dryer of Büchi Labortechnik GmbH. Spray drying of the formulations was basically performed in accordance with the description given in "Spray Drying Handbook", 5$^{th}$ edition, K. Masters, John Wiley and Sons, Inc., NY, N.Y. (1991):

The sprayer dryer is built from a heating system, a filter, an aspirator, a drying system, a cyclone, temperature sensors for measurement of the inlet and outlet temperature, and a collecting vessel. A peristaltic pump is used to pump the solution to be sprayed into a twin-substance nozzle, where compressed air is used to atomize the solution into small droplets. Drying proceeds in the spraying tower by warmed air, which is drawn through the spraying tower by the aspirator in a continuous flow process. The product is collected in the collecting vessel after passing through the cyclone.

Two different cyclones were used:

Cyclone I: Büchi cyclone (serial number 4189)

Cyclone II: Büchi high-performance cyclone (serial number 46369)

The solids fraction of the sprayed solutions was 10% (w/v), 3.33%, and 2.00% in 50 to 600 ml. The inlet temperature was around 170 to 185° C., the liquid feed rate around 3 to 3.33 ml/min, the aspirator flow rate around 36.8 to 38.3 m$^3$/h, and the atomizing rate (AAF=atomizing air flow) around 0.67 m$^3$/h, 1.05 m$^3$/h, and 1.74 m$^3$/h, resulting in an outlet temperature of around 80-95° C.

Freeze Drying

Freeze drying was performed with the aid of a type Christ LPC-16/NT Epsilon 2-12 D freeze dryer of Martin Christ Gefriertrocknungsanlagen GmbH. The freeze dryer consists of a drying chamber, a condenser for separation of the sublimated solvent, a pump for vacuum generation, and electrical equipment. Drying is controlled via the control surface temperature and drying chamber vacuum.

The solids fraction of the freeze drying solution was 5% (w/v). The solution was portioned in 2R vials containing 0.5 ml each and placed in the freeze dryer with threaded freeze drying stoppers. The solutions were initially frozen at −40° C.×30 minutes. This was followed by main drying at 0.11 mbar in three steps: first −40° C.×30 hours, then −30° C.×8 hours, and finally −16° C.×8 hours. The next step was after-drying, which proceeded at 20° C.×20 hours×0.001 mbar. As a final step, the vials were automatically sealed with the freeze drying stoppers only inserted at the start. The thus obtained lyophilisates have been pulverized with a spatula inside the vials.

X-Ray Diffractometry (Wide-Angle X-Ray Diffractometry (WAXS))

To determine the crystallinity of the dried samples, the samples were investigated with a type XRD 3000 TT X-ray diffractometer (of Seifert, Ahrensburg, Germany) in a room attemperated to 22° C. The Cu anode X-ray tube using Cu—K$\alpha$ radiation with $\lambda$=0.15418 mm (Ni primary filter) was operated at an anodic voltage of 40 kV and current intensity of 30 mA. After the sample plate was placed in the instrument, the sample was measured over the 5 to 40° range at a scanning rate of $2\theta$=0.05° and measurement time of 2 seconds at each angle.

The powder diffractograms were recorded with the aid of the ScanX-Rayflex version 3.07, device XRD 3000 (Scan) and the Rayflex version 2.1, 1996 (analysis) on a type SC 1000 V detector.

Size Exclusion Chromatography (SEC-HPLC)

To quantify protein aggregates in the reconstituted powders, a SEC-HPLC was performed. The SEC-HPLC was performed with an HP 1090 of Messrs Agilent. A TSK3000SWXL column (300×7.8 mm) of Tosoh Biosep (Tosoh Bioscience, Stuttgart, Germany) was used for separation. As eluant, a buffer consisting of 0.1M disodium hydrogen phosphate dihydrate and 0.1M sodium sulphate was dehydrated and adjusted with 85% ortho-phosphoric acid to pH 6.8. The amount of sample charged was 25 µl at a protein concentration of 2-10 mg/ml. Protein detection was performed at 280 nm with the aid of a diode array detector of Agilent. HP Chemsation software of Agilent was used to evaluate the chromatograms.

Particle Size Determination (MMD)

The mass mean diameter (MMD) or the mean particle size was determined with the aid of the Sympatech Helos unit of Sympatech GmbH, Clausthal-Zellerfeld, Germany. The measurement principle is based on laser diffraction, a helium-neon laser being used. Some 1-3 mg powder are dispersed at an air pressure of 2 bar and guided in front of a 50 mm Fourier lens by a parallel laser beam. The particle size distribution is evaluated with a Fraunhofer model. Two measurements were performed per powder.

Mass Mean Aerodynamic Diameter (MMAD) and Fine Particle Fraction (FPF)

Some 12-18 mg powder respectively filled in size 3 hard-gelatin capsules and introduced into the Handihaler (powder inhaler of Boehringer Ingelheim) were used for the measurements. An adapter was used to couple the Handihaler to the USP EP throat of the instrument impactor inlet. The powder was drawn off at a rate of 39.01/min at a suction time of 6.15 seconds. The air throughput was controlled via an external control panel. At least three capsules were measured for each powder.

The APS 3321 unit of TSI Inc., MN, USA was simultaneously used in combination with the impactor inlet 3306 to determine the aerodynamic particle size (mass mean aerodynamic diameter, MMAD) via a time of flight determination and the fine particle fraction (FPF) via a single-stage impactor (with an effective cut-off diameter of 5.0 μm at 39 L/min). After being drawn off via the EP/USP throat or sample induction port, the powder passes to a thin capillary, where 0.2% of the powder quantity is sampled for time of flight measurement under isokinetic conditions. The time of flight measurement is performed after capillary passage through two laser beams, which, as in a light barrier, detect the flight times over a specific distance. The result is a numerical distribution that is subsequently converted into a mass distribution and then to the mass mean aerodynamic diameter (MMAD).

The residual 99.8% of the powder population that has passed by the capillary is separated via the single-stage impactor. The fraction greater than 5.0 μm separates in the impactor on an impact plate as a result of mass inertia. The fine particle fraction (FPF) follows the airflow, being finally separated in a depth filter. The fine particle fraction is gravimetrically determined. The fine particle fraction is calculated from the fraction of powder separated in the filter in relation to the total quantity of powder used, ie the weighed powder per capsule.

Residual Water Content

The residual water content of the dried products was determined by means of coulometric titration (Metrohm 737 KF coulometer with type 703 titration stand, Germany). To determine the residual water content, powder was dissolved or dispersed in methanol (Hydranal-Methanol dry, VWR/Merck Eurolab). The measured solution (Hydranal-Coulomat solution, VWR/Merck Eurolab) of the Metrohm coulometer was conditioned at the start of the measurements, ie the measured solution was calibrated to zero water content. The sample was injected into the titration cell and measured.

Stability Determination

The powders or proteins contained in the powder were investigated for different stabilities after spray drying. The percentage fraction of protein aggregates was set at the measurement unit for formulation stability. Pure protein formulations, analogous trehalose formulations, analogous raffinose formulations or analogous hydroxyethyl starch formulations were partially compared as references with the innovative adjuvants described in the invention. Aggregates were analyzed by validated size exclusion chromatography (SEC-HPLC) with UV detection (DAD). For this purpose, the pretreated powders were initially reconstituted in purest water (with a pH of 6 to 8).

Forced storage stability: Selected formulations were investigated for stability after one week's open storage at around 40° C. and around 75% relative air humidity (40° C., 75% RH) in open glass vials.

Equilibrated storage stability: Selected formulations after spray drying were stored in open glass vials for one day at around 22° C. and 50 to 55% relative air humidity (equilibration). The glass vials were subsequently sealed and beaded under the conditions specified above and investigated for stability after four weeks' dry storage at around 40° C.

Vacuum-dried storage stability: Selected formulations after spray drying were stored for one day in open glass vials in a vacuum drying cabinet of Memmert, Germany at around 30° C. and around 0.15 mbar (vacuum drying). The glass vials were subsequently removed from the vacuum drying cabinet, sealed, and beaded and investigated for stability after four weeks' dry storage at around 40° C.

1 month's stability: Selected formulations after spray drying were vacuum-dried in open glass vials (see above). The glass vials were sealed and beaded under nitrogen and stored at three different temperatures of 2-8° C., 25° C., and 40° C. The powders were investigated for stability after one month.

3 months' stability: For the method see under 1 month stability. The powders were investigated for stability after three months.

Open 1 month stability: Selected formulations after spray drying were respectively stored in open glass vials at 25° C. and around 29% and/or 43% relative air humidity. The powders were investigated for stability after one and three months. For selected formulations, the aerodynamic performance of the powder was also determined by means of time of flight measurements (see above).

Example 1

Spray Drying of a 10% (w/v) IgG1 Formulation

Pure IgG1 with a concentration of around 109 mg/ml formulated in a pH 6 glycine-histidine buffer (see Materials) was diluted with demineralized water (with a pH of around 7.5) to a content of 100 mg/ml and, in the absence of any other adjuvants, spray-dried as described above with application of cyclone I at an atomizing air flow of around 0.67 $m^3$/h. The solution volume was 50 ml. The aggregate content was investigated as described above.

After one week's open storage at 75% relative air humidity and 40° C. (forced storage stability), the solution prepared from the reconstituted powder had around 18.9% and 18.2% aggregates respectively.

After one day's equilibration and four weeks' dry storage at 40° C., the solution prepared from the reconstituted powder had around 11.8% aggregates.

After one day's vacuum drying and four weeks' dry storage at 40° C., the solution prepared from the reconstituted powder had around 13.2% aggregates.

Spray Drying of a 9% (w/v) trehalose

1% (w/v) IgG1 Formulation 4.5 g trehalose were dissolved in around 40 ml demineralized water (with a pH of around 7.5). As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The solution thus obtained contained around 9% (w/v) adjuvant or matrix and 1% (w/v) protein and was spray-dried as described above with application of cyclone I at an atomizing air flow of around 0.67 $m^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 12.6% aggregates.

Spray Drying of a 3.00% (w/v) LS90P 0.33% (w/v) IgG1 Formulation 4.5 g LS90P were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The solution thus obtained contained around 3.00% (w/v) adjuvant or matrix and 0.33% (w/v) protein and was spray-dried as described above with application of cyclone I at an atomizing air flow of around 0.67 m$^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 1.0% aggregates.

After 1 month's storage at 2-8° C. (1 month's stability), the solution prepared from the reconstituted powder had around 0.6% aggregates.

After 1 month's storage at 25° C. (1 month's stability), the solution prepared from the reconstituted powder had around 0.8% aggregates.

After 1 month's storage at 40° C. (1 month's stability), the solution prepared from the reconstituted powder had around 1.1% aggregates.

The MMD of the powder was determined as described above.

The MMD of the powder after spray drying was 2.8 µm.

The MMAD and FPF of the powder were determined as described above.

The MMAD of the powder after spray drying was 3.8 µm, and the FPF was 23.6% in relation to the weight of powder in the capsule.

Spray Drying of a 9.9% (w/v) LS55P 0.1% (w/v) IgG1 Formulation 4.950 g LS55P were dissolved in around 40 ml demineralized water (with a pH of around 7.5). As the next step, around 0.518 ml pure IgG1 with a concentration of around 96.55 mg/ml formulated in a pH 6 glycine-histidine buffer (see Materials) were added and diluted with demineralized water (with a pH of around 7.5) to a volume of 50 ml. The solution thus obtained contained around 9.9% (w/v) adjuvant or matrix and 0.1% (w/v) protein and was spray-dried as described above with application of cyclone I at an atomizing air flow of around 0.67 m$^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 5.7% aggregates.

After one day's vacuum drying and four weeks' dry storage at 40° C., the solution prepared from the reconstituted powder had around 4.7% aggregates.

Spray Drying of a 9% (w/v) LS55P

1% (w/v) IgG1 Formulation 4.5 g LS55P were dissolved in around 40 ml demineralized water (with a pH of around 7.5). As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The solution thus obtained contained around 9% (w/v) adjuvant or matrix and 1% (w/v) protein and was spray-dried as described above with application of cyclone I at an atomizing air flow of around 0.67 m$^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 2.3% aggregates.

After one day's equilibration and four weeks' dry storage at 40° C., the solution prepared from the reconstituted powder had around 1.8% aggregates.

After one day's vacuum drying and four weeks' dry storage at 40° C., the solution prepared from the reconstituted powder had around 1.4% aggregates.

Spray Drying of a 6% (w/v) LS55P

4% (w/v) IgG1 Formulation 3.0 g LS55P were dissolved in around 15 ml demineralized water (with a pH of around 7.5). As the next step, around 19.45 ml pure IgG1 with a concentration of around 102.8 mg/ml formulated in a pH 6 glycine-histidine buffer (see Materials) were added and diluted with demineralized water (with a pH of around 7.5) to a volume of 50 ml. The solution thus obtained contained around 6% (w/v) adjuvant or matrix and 4% (w/v) protein and was spray-dried as described above with application of cyclone I at an atomizing air flow of around 0.67 m$^3$/h. The aggregate content was investigated as described above.

The following aggregate contents were obtained for its storage stability:

After one week's open storage at 75% relative air humidity and 4° C. (forced storage stability), the solution prepared from the reconstituted powder had around 4.0% aggregates.

Spray Drying of a 4% (w/v) LS55P

6% (w/v) IgG1 Formulation 2.0 g LS55P were dissolved in around 15 ml demineralized water (with a pH of around 7.5). As the next step, around 29.18 ml pure IgG1 with a concentration of around 102.8 mg/ml formulated in a pH 6 glycine-histidine buffer (see Materials) were added and diluted with demineralized water (with a pH of around 7.5) to a volume of 50 ml. The solution thus obtained contained around 4% (w/v) adjuvant or matrix and 6% (w/v) protein and was spray-dried as described above with application of cyclone I at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 6.9% aggregates.

Spray Drying of a 2.5% (w/v) LS55P 7.5% (w/v) IgG1 Formulation 1.25 g LS55P were dissolved in around 10 ml demineralized water (with a pH of around 7.5). As the next step, around 38.84 ml pure IgG1 with a concentration of around 96.55 mg/ml formulated in a pH 6 glycine-histidine buffer (see Materials) were added and diluted with demineralized water (with a pH of around 7.5) to a volume of 50 ml. The solution thus obtained contained around 2.5% (w/v) adjuvant or matrix and 7.5% (w/v) protein and was spray-dried as described above with application of cyclone I at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 5.9% aggregates.

After one day's vacuum drying and four weeks' dry storage at 40° C., the solution prepared from the reconstituted powder had around 6.1% aggregates.

Spray Drying of a 1.0% (w/v) LS55P 9.0% (w/v) IgG1 Formulation 0.50 g LS55P was dissolved in around 5 ml demineralized water (with a pH of around 7.5). As the next step, around 41.43 ml pure IgG1 with a concentration of around 96.55 mg/ml formulated in a pH 6 glycine-histidine buffer (see Materials) were added and diluted with demineralized water (with a pH of around 7.5) to a volume of 50 ml. The solution thus obtained contained around 1.0% (w/v) adjuvant or matrix and 9.0% (w/v) protein and was spray-dried as described above with application of cyclone I at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 10.8% aggregates.

After one day's vacuum drying and four weeks' dry storage at 40° C., the solution prepared from the reconstituted powder had around 8.0% aggregates.

Spray Drying of a 0.5% (w/v) LS55P 9.5% (w/v) IgG1 Formulation 0.25 g LS55P was dissolved in around 2.5 ml demineralized water (with a pH of around 7.5). As the next step, around 46.21 ml pure IgG1 with a concentration of around 102.8 mg/ml formulated in a pH 6 glycine-histidine buffer (see Materials) were added and diluted with demineralized water (with a pH of around 7.5) to a volume of 50 ml. The solution thus obtained contained around 0.5% (w/v) adjuvant or matrix and 9.5% (w/v) protein and was spray-dried as described above with application of cyclone I at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 13.7% aggregates.

Spray Drying of a 3.00% (w/v) LS55P 0.33% (w/v) IgG1 Formulation 9.0 g LS55P were dissolved in around 280 ml demineralized water (with a pH of around 7.5). As the next step, around 9.73 ml pure IgG1 with a concentration of around 102.8 mg/ml formulated in a pH 6 glycine-histidine buffer (see Materials) were added and diluted with demineralized water (with a pH of around 7.5) to a volume of 300 ml. The solution thus obtained contained around 3.0% (w/v) adjuvant or matrix and 0.33% (w/v) protein and was spray-dried as described above using the cyclone II at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 5.0% aggregates.

The MMD of the powder was determined as described above.

The MMD of the powder after spray drying was 2.9 μm.

The MMAD and FPF of the powder were determined as described above.

The MMAD of the powder after spray drying was 4.3 μm, and the FPF was 15.9% in relation to the weight of powder in the capsule.

Spray Drying of a 9.9% (w/v) Coupling Sugar 0.1% (w/v) IgG1 Formulation 6.290 g Coupling Sugar-containing syrup (equivalent to 4.950 g Coupling Sugar) were dissolved in around 40 ml demineralized water (with a pH of around 7.5). As the next step, around 0.518 ml pure IgG1 with a concentration of around 96.55 mg/ml formulated in a pH 6 glycine-histidine buffer (see Materials) were added and diluted with demineralized water (with a pH of around 7.5) to a volume of 50 ml. The solution thus obtained contained around 9.9% (w/v) adjuvant or matrix and 0.1% (w/v) protein and was spray-dried as described above with application of cyclone I at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 14.9% aggregates.

Spray Drying of a 9% (w/v) Coupling Sugar

1% (w/v) IgG1 Formulation 5.71 g Coupling Sugar-containing syrup (equivalent to 4.5 g Coupling Sugar) were dissolved in around 40 ml demineralized water (with a pH of around 7.5). As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The solution thus obtained contained around 9% (w/v) adjuvant or matrix and 1% (w/v) protein and was spray-dried as described above with application of cyclone I at an atomizing air flow of around 0.67 m$^3$/h. The aggregate content was investigated as described above.

The following aggregate contents were obtained for its storage stability:
- After one week's open storage at 75% relative air humidity and 40° C. (forced storage stability), the solution prepared from the reconstituted powder had around 4.9% aggregates.

After one day's equilibration and four weeks' dry storage at 40° C., the solution prepared from the reconstituted powder had around 3.2% aggregates.

After one day's vacuum drying and four weeks' dry storage at 40° C., the solution prepared from the reconstituted powder had around 2.1% aggregates.

Spray Drying of a 6% (w/v) Coupling Sugar

4% (w/v) IgG1 Formulation 3.81 g Coupling Sugar-containing syrup (equivalent to 3.0 g Coupling Sugar) were dissolved in around 25 ml demineralized water (with a pH of around 7.5). As the next step, around 19.45 ml pure IgG1 with a concentration of around 102.8 mg/ml formulated in a pH 6 glycine-histidine buffer (see Materials) were added and diluted with demineralized water (with a pH of around 7.5) to a volume of 50 ml. The solution thus obtained contained around 6% (w/v) adjuvant or matrix and 4% (w/v) protein and was spray-dried as described above with application of cyclone I at an atomizing air flow of around 0.67 $m^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 5.0% aggregates.

Spray Drying of a 4% (w/v) Coupling Sugar

6% (w/v) IgG1 Formulation 2.54 g Coupling Sugar-containing syrup (equivalent to 2.0 g Coupling Sugar) were dissolved in around 15 ml demineralized water (with a pH of around 7.5). As the next step, around 29.18 ml pure IgG1 with a concentration of around x mg/ml formulated in a pH 6 glycine-histidine buffer (see Materials) were added and diluted with demineralized water (with a pH of around 7.5) to a volume of 50 ml. The solution thus obtained contained around 4% (w/v) adjuvant or matrix and 6% (w/v) protein and was spray-dried as described above with application of cyclone I at an atomizing air flow of around 0.67 $m^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 9.9% aggregates.

Spray Drying of a 2.5% (w/v) Coupling Sugar 7.5% (w/v) IgG1 Formulation 1.59 g Coupling Sugar-containing syrup (equivalent to 1.250 g Coupling Sugar) was dissolved in around 8 ml demineralized water (with a pH of around 7.5). As the next step, around 38.84 ml pure IgG1 with a concentration of around 96.56 mg/ml formulated in a pH 6 glycine-histidine buffer (see Materials) were added and diluted with demineralized water (with a pH of around 7.5) to a volume of 50 ml. The solution thus obtained contained around 2.5% (w/v) adjuvant or matrix and 7.5% (w/v) protein and was spray-dried as described above with application of cyclone I at an atomizing air flow of around 0.67 $m^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 10.8% aggregates.

Spray Drying of a 1.0% (w/v) Coupling Sugar 9.0% (w/v) IgG1 Formulation 0.653 g Coupling Sugar-containing syrup (equivalent to 0.50 g Coupling Sugar) was dissolved in around 5 ml demineralized water (with a pH of around 7.5). As the next step, around 41.43 ml pure IgG1 with a concentration of around 96.56 mg/ml formulated in a pH 6 glycine-histidine buffer (see Materials) were added and diluted with demineralized water (with a pH of around 7.5) to a volume of 50 ml. The solution thus obtained contained around 1.0% (w/v) adjuvant or matrix and 9.0% (w/v) protein and was spray-dried as described above with application of cyclone I at an atomizing air flow of around 0.67 $m^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 13.1% aggregates.

Spray Drying of a 9% (w/v) Coupling Sugar S

1% (w/v) IgG1 Formulation 5.86 g Coupling Sugar S-containing syrup (equivalent to 4.5 g Coupling Sugar S) were dissolved in around 40 ml demineralized water (with a pH of around 7.5). As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The solution thus obtained contained around 9% (w/v) adjuvant or matrix and 1% (w/v) protein and was spray-dried as described above with application of cyclone I at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 5.4% aggregates.

Example 2

Spray Drying of an 8% (w/v) trehalose 1% (w/v) L-isoleucine

1% (w/v) IgG1 Formulation 4.0 g trehalose and 0.5 g L-isoleucine were dissolved in around 40 ml demineralized water (with a pH of around 7.5) in an ultrasonic bath. As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The solution thus obtained contained around 9% (w/v) adjuvant or matrix and 1% (w/v) protein and was spray-dried as described above with application of cyclone I at an atomizing air flow of around 0.67 m³/h. The aggregate content was investigated as described above.

After one week's open storage at 75% relative air humidity and 40° C. (forced storage stability), the solution prepared from the reconstituted powder had around 22.2% aggregates.

Spray Drying of a 2.66% (w/v) LS90P 0.33% (w/v) L-isoleucine 0.33% (w/v) IgG1 Formulation 4.0 g LS90P and 0.50 g L-isoleucine were dissolved in around 140 ml demineralized water (with a pH of around 7.5) in an ultrasonic bath. As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The solution thus obtained contained around 3.00% (w/v) adjuvant or matrix and 0.33% (w/v) protein and was spray-dried as described above using the cyclone II at an atomizing air flow of around 0.67 m³/h. The aggregate content was investigated as described above.

The following aggregate contents were obtained for its storage stability:

After one week's open storage at 75% relative air humidity and 40° C. (forced storage stability), the solution prepared from the reconstituted powder had around 0.7% aggregates.

After 1 month's storage at 2-8° C. (1 month's stability), the solution prepared from the reconstituted powder had around 0.7% aggregates.

After 1 month's storage at 25° C. (1 month's stability), the solution prepared from the reconstituted powder had around 0.8% aggregates.

After 1 month's storage at 40° C. (1 month's stability), the solution prepared from the reconstituted powder had around 0.6% aggregates.

The MMAD and FPF of the powder were determined as described above.

The MMAD of the powder after spray drying was 7.3 μm, and the FPF was 28.1% in relation to the weight of powder in the capsule.

Spray Drying of an 8% (w/v) LS55P 1% (w/v) L-isoleucine

1% (w/v) IgG1 Formulation 4.00 g LS90P and 0.50 g L-isoleucine were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The solution thus obtained contained around 9% (w/v) adjuvant or matrix and 1% (w/v) protein and was spray-dried as described above with application of cyclone I at an atomizing air flow of around 0.67 m³/h. The aggregate content was investigated as described above.

After one week's open storage at 75% relative air humidity and 40° C. (forced storage stability), the solution prepared from the reconstituted powder had around 5.5% aggregates.

After one day's equilibration and four weeks' dry storage at 40° C., the solution prepared from the reconstituted powder had around 1.8% aggregates.

After one day's vacuum drying and four weeks' dry storage at 40° C., the solution prepared from the reconstituted powder had around 1.8% aggregates.

Spray Drying of a 2.66% (w/v) LS55P 0.33% (w/v) L-isoleucine 0.33% (w/v) IgG1 Formulation 8.0 g LS55P and 1 g L-isoleucine were dissolved in around 280 ml demineralized water (with a pH of around 7.5) in an ultrasonic bath. As the next step, around 9.7 ml pure IgG1 with a concentration of around 102.8 mg/ml formulated in a pH 6 glycine-histidine buffer (see Materials) were added and diluted with demineralized water (with a pH of around 7.5) to a volume of 300 ml. The solution thus obtained contained around 3% (w/v) adjuvant or matrix and 0.33% (w/v) protein and was spray-dried as described above using the cyclone II at an atomizing air flow of around 0.67 m³/h. The aggregate content was investigated as described above.

After one week's open storage at 75% relative air humidity and 40° C. (forced storage stability), the solution prepared from the reconstituted powder had around 5.9% aggregates.

After 1 and 3 months' storage at 2-8° C. (3 months' stability), the solution prepared from the reconstituted powder had around 1.6% aggregates respectively.

After 1 and 3 months' storage at 25° C. (3 months' stability), the solution prepared from the reconstituted powder had around 1.6% and 1.8% aggregates respectively.

After 1 and 3 months' storage at 40° C. (3 months' stability), the solution prepared from the reconstituted powder had around 1.6% and 1.8% aggregates respectively.

The MMAD and FPF of the powder were determined as described above.

The MMAD of the powder after spray drying was 4.9 μm, and the FPF was 34.7% in relation to the weight of powder in the capsule.

Spray Drying of an 8% (w/v) Coupling Sugar 1% (w/v) L-isoleucine

1% (w/v) IgG1 Formulation 5.08 g Coupling Sugar-containing syrup (equivalent to 4.0 g Coupling Sugar) and 0.50 g L-isoleucine were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The solution thus obtained contained around 9% (w/v) adjuvant or matrix and 1% (w/v) protein and was spray-dried as described above with application of cyclone I at an atomizing air flow of around 0.67 $m^3$/h. The aggregate content was investigated as described above.

- After one week's open storage at 75% relative air humidity and 40° C. (forced storage stability), the solution prepared from the reconstituted powder had around 7.1% aggregates.
- After one day's equilibration and four weeks' dry storage at 40° C., the solution prepared from the reconstituted powder had around 2.5% aggregates.
- After one day's vacuum drying and four weeks' dry storage at 40° C., the solution prepared from the reconstituted powder had around 1.1% aggregates.

Spray Drying of an 8% (w/v) Coupling Sugar S 1% (w/v) L-isoleucine

1% (w/v) IgG1 Formulation 5.21 g Coupling Sugar S-containing syrup (equivalent to 4.0 g Coupling Sugar S) and 0.50 g L-isoleucine were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The solution thus obtained contained around 9% (w/v) adjuvant or matrix and 1% (w/v) protein and was spray-dried as described above with application of cyclone I at an atomizing air flow of around 0.67 $m^3$/h. The aggregate content was investigated as described above.

- After one week's open storage at 75% relative air humidity and 40° C. (forced storage stability), the solution prepared from the reconstituted powder had around 6.8% aggregates.

Example 3

Spray Drying of a 3% (w/v) trehalose 6% (w/v) L-citrulline

1% (w/v) IgG1 Formulation 1.50 g trehalose and 3.00 g L-citrulline were dissolved in around 40 ml demineralized water (with a pH of around 7.5) in an ultrasonic bath. As the next step, around 4.6 ml pure IgG1 with a concentration of around 109 mg/ml formulated in a pH 6 glycine-histidine buffer (see Materials) were added and diluted with demineralized water (with a pH of around 7.5) to a volume of 50 ml. The solution thus obtained contained around 9% (w/v) adjuvant or matrix and 1% (w/v) protein and was spray-dried as described above with application of cyclone I at an atomizing air flow of around 0.67 $m^3$/h. The aggregate content was investigated as described above.

- After one week's open storage at 75% relative air humidity and 40° C. (forced storage stability), the solution prepared from the reconstituted powder had around 5.9% aggregates.

Spray Drying of a 3% (w/v) LS55P 6% (w/v) L-citrulline

1% (w/v) IgG1 Formulation 1.50 g LS55P and 3.00 g L-citrulline were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The solution thus obtained contained around 9% (w/v) adjuvant or matrix and 1% (w/v) protein and was spray-dried as described above with application of cyclone I at an atomizing air flow of around 0.67 $m^3$/h. The aggregate content was investigated as described above.

- After one week's open storage at 75% relative air humidity and 40° C. (forced storage stability), the solution prepared from the reconstituted powder had around 2.9% aggregates.
- After one day's equilibration and four weeks' dry storage at 40° C., the solution prepared from the reconstituted powder had around 1.8% aggregates.
- After one day's vacuum drying and four weeks' dry storage at 40° C., the solution prepared from the reconstituted powder had around 1.3% aggregates.

Spray Drying of a 3% (w/v) Coupling Sugar 6% L-citrulline

1% (w/v) IgG1 Formulation 1.91 g Coupling Sugar-containing syrup (equivalent to 1.5 g Coupling Sugar) and 3.00 g L-citrulline were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The solution thus obtained contained around 9% (w/v) adjuvant or matrix and 1% (w/v) protein and was spray-dried as described above with application of cyclone I at an atomizing air flow of around 0.67 $m^3$/h. The aggregate content was investigated as described above.

- After one week's open storage at 75% relative air humidity and 40° C. (forced storage stability), the solution prepared from the reconstituted powder had around 3.9% aggregates.
- After one day's equilibration and four weeks' dry storage at 40° C., the solution prepared from the reconstituted powder had around 1.4% aggregates.

After one day's vacuum drying and four weeks' dry storage at 40° C., the solution prepared from the reconstituted powder had around 1.3% aggregates.

Spray Drying of a 3% (w/v) Coupling Sugar S 6% L-citrulline

1% (w/v) IgG1 Formulation 1.95 g Coupling Sugar S-containing syrup (equivalent to 1.5 g Coupling Sugar S) and 3.00 g L-citrulline were dissolved in around 40 ml demineralized water (with a pH of around 7.5) in an ultrasonic bath. As the next step, around 4.60 ml pure IgG1 with a concentration of around 109 mg/ml formulated in a pH 6 glycine-histidine buffer (see Materials) were added and diluted with demineralized water (with a pH of around 7.5) to a volume of 50 ml. The solution thus obtained contained around 9% (w/v) adjuvant or matrix and 1% (w/v) protein and was spray-dried as described above with application of cyclone I at an atomizing air flow of around 0.67 m³/h. The aggregate content was investigated as described above.

After one week's open storage at 75% relative air humidity and 40° C. (forced storage stability), the solution prepared from the reconstituted powder had around 3.1% aggregates.

Example 4

Spray Drying of a 2.66% (w/v) trehalose 0.33% (w/v) tri-isoleucine 0.33% (w/v) IgG1 Formulation 8.0 g trehalose and 1 g tri-isoleucine were dissolved in around 280 ml demineralized water (with a pH of around 7.5) in an ultrasonic bath. As the next step, around 12.30 ml pure IgG1 with a concentration of around 96.55 mg/ml formulated in a pH 6 glycine-histidine buffer (see Materials) were added and diluted with demineralized water (with a pH of around 7.5) to a volume of 300 ml. The solution thus obtained contained around 3% (w/v) adjuvant or matrix and 0.33% (w/v) protein and was spray-dried as described above using the cyclone II at an atomizing air flow of around 0.67 m³/h. The aggregate content was investigated as described above.

After one week's open storage at 75% relative air humidity and 40° C. (forced storage stability), the solution prepared from the reconstituted powder had around 26.7% aggregates.

Spray Drying of a 2.66% (w/v) raffinose 0.33% (w/v) tri-isoleucine 0.33% (w/v) IgG1 Formulation 8.0 g raffinose and 1 g tri-isoleucine were dissolved in around 140 ml demineralized water (with a pH of around 7.5) in an ultrasonic bath. As the next step, around 4.87 ml pure IgG1 with a concentration of around 102.8 mg/ml formulated in a pH 6 glycine-histidine buffer (see Materials) were added and diluted with demineralized water (with a pH of around 7.5) to a volume of 300 ml. The solution thus obtained contained around 3% (w/v) adjuvant or matrix and 0.33% (w/v) protein and was spray-dried as described above using the cyclone II at an atomizing air flow of around 0.67 m³/h. The aggregate content was investigated as described above.

After one week's open storage at 75% relative air humidity and 40° C. (forced storage stability), the solution prepared from the reconstituted powder had around 12.6% aggregates.

Spray Drying of a 2.66% (w/v) Hydroxyethyl Starch (HES)

0.33% (w/v) tri-isoleucine 0.33% (w/v) IgG1 Formulation 8.0 g HES and 1 g tri-isoleucine were dissolved in around 140 ml demineralized water (with a pH of around 7.5) in an ultrasonic bath at around 80° C. with stirring. As the next step, around 4.87 ml pure IgG1 with a concentration of around 102.8 mg/ml formulated in a pH 6 glycine-histidine buffer (see Materials) were added to the previously refrigerated turbid solution and diluted with demineralized water (with a pH of around 7.5) to a volume of 150 ml. The solution thus obtained contained around 3% (w/v) adjuvant or matrix and 0.33% (w/v) protein and was spray-dried as described above using the cyclone II at an atomizing air flow of around 0.67 m³/h. The aggregate content was investigated as described above.

After one week's open storage at 75% relative air humidity and 40° C. (forced storage stability), the solution prepared from the reconstituted powder had around 18.6% aggregates.

After 1 month's open storage at around 43% relative air humidity and 25° C. (open 1 month's stability), the solution prepared from the reconstituted powder had around 11.9% aggregates.

Spray Drying of a 2.00% (w/v) saccharose 0.66% (w/v) lactose 0.33% (w/v) tri-isoleucine 0.33% (w/v) IgG1 Formulation 6.0 g saccharose, 2.0 g lactose, and 1 g tri-isoleucine were dissolved in around 280 ml demineralized water (with a pH of around 7.5) in an ultrasonic bath. As the next step, around 9.73 ml pure IgG1 with a concentration of around 102.8 mg/ml formulated in a pH 6 glycine histidine buffer (see Materials) were added and diluted with demineralized water (with a pH of around 7.5) to a volume of 300 ml. The solution thus obtained contained around 3% (w/v) adjuvant or matrix and 0.33% (w/v) protein and was spray-dried as described above using the cyclone II at an atomizing air flow of around 0.67 m³/h. The aggregate content was investigated as described above.

After one week's open storage at 75% relative air humidity and 40° C. (forced storage stability), the solution prepared from the reconstituted powder had around 8.8% aggregates.

Spray Drying of a 2.66% (w/v) saccharose 0.33% (w/v) tri-isoleucine 0.33% (w/v) IgG1 Formulation 8.0 g saccharose and 1 g tri-isoleucine were dissolved in around 280 ml demineralized water (with a pH of around 7.5) in an ultrasonic bath. As the next step, around 9.73 ml IgG1 with a concentration of around 102.8 mg/ml formulated in a pH 6 glycine-histidine buffer (see Materials) were added and diluted with demineralized water (with a pH of around 7.5) to a volume of 300 ml. The solution thus obtained contained around 3% (w/v) adjuvant or matrix and 0.33% (w/v) protein and was spray-dried as described above using the cyclone II at an atomizing air flow of around 0.67 m$^3$/h. The aggregate content was investigated as described above.

After one week's open storage at 75% relative air humidity and 40° C. (forced storage stability), the solution prepared from the reconstituted powder had around 5.6% aggregates.

Spray Drying of a 2.66% (w/v) LS90P 0.33% (w/v) tri-isoleucine 0.33% (w/v) IgG1 Formulation 4.0 g LS90P and 0.50 g tri-isoleucine were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The solution thus obtained contained around 3.00% (w/v) adjuvant or mark and 0.33% (w/v) protein and was spray-dried as described above using the cyclone II at an atomizing air flow of around 0.67 m$^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 2.3% aggregates.

After 1 month's storage at 2-8° C. (1 month's stability), the solution prepared from the reconstituted powder had around 0.7% aggregates.

After 1 month's storage at 25° C. (1 month's stability), the solution prepared from the reconstituted powder had around 0.8% aggregates.

After 1 month's storage at 40° C. (1 month's stability), the solution prepared from the reconstituted powder had around 0.9% aggregates.

The MMD of the powder was determined as described above.

The MMD of the powder after spray drying was 4.7 µm.

The MMAD and FPF of the powder were determined as described above.

The MMAD of the powder after spray drying was 4.8 µm, and the FPF was 53.2% in relation to the weight of powder in the capsule.

Spray Drying of a 2.66% (w/v) LS90P 0.33% (w/v) tri-isoleucine 0.33% (w/v) IgG1 Formulation 4.0 g LS90P and 0.50 g tri-isoleucine were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The solution thus obtained contained around 3.00% (w/v) adjuvant or matrix and 0.33% (w/v) protein and was spray-dried as described above using the cyclone II at an atomizing air flow of around 1.05 m$^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 2.2% aggregates.

After 1 month's open storage at 29% relative air humidity and 25° C. (open 1 month's stability), the solution prepared from the reconstituted powder had around 0.5% aggregates.

After 1 month's storage at around 43% relative air humidity and 25° C. (open 1 month's stability), the solution prepared from the reconstituted powder had around 0.5% aggregates.

The MMD of the powder was determined as described above.

The MMD of the powder after spray drying was 2.7 µm.

The MMAD and FPF of the powder were determined as described above.

The MMAD of the powder after spray drying was 3.6 µm, and the FPF was 58.0% in relation to the weight of powder in the capsule.

Spray Drying of a 2.66% (w/v) LS90P 0.33% (w/v) tri-isoleucine 0.33% (w/v) IgG1 Formulation 4.0 g LS90P and 0.50 g tri-isoleucine were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The solution thus obtained contained around 3.00% (w/v) adjuvant or matrix and 0.33% (w/v) protein and was spray-dried as described above using the cyclone II at an atomizing air flow of around 1.74 m$^3$/h. The aggregate content was investigated as described above.

The following aggregate contents were obtained for its storage stability:

After one week's open storage at 75% relative air humidity and 40° C. (forced storage stability), the solution prepared from the reconstituted powder had around % aggregates.

After 1 month's open storage at 29% relative air humidity and 25° C. (open 1 month's stability), the solution prepared from the reconstituted powder had around 0.5% aggregates.

After 1 month's open storage at 43% relative air humidity and 25° C. (open 1 month's stability), the solution prepared from the reconstituted powder had around 0.5% aggregates.

The MMD of the powder was determined as described above.

The MMD of the powder after spray drying was 2.6 µm.

The MMAD and FPF of the powder were determined as described above.

The MMAD of the powder after spray drying was 3.3 µm, and the FPF was 58.9% in relation to the weight of powder in the capsule.

Spray Drying of a 1.60% (w/v) LS90P 0.20% (w/v) tri-isoleucine 0.20% (w/v) IgG1 Formulation 4.0 g LS90P and 0.50 g tri-isoleucine were dissolved in around 220 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 250 ml. The solution thus obtained contained around 1.80% (w/v) adjuvant or matrix and 0.20% (w/v) protein and was spray-dried as described above using the cyclone II at an atomizing air flow of around 0.67 $m^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 2.2% aggregates.

After 1 month's open storage at 29% relative air humidity and 25° C. (open 1 month's stability), the solution prepared from the reconstituted powder had around 0.5% aggregates.

After 1 month's open storage at 43% relative air humidity and 25° C. (open 1 month's stability), the solution prepared from the reconstituted powder had around 0.7% aggregates.

The MMD of the powder was determined as described above.

The MMD of the powder after spray drying was 3.2 µm.

The MMAD and FPF of the powder were determined as described above.

The MMAD of the powder after spray drying was 3.9 µm, and the FPF was 55.6% in relation to the weight of powder in the capsule.

Spray Drying of a 2.833% (w/v) LS90P 0.166% (w/v) tri-isoleucine 0.33% (w/v) IgG1 Formulation 4.25 g LS90P and 0.25 g tri-isoleucine were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The solution thus obtained contained around 3.00% (w/v) adjuvant or matrix and 0.33% (w/v) protein and was spray-dried as described above using the cyclone II at an atomizing air flow of around 0.67 $m^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 1.5% aggregates.

After 1 month's open storage at 29% relative air humidity and 25° C. (open 1 month's stability), the solution prepared from the reconstituted powder had around 0.5% aggregates.

After 1 month's open storage at 43% relative air humidity and 25° C. (open 1 month's stability), the solution prepared from the reconstituted powder had around 0.5% aggregates.

The MMD of the powder was determined as described above.

The MMD of the powder after spray drying was 4.8 µm.

The MMAD and FPF of the powder were determined as described above.

The MMAD of the powder after spray drying was 5.2 µm, and the FPF was 45.7% in relation to the weight of powder in the capsule.

Spray Drying of a 2.9166% (w/v) LS90P 0.0833% (w/v) tri-isoleucine 0.33% (w/v) IgG1 Formulation 4.375 g LS90P and 0.125 g tri-isoleucine were dissolved in around 140 ml demineralized water (with a pH of around 7.5). As the next step, around 4.864 ml pure IgG1 with a concentration of around 102.8 mg/ml formulated in a pH 6 glycine-histidine buffer (see Materials) were added and diluted with demineralized water (with a pH of around 7.5) to a volume of 150 ml. The solution thus obtained contained around 3.00% (w/v) adjuvant or manic and 0.33% (w/v) protein and was spray-dried as described above using the cyclone II at an atomizing air flow of around 0.67 $m^3$/h. The aggregate content was investigated as described above.

The following aggregate contents were obtained for its storage stability:

After one week's open storage at 75% relative air humidity and 40° C. (forced storage stability), the solution prepared from the reconstituted powder had around 1.2% aggregates.

After 1 month's open storage at 29% and 43% relative air humidity and 25° C. (open 1 month's stability), the solution prepared from the reconstituted powder had around 0.4% and 0.5% aggregates.

The MMD of the powder was determined as described above.

The MMD of the powder after spray drying was 4.2 µm.

The MMAD and FPF of the powder were determined as described above.

The MMAD of the powder after spray drying was 6.1 µm, and the FPF was 39.6% in relation to the weight of powder in the capsule.

Spray Drying of a 2.66% (w/v) LS55P 0.33% (w/v) tri-isoleucine 0.33% (w/v) IgG1 Formulation 8.0 g LS55P and 1 g tri-isoleucine were dissolved in around 280 ml demineralized water (with a pH of around 7.5) in an ultrasonic bath. As the next step, around 9.73 ml pure IgG1 with a concentration of around 102.8 mg/ml formulated in a pH 6 glycine-histidine buffer (see Materials) were added and diluted with demineralized water (with a pH of around 7.5) to a volume of 300 ml. The solution thus obtained contained around 3% (w/v) adjuvant or matrix and 0.33% (w/v) protein and was spray-dried as described above using the cyclone II at an atomizing air flow of around 0.67 m³/h. The aggregate content was investigated as described above.

After one week's open storage at 75% relative air humidity and 40° C. (forced storage stability), the solution prepared from the reconstituted powder had around 2.1% aggregates.

After 1 and 3 months' storage at 2-8° C. (3 months' stability), the solution prepared from the reconstituted powder had around 0.8% and 1.5% aggregates respectively.

After 1 and 3 months' storage at 25° C. (3 months' stability), the solution prepared from the reconstituted powder had around 0.9% and 1.5% aggregates respectively.

After 1 and 3 months' storage at 40° C. (3 months' stability), the solution prepared from the reconstituted powder had around 1.3% and 2.6% aggregates respectively.

After 1 month's open storage at around 43% relative air humidity and 25° C., the solution prepared from the reconstituted powder had around 1.3%.

The MMD of the powder was determined as described above.

The MMD of the powder after spray drying was 3.4 μm.

The MMAD and FPF of the powder were determined as described above.

The MMAD of the powder after spray drying was 3.9 μm, and the FPF was 58.3% in relation to the weight of powder in the capsule.

After one month's storage at around 43% relative air humidity and 25° C. (open 3 months' stability), the MMAD was 3.8 μm, and the FPF was 59.6% in relation to the weight of powder in the capsule.

Spray Drying of a 2.833% (w/v) LS55P 0.166% (w/v) tri-isoleucine 0.33% (w/v) IgG1 Formulation 8.5 g LS90P and 0.5 g tri-isoleucine were dissolved in around 280 ml demineralized water (with a pH of around 7.5) in an ultrasonic bath. As the next step, around 9.73 ml pure IgG1 with a concentration of around 102.8 mg/ml formulated in a pH 6 glycine-histidine buffer (see Materials) were added and diluted with demineralized water (with a pH of around 7.5) to a volume of 300 ml. The solution thus obtained contained around 3% (w/v) adjuvant or matrix and 0.33% (w/v) protein and was spray-dried as described above using the cyclone II at an atomizing air flow of around 0.67 m³/h. The aggregate content was investigated as described above.

After one week's open storage at 75% relative air humidity and 40° C. (forced storage stability), the solution prepared from the reconstituted powder had around 3.4% aggregates.

The MMD of the powder was determined as described above.

The MMD of the powder after spray drying was 2.9 μm.

The MMAD and FPF of the powder were determined as described above.

The MMAD of the powder after spray drying was 4.4 μm, and the FPF was 58.6% in relation to the weight of powder in the capsule.

Spray Drying of a 2.9166% (w/v) LS55P 0.0833% (w/v) tri-isoleucine 0.33% (w/v) IgG1 Formulation 8.75 g LS90P and 0.25 g tri-isoleucine were dissolved in around 280 ml demineralized water (with a pH of around 7.5).

As the next step, around 9.73 ml pure IgG1 with a concentration of around 102.8 mg/ml formulated in a pH 6 glycine-histidine buffer (see Materials) were added and diluted with demineralized water (with a pH of around 7.5) to a volume of 300 ml. The solution thus obtained contained around 3% (w/v) adjuvant or matrix and 0.33% (w/v) protein and was spray-dried as described above using the cyclone II at an atomizing air flow of around 0.67 m³/h. The aggregate content was investigated as described above.

After one week's open storage at 75% relative air humidity and 40° C. (forced storage stability), the solution prepared from the reconstituted powder had around 4.4% aggregates.

The MMD of the powder was determined as described above.

The MMD of the powder after spray drying was 2.9 μm.

The MMAD and FPF of the powder were determined as described above.

The MMAD of the powder after spray drying was 4.4 μm, and the FPF was 58.6% in relation to the weight of powder in the capsule.

Example 5

Production of Further Powders According to the Invention

Spray Drying of a 3.33% (w/v) Lysozyme Formulation 5 g lysozyme are dissolved in 150 ml demineralized water (with a pH of around 7.5). The solution thus obtained is spray-dried as described above using the cyclone II with a spray rate of about 0.67 m³/h.

Spray Drying of a 3.00% (w/v) LS90P 0.33% (w/v) Lysozyme Formulation 9.0 g LS90P were dissolved in around 280 ml demineralized water (with a pH of around 7.5) in an ultrasonic bath. As the next step, 1 g lysozyme was added and the mixture was diluted to a volume of 300 ml. The solution thus obtained was adjusted to pH 7.0 with concentrated NaOH and spray-dried as described above using the cyclone II with a spray rate of about 0.67 m³/h.

Spray Drying of a 2.66% (w/v) LS90P 0.33% (w/v) isoleucine 0.33% (w/v) Lysozyme Formulation 8.0 g LS90P and 1 g isoleucine were dissolved in around 280 ml demineralized water (with a pH of around 7.5) in an ultrasonic bath. As the next step, 1 g lysozyme was added and diluted with demineralized water (with a pH of around 7.5) to a volume of 300 ml. The solution thus obtained was spray-dried as described above using the cyclone II with a spray rate of about 0.67 m³/h.

Spray Drying of a 2.66% (w/v) LS90P 0.33% (w/v) tri-isoleucine 0.33% (w/v) Lysozyme Formulation 8.0 g LS90P and 1 g tri-isoleucine were dissolved in around 280 ml demineralized water (with a pH of around 7.5) in an ultrasonic bath. As the next step, 1 g lysozyme was added and diluted with demineralized water (with a pH of around 7.5) to a volume of 300 ml. The solution thus obtained was adjusted to pH 7.0 with concentrated NaOH and spray-dried as described above using the cyclone II with a spray rate of about 0.67 m³/h.

Spray Drying of a 3.33% (w/v) Calcitonin Formulation 0.75 g calcitonin was diluted with demineralized water (with a pH of around 7.5) to a volume of 22.5 ml. The solution thus obtained was adjusted to pH 7.0 with concentrated NaOH and spray-dried as described above using the cyclone II with a spray rate of about 0.67 m³/h.

Spray Drying of a 3.166% (w/v) LS90P 0.166% (w/v) Calcitonin Formulation 4.75 g LS90P were dissolved in around 140 ml demineralized water (with a pH of around 7.5). As the next step, 0.25 g calcitonin was added and diluted with demineralized water (with a pH of around 7.5) to a volume of 150 ml. The solution thus obtained was adjusted to pH 7.0 with concentrated NaOH and spray-dried as described above using the cyclone II with a spray rate of about 0.67 m³/h.

Spray Drying of a 2.833% (w/v) LS90P 0.33% (w/v) tri-isoleucine 0.166% (w/v) Calcitonin Formulation 4.25 g LS90P and 0.50 g tri-isoleucine were dissolved in around 140 ml demineralized water (with a pH of around 7.5) in an ultrasonic bath. As the next step, 0.25 g calcitonin was added and diluted with demineralized water (with a pH of around 7.5) to a volume of 150 ml. The solution thus obtained was adjusted to pH 7.0 with concentrated NaOH and spray-dried as described above using the cyclone II with a spray rate of about 0.67 m³/h.

Spray Drying of a 2.66% (w/v) LS90P 0.33% (w/v) tri-isoleucine 0.33% (w/v) Calcitonin Formulation 4.00 g LS90P and 0.50 g tri-isoleucine were dissolved in around 140 ml demineralized water (with a pH of around 7.5) in an ultrasonic bath. As the next step, 0.50 g calcitonin was added and diluted with demineralized water (with a pH of around 7.5) to a volume of 150 ml. The solution thus obtained was adjusted to pH 7.0 with concentrated NaOH and spray-dried as described above using the cyclone II with a spray rate of about 0.67 m³/h.

Example 6

Freeze Drying of a 5% (w/v) IgG1 Formulation

Pure IgG1 with a concentration of around 109 mg/ml formulated in a pH 6 glycine-histidine buffer (see Materials) was diluted with demineralized water (with a pH of around 7.5) to a content of 50 mg/ml and freeze-dried in the absence of any other adjuvants. The solution had a volume of 50 ml and was distributed in commercial 2R vials before freeze drying. The lyophilisate was lyophilised in the 2R vials by means of a spatula and further treated as described above.

The aggregate content was investigated as described above.

After one week's open storage at 75% relative air humidity and 40° C. (forced storage stability), the solution prepared from the reconstituted powder had around 20.5% aggregates.

After one day's equilibration and four weeks' dry storage at 40° C., the solution prepared from the reconstituted powder had around 15.3% aggregates.

After one day's vacuum drying and four weeks' dry storage at 40° C., the solution prepared from the reconstituted powder had around 12.6% aggregates.

Freeze Drying of a 4.5% (w/v) Mannitol 0.5% (w/v) IgG1 Formulation 2.25 g mannitol were dissolved in around 40 ml demineralized water (with a pH of around 7.5). As the next step, 2.3 ml pure IgG1 with a concentration of around 109 mg/ml formulated in a pH 6 glycine-histidine buffer (see Materials) was diluted with demineralized water (with a pH of around 7.5) to a content of 50 mg/ml. The solution thus obtained contained around 4.5% (w/v) adjuvant or matrix and 0.5% (w/v) protein, was distributed in commercial 2R vials, and was freeze-dried as described above. The lyophilisate was lyophilised in the 2R vials by means of a spatula and further treated as described above. The aggregate content was investigated as described above.

The following aggregate contents were obtained for its storage stability:

After one week's open storage at 75% relative air humidity and 40° C. (forced storage stability), the solution prepared from the reconstituted powder had around 34.0% aggregates.

After one day's equilibration and four weeks' dry storage at 40° C., the solution prepared from the reconstituted powder had around 11.6% aggregates.

After one day's vacuum drying ani four weeks' dry storage at 40° C., the solution prepared from the reconstituted powder had around 6.2% aggregates.

Freeze Drying of a 4.5% (w/v) LS55P 0.5% (w/v) IgG1 Formulation 2.25 g LS55P were dissolved in around 40 ml demineralized water (with a pH of around 7.5). As the next step, 2.3 ml pure IgG1 with a concentration of around 109 mg/ml formulated in a pH 6 glycine-histidine buffer (see Materials) was diluted with demineralized water (with a pH of around 7.5) to a content of 50 mg/ml. The solution thus obtained contained around 4.5% (w/v) adjuvant or matrix and 0.5% (w/v) protein, was distributed in commercial 2R vials, and was freeze-dried as described above. The lyophilisate was lyophilised in the 2R vials by means of a spatula and further treated as described above. The aggregate content was investigated as described above.

The following aggregate contents were obtained for its storage stability:

After one week's open storage at 75% relative air humidity and 40° C. (forced storage stability), the solution prepared from the reconstituted powder had around 2.5% aggregates.

After one day's equilibration and four weeks' dry storage at 40° C., the solution prepared from the reconstituted powder had around 2.6% aggregates.

After one day's vacuum drying and fair weeks' dry storage at 40° C., the solution prepared from the reconstituted powder had around 1.2% aggregates.

Freeze Drying of a 4.5% (w/v) Coupling Sugar 0.5% (w/v) IgG1 Formulation 2.25 g Coupling Sugar were dissolved in around 40 ml demineralized water (with a pH of around 7.5). As the next step, 2.3 ml pure IgG1 with a concentration of around 109 mg/ml formulated in a pH 6 glycine-histidine buffer (see Materials) was diluted with demineralized water (with a pH of around 7.5) to a content of 50 mg/ml. The solution thus obtained contained around 4.5% (w/v) adjuvant or matrix and 0.5% (w/v) protein, was distributed in commercial 2R vials, and was freeze-dried as described above. The lyophilisate was lyophilised in the 2R vials by means of a spatula and further treated as described above. The aggregate content was investigated as described above.

The following aggregate contents were obtained for its storage stability:

After one week's open storage at 75% relative air humidity and 40° C. (forced storage stability), the solution prepared from the reconstituted powder had around 5.5% aggregates.

After one day's equilibration and four weeks' dry storage at 40° C., the solution prepared from the reconstituted powder had around 4.6% aggregates.

After one day's vacuum drying and four weeks' dry storage at 40° C., the solution prepared from the reconstituted powder had around 1.5% aggregates.

at 40° C. the solution obtained from the reconstituted powder had approx. 1.5% aggregates.

The invention claimed is:

1. A powder comprising particles of a pharmaceutical active substance, and one or more 1,4 O-linked saccharose derivatives chosen from the compounds:

1,4 O-linked D-gal-saccharose (lactosucrose), 1,4 O-linked D-glu-saccharose (glucosyl sucrose) and 1,4 O-linked glu-glu-saccharose (maltosyl sucrose), wherein the powder is a spray-dried powder, and wherein the particles in the spray-dried powder have a mass median aerodynamic diameter (MMAD) of between 1 and 7.5 μm.

2. The spray dried powder according to claim 1, wherein the saccharose derivative is lactosucrose.

3. The spray dried powder according to claim 2, wherein the spray dried powder in addition comprises one or more mono-, di- and/or polysaccharides.

4. The spray dried powder according to claim 3, wherein the spray-dried powder comprises in addition lactose and saccharose.

5. The spray dried powder according to any one of claims 2 to 4, wherein lactosucrose comprises at least 55% (w/w) by weight of the total sugar content contained in the powder.

6. The spray dried powder according to claim 1, comprising glucosyl sucrose and maltosyl sucrose.

7. The spray dried powder according to claim 6, wherein the spray dried powder in addition comprises one or more mono-, di- and/or polysaccharides.

8. The spray dried powder according to claim 7, wherein the spray-dried powder comprises in addition fructose, glucose and/or saccharose.

9. The spray dried powder according to any one of claims 6 to 8, wherein glucosyl sucrose and maltosyl sucrose comprise at least 25% (w/w) by weight of the total sugar content contained in the powder.

10. The spray dried powder according to claim 9, wherein maltosyl sucrose and glucosyl sucrose comprise at least 18% (w/w) by weight of the total sugar content contained in the powder.

11. The spray dried powder according to claim 1, wherein the spray dried powder comprises a sugar mixture comprising at least one 1,4 O-linked saccharose derivative, wherein the sugar mixture is between 25 and 99.99% (w/w) of the dry mass of the powder.

12. The spray dried powder according to claim 11, wherein the proportion of the pharmaceutical active substance is between 0.01 and 75% (w/w) of the dry mass of the powder.

13. The spray dried powder according to claim 12, wherein the pharmaceutical active substance is a biological macromolecule.

14. The spray dried powder according to claim 13, wherein the dry mass of the spray-dried powder comprises between 25 and 90% (w/w) of at least one 1,4 O-linked saccharose derivative or a sugar mixture comprising at least one 1,4 O-linked saccharose derivative and up to 75% (w/w) of a pharmaceutical active substance, wherein the proportion of lactosucrose, maltosyl sucrose and/or glycosyl sucrose comprise at least 20% (w/w) of the dry mass of the powder and the total of the weight percents relative to the powder is a maximum of 100% (w/w).

15. The spray dried powder according to claim 14, wherein the spray dried powder comprises one or more other pharmaceutically compatible excipients and/or one or more salts.

16. The spray dried powder according to claim 15, wherein the excipient is isoleucine.

17. The spray dried powder according to claim 15, wherein the excipient is a peptide.

18. The spray dried powder according to claim 17, wherein the excipient is a tri-peptide.

19. The spray dried powder according to claim 18, wherein the tri-peptide is tri-leucine.

20. The spray dried powder according to claim 16, wherein the dry mass of the spray-dried powder comprises between 25 and 90% (w/w) of at least one 1,4 O-linked saccharose derivative or a sugar mixture comprising at least one 1,4 O-linked saccharose derivative and between 1 and 19.99% (w/w) isoleucine, wherein the total of the weight percentages does not exceed 100% (w/w).

21. The spray dried powder according to claim 18, wherein the dry mass of the spray-dried powder comprises between 25 and 90% (w/w) of at least one 1,4 O-linked saccharose derivative or a sugar mixture comprising at least one 1,4 O-linked saccharose derivative and between 1 and 39% (w/w) of a tri-peptide.

22. The spray dried powder according to claim 1, wherein the particles in the powder have a mass median diameter (MMD) of between 1 and 10 μm.

23. A pharmaceutical composition comprising a spray-dried powder according to claim 1.

24. A process for manufacturing the spray-dried powder according to claim 1, comprising a) dissolving or suspending the pharmaceutical active substance in an aqueous solution/suspension;

b) dissolving or suspending one or more 1,4 O-linked saccharose derivatives chosen from the group comprising the compounds lactosucrose, glucosyl sucrose or maltosyl sucrose or a sugar mixture comprising at least one of these 1,4 O-linked saccharose derivatives in an aqueous solution/suspension;

c) mixing the solutions/suspensions to a combined solution/suspension;

d) spraying the combined solution/suspension at a temperature of less than 200/120° C. (inflow/outflow temperature) to a dried mass.

25. The process according to claim 24, wherein the pharmaceutical active substance is a biological macro-molecule.

26. The process according to claim 24, wherein the saccharose derivative is lactosucrose.

27. The process according to claim 26, wherein the combined solution/suspension comprises one or more mono-, di- or polysaccharides.

28. The process according to claim 27, wherein the combined solution/suspension in addition comprises lactose and saccharose.

29. The process according to claim 28, wherein lactosucrose comprises at least 55% (w/w) of the total sugar content present in the combined solution/suspension.

30. The process according to claim 24, wherein the saccharose derivative is a mixture of glucosyl sucrose and maltosyl sucrose.

31. The process according to claim 30, wherein the combined solution/suspension comprises one or more mono-, di- or polysaccharides.

32. The process according to claim 31, wherein the combined solution/suspension comprises fructose, saccharose and/or glucose.

33. The process according to claim 32, wherein glucosyl-sucrose and maltosyl-sucrose comprise at least 25% (w/w) by weight of the total sugar content present in the combined solution/suspension.

34. The process according to claim 33, wherein maltosyl-sucrose and glycosyl sucrose comprise at least 18% (w/w) by weight of the total sugar content present in the combined solution/suspension.

35. The process according to claim 34, wherein the 1,4 O-linked saccharose derivative or a sugar mixture comprising at least one 1,4 O-linked saccharose derivative comprises between 25 and 99.99% (w/w) of the dry mass of the combined solution/suspension.

36. The process according to claim 35, wherein the pharmaceutical active substance comprises between 0.01 and 75% (w/w) of the dry mass of the combined solution/suspension.

37. The process according to claim 36, wherein the combined solution/suspension comprises one or more other pharmaceutically acceptable excipients and/or one or more salts.

38. The process according to claim 37, wherein the excipient is an amino acid.

39. The process according to claim 38, wherein the amino acid is isoleucine.

40. The process according to claim 37, wherein the excipient is a peptide.

41. The process according to claim 40, wherein the excipient is a tri-peptide.

42. The process according to claim 41, wherein the tri-peptide is tri-isoleucine.

43. The process according to claim 39, wherein the dry mass of the combined solution/suspension comprises between 25 and 90% (w/w) of at least one 1,4 O-linked saccharose derivative or a sugar mixture comprising at least one 1,4 O-linked saccharose derivative and between 1 and 19.99% (w/w) isoleucine.

44. The process according to claim 41, wherein the dry mass of the combined solution/suspension comprises between 60 and 90% (w/w) of at least one 1,4 O-linked saccharose derivative or a sugar mixture comprising at least one 1,4 O-linked saccharose derivative and between 1 and 39% (w/w) of a tri-peptide.

45. The process according to claim 24, wherein the temperature is less than 186/96° C. (inflow/outflow temperature).

* * * * *